United States Patent [19]
Ross et al.

[11] Patent Number: 5,374,646
[45] Date of Patent: Dec. 20, 1994

[54] BENZOFURAN DERIVATIVES

[75] Inventors: Barry C. Ross, Luton; David Middlemiss, Bishops Stortford; David I. C. Scopes, Furneux Pelham; Torquil I. M. Jack, Bishops Stortford; Kevin S. Cardwell, Royston; Michael D. Dowle, Ware, all of England

[73] Assignee: Glaxo Group Limited, London, United Kingdom

[21] Appl. No.: 31,497

[22] Filed: Mar. 15, 1993

Related U.S. Application Data

[63] Continuation of Ser. No. 701,115, May 16, 1991, abandoned, which is a continuation-in-part of Ser. No. 620,075, Nov. 30, 1990, abandoned.

[30] Foreign Application Priority Data

Dec. 1, 1989 [GB] United Kingdom ............... 8927277
Dec. 22, 1989 [GB] United Kingdom ............... 8929071
May 18, 1990 [GB] United Kingdom ............... 9011186
Sep. 6, 1990 [GB] United Kingdom ............... 9019436

[51] Int. Cl.$^5$ ................... A61K 31/415; C07D 405/14
[52] U.S. Cl. ..................................... 514/382; 548/252; 548/253; 548/254
[58] Field of Search ............ 548/252, 253, 254; 514/382

[56] References Cited

U.S. PATENT DOCUMENTS 3,765,950 10/1973 Lauck ............................ 429/190
4,929,251  5/1990 Jache ............................ 429/190
5,190,942  3/1993 Poss ............................. 514/235.8

Primary Examiner—Patricia L. Morris
Attorney, Agent, or Firm—Bacon & Thomas

[57] ABSTRACT

The invention provides compounds of the general formula (I)

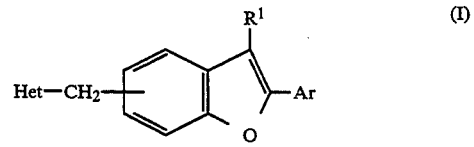

and physiologically acceptable salts, solvates or non-toxic metabolically labile esters thereof where $R^1$ represents a halogen atom; Ar represents the group

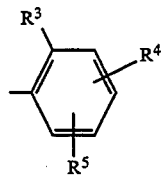

$R^3$ represents a C-linked tetrazolyl group;
$R^4$ and $R^5$, which may be the same or different, each independently represent a hydrogen atom or a halogen atom or a $C_{1-6}$ alkyl group; and
Het represents an N-linked imidazolyl group optionally substituted at the 2-position.

The compounds may be used in the treatment or prophylaxis of hypertension and diseases associated with cognitive disorders.

40 Claims, No Drawings

BENZOFURAN DERIVATIVES

This application is a continuation of application Ser. No. 07/701,115, filed May 16, 1991, now abandoned, which is a continuation-in-part of application Ser. No. 07/620,075, filed Nov. 30, 1990, now abandoned.

This invention relates to benzofuran derivatives, processes for their preparation and pharmaceutical compositions containing them. According to a first aspect of the invention we provide a compound of the general formula (I):

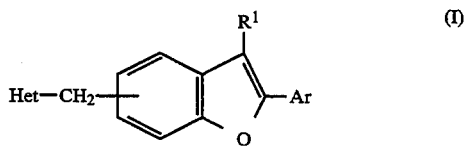

or a physiologically acceptable salt, solvate (e.g. hydrate) or metabolically labile ester thereof in which $R^1$ represents a hydrogen atom or a halogen atom or a group selected from $C_{1-6}$ alkyl, $C_{2-6}$ alkenyl, fluoro$C_{1-6}$alkyl, $C_{1-6}$alkoxy,—CHO, —CO$_2$H or —COR$^2$;

Ar represents the group

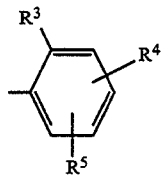

$R^2$ represents a group selected from $C_{1-6}$ alkyl, $C_{2-6}$ alkenyl, $C_{1-6}$ alkoxy or the group —NR$^{10}$R$^{11}$;

$R^3$ represents a group selected from —CO$_2$H, —NHSO$_2$CF$_3$ or a C-linked tetrazolyl group;

$R^4$ and $R^5$ which may be the same or different each independently represent a hydrogen atom or a halogen atom or a $C_{1-6}$ alkyl group;

Het represents an N-linked imidazolyl group optionally substituted at the 2-position by a $C_{1-6}$alkyl, $C_{2-6}$alkenyl or a $C_{1-6}$alkylthio group, the imidazolyl group optionally being substituted at the 4- and 5-positions by one or two further substituents selected from a halogen atom or a group selected from cyano, nitro, $C_{1-6}$alkyl, $C_{2-6}$alkenyl fluoro$C_{1-6}$alkyl, —(CH$_2$)$_m$R$^6$, —(CH$_2$)$_n$COR$^7$, or —(CH$_2$)$_p$NR$^8$COR$^9$;

$R^6$ represents a hydroxy or $C_{1-6}$alkoxy group;

$R^7$ represents a hydrogen atom or a group selected from hydroxy, $C_{1-6}$alkyl, $C_{1-6}$alkoxy, phenyl, phenoxy or the group —NR$^{10}$R$^{11}$;

$R^8$ represents a hydrogen atom or a $C_{1-6}$alkyl group;

$R^9$ represents a hydrogen atom or a group selected from $C_6$alkyl, $C_{1-6}$alkoxy, phenyl, phenoxy or the group —NR$^{10}$R$^{11}$.

$R^{10}$ and $R^{11}$, which may be the same or different, each independently represent a hydrogen atom or a $C_{1-4}$ alkyl group or —NR$^{10}$R$^{11}$ forms a saturated heterocyclic ring which has 5 or 6 ring members and may optionally contain in the ring one oxygen atom;

m represents an integer from 1 to 4, preferably 1 or 2, especially 1;

n represents an integer from 0 to 4, preferably 0, 1 or 2, especially 0 or 1; and p represents an integer from 1 to 4, preferably 1 or 2

Where optical isomers may exist formula (I) is intended to cover all enantiomers, diastereoisomers and mixtures thereof including racemates. Compounds containing one or two double bonds may exist in the cis or trans configuration.

The invention also includes within its scope the solvates, especially the hydrates of compounds of general formula (I).

Within the above definition the term 'alkyl' or 'alkoxy' as a group or part of a group means that the group is straight or branched. The term 'alkenyl' as a group or part of a group means that the group is straight or branched and contains at least one carbon-carbon double bond.

The term 'halogen' means a fluorine, chlorine, bromine or iodine atom.

The term 'fluoro$C_{1-6}$alkyl' means a $C_{1-6}$alkyl group in which one or more hydrogen atoms have been replaced by a fluorine atom, for example, —CH$_2$CF$_3$. Particularly preferred are 'perfluoro$C_{1-3}$alkyl' groups meaning a fully fluorinated $C_{1-3}$alkyl group, i.e. trifluoromethyl, pentafluoroethyl, heptafluoropropyl or heptafluoroisopropyl.

Within the above definition when —NR$^{10}$R$^{11}$ represents a saturated heterocyclic ring, this contains 5 or 6 ring members, one of which may be an oxygen atom. Suitable heterocyclic groups are a pyrrolidino, piperidino or morpholino group.

A preferred class of compounds of general formula (I) is that wherein the group Het is substituted at the 2-position by a hydrogen atom or a $C_{1-5}$alkyl, especially a $C_{3-5}$alkyl group or a $C_{3-5}$alkenyl group. Particularly preferred are those compounds wherein the 2-position substituent is an ethyl, n-propyl or n-butyl group, especially an n-butyl group. Conveniently, the $C_{3-5}$alkenyl group may be a but-1-enyl group.

Another preferred class of compounds of general formula (I) is that wherein the group Het is optionally substituted by one or two further substituents selected from a halogen atom or a group selected from $C_{1-6}$alkyl, —(CH$_2$)$_m$R$^6$ or —(CH$_2$)$_n$COR$^7$. In particular, R$^6$ represents a hydroxy or $C_{1-6}$alkoxy group, and preferably a hydroxy, methoxy, ethoxy, propoxy or butoxy group, and especially a hydroxy or methoxy group. R$^7$, in particular, represents a hydrogen atom or a hydroxy, $C_{1-6}$alkoxy or —NR$^{10}$R$^{11}$ group (especially wherein R$^{10}$ and R$^{11}$ each independently represent a hydrogen atom or a $C_{1-4}$alkyl group), and preferably a hydrogen atom or a hydroxy, methoxy, ethoxy, propoxy or butoxy group, and especially a hydrogen atom or a hydroxy or methoxy group, and m is 1 or 2 and n is 0, 1 or 2.

In particularly preferred embodiments of the present invention, the substituents are chosen from a chlorine atom and a group selected from —CH$_2$OH, —CHO, —CH$_2$OCH$_3$, —CO$_2$H, —CO$_2$CH$_3$,—CO$_2$CH$_2$CH$_3$,13 CONH$_2$ and —CONHCH$_3$.

A yet further preferred class of compounds of general formula (I) is that wherein R$^1$ represents a hydrogen atom or a halogen atom or a group selected from $C_{1-6}$alkyl, $C_{1-6}$alkoxy or fluoro$C_{1-6}$alkyl, and in particular a hydrogen atom or halogen atom or a $C_{1-3}$alkyl group. Especially preferred are compounds wherein R$^1$ is a bromine atom.

Conveniently, in the compounds of general formula (I), the group Het—CH$_2$—is attached at the 5- or 6-position on the benzofuran ring, and especially the 5-position.

Also conveniently, in the compounds of general formula (I), R$^3$ may be the group —CO$_2$H, or a C-linked tetrazolyl group. Still conveniently, in the compounds of general formula (I), R$^4$ and R$^5$ may each independently represent a hydrogen atom or a halogen atom. In particular R$^4$ and R$^5$ each represent hydrogen atoms.

Particularly preferred compounds of the invention include:

5-[2-[3-bromo-5-[[2-butyl-4-chloro-5-(hydroxymethyl)-1H-imidazol-1-yl]methyl]-2-benzofuranyl]phenyl]tetrazole;

1-[[3-bromo-2-[2-(1H-tetrazol-5-yl)phenyl]-5-benzofuranyl]methyl]-2-butyl-4-chloro-1H-imidazole-5-carboxaldehyde;

1-[[3-bromo-2-[2-(1H-tetrazol-5-yl)phenyl]-5-benzofuranyl]methyl]-2-butyl-4-chloro-1H-imidazole-5-carboxylic acid;

5-[2-[3-bromo-5-[(2-butyl-1H-imidazol-1-yl)methyl]-2-benzofuranyl]phenyl]-1H-tetrazole;

2-[3-bromo-5-[2-butyl-4-chloro-5-(hydroxymethyl)-1H-imidazol-1-yl]-2-benzofuranyl]benzoic acid;

5-[2-[5-[[2-butyl-4-chloro-5-(hydroxymethyl)-1H-imidazol-1-yl]methyl]-3-methyl-2-benzofuranyl]phenyl]-1H-tetrazole;

ethyl 1-[[3-bromo-2-[2-(1H-tetrazol-5-yl)phenyl]-5-benzofuranyl]methyl]-2-butyl -4-chloro-1H-imidazole-5-carboxylate 1-[[3-bromo-2-[2-(1H-tetrazol-5-yl)phenyl]-5-benzofuranyl]-methyl]-2-but-1-(E)-enyl-4-chloro-1H-imidazole-5-carboxylic acid;

1-[[3-bromo-2-[2-(1H-tetrazol-5-yl)phenyl]-5-benzofuranyl]methyl]-4-chloro-2-propyl-1H-imidazole-5-carboxylic acid;

1-[[3-bromo-2-[2-(1H-tetrazol-5-yl)phenyl]-5-benzofuranyl]methyl]-2-butyl-1H-imidazole-4,5-dicarboxylic acid;

5-[2-[3-bromo-5-[[2-butyl-4-chloro-5-(methoxymethyl)-1H-imidazol-1-yl]methyl]-2-benzofuranyl]phenyl]-1H-tetrazole;

2-butyl-4-chloro-1-[[2-[(1H-tetrazol-5-yl)phenyl]-3-(trifluoromethyl)-5-benzofuranyl]methyl]-1H-imidazole-5-carboxylic acid;

1-[[3-bromo-2-[2-(1H-tetrazol-5-yl)phenyl]benzofuran-5-yl]methyl]-2-butyl-4-chloro-1H-imidazole-5-carboxylic acid, 1-(acetyloxy)methyl ester;

1-[[3-bromo-2-[2-(1H-tetrazol-5-yl)phenyl]benzofuran-5-yl]methyl]-2-butyl-4-chloro-1H-imidazole-5-carboxylic acid, 1-(acetyloxy)ethyl ester, 1-(ethoxycarbonyloxy)ethyl 1-[[3-bromo-2-[2-(1H-tetrazol-5-yl)phenyl]-5-benzofuranyl]methyl]-2-butyl-4-chloro1H-imidazole-5-carboxylate;

2-methoxyethyl 1-[[3-bromo-2-[2-(1H-tetrazol-5-yl)phenyl]-5-benzofuranyl]methyl]-2-butyl-4-chloro-1H-imidazole-5-carboxylate;

1-[[3-bromo-2-[2-(1H-tetrazol-5-yl)phenyl]-5-benzofuranyl]methyl]-2-butyl-4-chloro-1H-imidazole-5-carboxamide;

1-[[1-[[3-bromo-2-[2-(1H-tetrazol-5-yl)phenyl]-5-benzofuranyl]methyl]-2-butyl-4-chloro-1H-imidazol-5-yl]carbonyl]pyrrolidine;

1-[[3-bromo-2-[2-(1H-tetrazol-5-yl)phenyl]-5-benzofuranyl]methyl]-2-butyl-4-chloro-N-methyl-1H-imidazole-5-carboxamide;

1-[[3-bromo-2-[2-(1H-tetrazol-5-yl)phenyl]-5-benzofuranyl]methyl]-2-butyl-4-chloro-N,N-dimethyl-1H-imidazole-5-carboxamide;

1-[[3-bromo-2-[2-(1H-tetrazol-5-yl)phenyl]-5-benzofuranyl]methyl]-2-butyl-4-chloro-N-ethyl-1H-imidazole-5-carboxamide;

1-[[3-bromo-2-[2-(1H-tetrazol-5-yl)phenyl]-5-benzofuranyl]methyl]-4-chloro-2-ethyl-1H-imidazole-5-carboxylic acid;

1-[[3-bromo-2-[2-(1H-tetrazol-5-yl)phenyl]-5-benzofuranyl]methyl]-2-butyl-1H-imidazole-5-carboxylic acid;

1-[[3-bromo-2-[2-(1H-tetrazol-5-yl)phenyl]-5-benzofuranyl]methyl]-4-chloro-2-propyl-N-methyl-1H-imidazole-5-carboxamide;

1-[[3-bromo-2-[2-(1H-tetrazol-5-yl)phenyl]-5-benzofuranyl]methyl]-2-butyl-4-chloro-N-isopropyl-1H-imidazole-5-carboxamide;

1-[[3-bromo-2-[2-(1H-tetrazol-5-yl)phenyl]-5-benzofuranyl]methyl]-2-butyl-4-iodo-1H-imidazole-5-carboxylic acid;

1-[[3-bromo-2-[2-(1H-tetrazol-5-yl)phenyl]-5-benzofuranyl]methyl]-2-butyl-4-trifluoromethyl-1H-imidazole-5-carboxylic acid;

1-[[3-bromo-2-[2-(1H-tetrazol-5-yl)phenyl]-5-benzofuranyl]methyl]-2-butyl-4-methyl-1H-imidazole-5-carboxylic acid, hydrochloride (1:1);

1-[[3-bromo-2-[2-(1H-tetrazol-5-yl)phenyl]-5-benzofuranyl]methyl]-2-butyl-4-chloro-1H-imidazole-5-acetic acid;

ethyl 1-[[3-bromo-2- [2-(1H-tetrazol-5-yl)phenyl]-5-benzofuranyl]methyl]-2-butyl-4-chloro-1H-imidazole-5-acetate;

1-[[3-bromo-2-[2-(ethoxycarbonyl)phenyl]-5-benzofuranyl]methyl]-2-butyl-4-chloro-1H-imidazole-5-carboxylic acid;

1-[[3-bromo-2-(2-carboxyphenyl)-5-benzofuranyl]methyl]-2-butyl-4-chloro-1H-imidazole-5-carboxylic acid;

methyl [[1-[[3-Bromo-2-[2-(1H-tetrazol-5-yl)phenyl]-5-benzofuranyl]methyl]-2-butyl-4-chloro-1H-imidazol-5-yl]methyl]carbamate;

1-[5-[3-chloro-2-[2-(1H-tetrazol-5-yl)phenyl]benzofuranyl]methyl]-2-butyl-4-chloro-1H-imidazole-5-carboxylic acid;

1-[[3-methoxy-2-[2-(1H-tetrazol-5-yl)phenyl]-5-benzofuranyl]methyl]-2-butyl-4-chloro-1H-imidazole-5-carboxylic acid;

2-methoxy-1-methylethyl 1-[[3-bromo-2-[2-(1H-tetrazol-5-yl)phenyl]-5benzofuranyl]-methyl]-2-butyl-4-chloro-1H-imidazole-5-carboxylate;

1-[[3-bromo-2-[2-[[(trifluoromethyl)sulphonyl]amino]-phenyl]-5benzofuranyl]-5-methyl]-2-butyl-4-chloro-1H-imidazole-5-carboxylic acid;

and physiologically acceptable salts, solvates and metabolically labile esters thereof.

In accordance with the first aspect of the present invention, there is also provided a compound of the general formula (I) above or a physiologically acceptable salt, solvate or metabolically labile ester thereof wherein R$^1$ represents a hydrogen atom or a halogen atom or a group selected from C$_{1-6}$alkyl, C$_{1-6}$alkoxy or fluoro C$_{1-6}$alkyl;

Ar represents the group

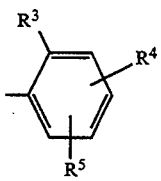

$R^3$ represents a group selected from $-CO_2H$, $-NHSO_2CF_3$ or a C-linked tetrazolyl group;

$R^4$ and $R^5$ each independently represent a hydrogen atom or a halogen atom;

Het represents an N-linked imidazolyl group optionally substituted at the 2-position by a $C_{1-6}$alkyl or $C_{2-6}$alkenyl group, the imidazolyl group optionally being substituted at the 4- and 5-positions by one or two further substituents selected from a halogen atom or a group selected from $C_{1-6}$alkyl, $-(CH_2)_mR^6$, $-(CH_2)_nCOR^7$ or $-(CH_2)_pNR^8COR^9$;

$R^6$ represents a hydroxy or a $C_{1-6}$alkoxy group;

$R^7$ represents a hydrogen atom or a group selected from hydroxy, $C_{1-6}$alkoxy or the group $-NR^{10}R^{11}$;

$R^8$ represents a hydrogen atom;

$R^9$ represents a hydrogen atom or a group selected from $C_{1-6}$alkyl, $C_{1-6}$alkoxy or the group $-NR^{10}R^{11}$;

$R^{10}$ and $R^{11}$ each independently represent a hydrogen atom or a $C_{1-4}$alkyl group or $-NR^{10}R^{11}$ forms a pyrrolidino heterocyclic ring;

m represents an integer from 1 or 4;

n represents an integer from 0 to 4; and p represents an integer from 1 to 4.

The physiologically acceptable acid addition salts of the compounds of formula (I) may be derived from inorganic or organic acids. Examples of such salts include hydrochlorides, hydrobromides, sulphates, phosphates, benzoates, methanesulphonates or trifluoroacetates.

The compounds may also form salts with suitable bases. Examples of such salts are alkali metal (e.g. sodium or potassium), alkaline earth metal (e.g. calcium or magnesium), ammonium and substituted ammonium (e.g. dimethylammonium, triethylammonium, 2-hydroxyethyldimethylammonium, piperazinium, N,N-dimethylpiperazinium, tetralkylammonium, piperidinium, ethylenediammonium and choline).

It will be appreciated that, for pharmaceutical use, the salts referred to above will be physiologically acceptable, but other salts may find use, for example, in the preparation of the compounds of formula (I) and the physiologically acceptable salts thereof.

It will be further appreciated that the compounds of general formula (I) may be chemically modified in the form of compounds which in vivo (for example, by enzymic attack) will provide the parent compounds of general formula (I). Such prodrugs may be, for example, physiologically acceptable metabolically labile ester derivatives. These may be formed by esterification, for example of any of the carboxylic acid groups in the parent compound of general formula (I), with prior protection of any other reactive groups present in the molecule. Examples of such esters include lower alkyl esters (e.g. methyl or ethyl esters), alkenyl esters (e.g. vinyl or allyl esters), alkynyl esters (e.g. ethynyl or propynyl esters), alkoxyalkyl esters, (e.g. methoxymethyl or 2-methoxyethyl esters), alkylthioalkyl esters (e.g. methylthiomethyl esters) haloalkyl esters (e.g. 2-iodoethyl or 2,2,2,-trichloroethyl esters), alkanoyloxyalkyl esters (e.g. acetoxymethyl, 1-acetoxyethyl or pivaloyloxymethyl esters), alkoxycarbonyloxyalkyl esters (e.g. 1ethoxycarbonyloxyethyl or 1-methoxycarbonyloxyethyl esters), aroyloxyalkyl esters (e.g. benzoyloxymethyl or 1-benzoyloxyethyl esters), substituted or unsubstituted aralkyl esters (e.g. benzyl or 4-amidobenzyl esters), substituted or unsubstituted aminoalkyl esters (e.g. aminoethyl or 2-N,N-dimethylaminoethyl esters) or hydroxyalkyl esters (e.g. 2-hydroxyethyl or 2,3-dihydroxypropyl esters).

In addition to the above ester derivatives the present invention includes within its scope compounds of general formula (I) in the form of other physiologically acceptable equivalents, i.e. physiologically acceptable compounds which, like the metabolically labile esters, are converted in vivo into the parent compounds of general formula (I).

According to a second aspect of the present invention we provide a compound of formula (I) or a physiologically acceptable salt, solvate or metabolically labile ester thereof for use in therapy.

In particular, the compounds of the invention may be used in the treatment or prophylaxis of hypertension. They are also potentially useful for the treatment of cognitive disorders such as dementia (e.g. Alzheimer's disease) and other diseases such as renal failure, hyperaldosteronism, thrombosis, cardiac insufficiency, congestive heart failure, post-myocardial infarction, cerebrovascular disorders, glaucoma and disorders of intracellular homeostasis.

According to a further aspect of the present invention we provide a compound of formula (I) or a physiologically acceptable salt, solvate or metabolically labile ester thereof for use in the treatment of the aforementioned diseases, especially hypertension.

According to another aspect of the present invention we provide a compound of formula (I) or a physiologically acceptable salt, solvate or metabolically labile ester solvate thereof for the manufacture of a therapeutic agent for the treatment of the aforementioned diseases, especially hypertension.

According to a further aspect of the present invention we provide a method of treating the aforementioned diseases, especially hypertension, which method comprises administering an effective amount to a patient in need of such treatment of a compound of formula (I) or a physiologically acceptable salt, solvate or metabolically labile ester thereof.

It will be appreciated that the compounds of formula (I) or a physiologically acceptable salt, solvate, or metabolically labile ester thereof may advantageously be used in conjunction with one or more other therapeutic agents, such as for example diuretics and/or different antihypertensive agents such as β-blockers, calcium channel blockers or ACE inhibitors. It is to be understood that such combination therapy constitutes a further aspect of the present invention.

It will be further appreciated that reference herein to treatment extends to prophylaxis as well as to the treatment and relief of established symptoms.

While it is possible that a compound of general formula (I) may be administered as the raw chemical it is preferable to present the active ingredient as a pharmaceutical formulation.

The compounds of formula (I) and their physiologically acceptable salts, solvates and metabolically labile esters may be formulated for administration in any convenient way, and the invention also includes within its scope pharmaceutical compositions comprising at least one compound of formula (I) or a physiologically acceptable salt, solvate or metabolically labile ester thereof adapted for use in human or veterinary medicine. Such compositions may be presented for use in conventional manner in admixture with one or more physiologically acceptable carriers or excipients. The carrier(s) must be 'acceptable' in the sense of being compatible with the other ingredients of the formulation and not deleterious to the recipient thereof.

Thus, the compounds according to the invention may be formulated for oral, buccal, parenteral or rectal administration or in a form suitable for administration by inhalation or insufflation. Oral administration is preferred.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup or carboxymethyl cellulose; emulsifying agents, for example, sorbitan monooleate; non-aqueous vehicles (which may include edible oils), for example, propylene glycol or ethyl alcohol; and preservatives, for example, methyl or propyl p-hydroxybenzoates or sorbic acid. The compounds or their salts or esters may also be formulated as suppositories, e.g. containing conventional suppository bases such as cocoa butter or other glycerides. For buccal administration the composition may take the form of tablets or lozenges formulated in conventional manner.

It will be appreciated that both tablets and capsules may be manufactured in the form of sustained release formulations, such that they provide a controlled continuous release of the compounds according to the invention over a period of hours.

The compounds of formula (I) and their physiologically acceptable salts, solvates and metabolically labile esters may be formulated for parenteral administration by bolus injection or continuous infusion and may be presented in unit dose form in ampoules, or in multidose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoro methane, dichlorotetrafluoroethane or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The pharmaceutical formulations according to the invention may also contain other active ingredients such as antimicrobial agents, or preservatives.

It will be appreciated that the amount of a compound of general formula (I) required for use in treatment will vary not only with the particular compound selected but also with the route of administration, the nature of the condition being treated and the age and condition of the patient and will ultimately be at the discretion of the attendant physician or veterinarian. In general, however, when the compositions comprise dosage units, each unit will preferably contain 5 mg to 500 mg, advantageously where the compounds are to be administered orally 25 mg to 400 mg of the active compound. The daily dosage as employed for adult human treatment will preferably range from 5 mg to 3 g, most preferably from 25 mg to 1 g which may be administered in 1 to 4 daily doses.

The compounds of the invention may be prepared by a number of processes as described below wherein the various groups are as defined for general formula (I) unless otherwise specified.

Thus, according to a further aspect of the present invention we provide a process (A) for preparing the compounds of general formula (I) which comprises treating a compound of general formula (II)

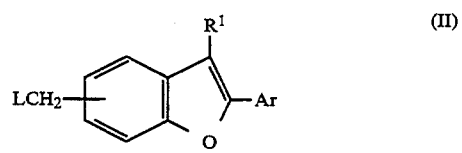

(wherein L is a leaving group, for example a halogen atom such as chlorine, bromine or iodine, or a hydrocarbylsulphonyloxy group such as methanesulphonyloxy, or p-toluenesulphonyloxy and $R^1$ and Ar are as defined in general formula (I)) with an imidazole of formula (II)

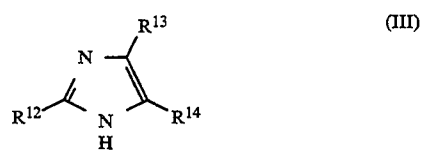

(wherein $R^{12}$ represents a hydrogen atom or a group selected from $C_{1-6}$alkyl, $C_{2-6}$alkenyl or $C_{1-6}$alkylthio; $R^{13}$ and $R^{14}$ which may be the same or different each independently represent a hydrogen or halogen atom, or a group selected from cyano, nitro, $C_{1-6}$alkyl, $C_{2-6}$alkenyl, fluoro$C_{1-6}$alkyl, $-(CH_2)_mR^6$, $-(CH_2)_nCOR^7$, —(CH$_2$)$_p$NR$^8$COR$^9$; and R$^6$, R$^7$, R$^8$, R$^9$, m, n and p are as defined in general formula (I)) followed by the removal of any protecting groups where present, as described hereinafter.

The reaction is preferably effected under basic conditions, for example, in the presence of sodium hydride, potassium carbonate or sodium methoxide. The reaction is conveniently effected in a solvent such as acetonitrile or an ether e.g. tetrahydrofuran or dioxan, a ketone e.g. butanone or methyl isobutyl ketone, or a substituted amide e.g. dimethylformamide, at a temperature between 0° C. and the reflux temperature of the solvent.

The intermediate compounds of general formula (II) and their acid addition salts are novel compounds and form a further aspect of the present invention.

In another general process (B) a compound of general formula (I) may be obtained by deprotection of a protected intermediate of general formula (IV)

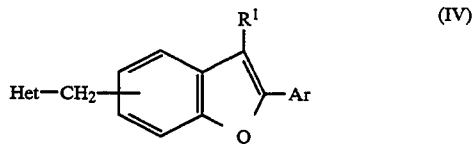
(IV)

(wherein R$^1$, Ar and Het are as defined in general formula (I) except that at least one reactive group is blocked by a protecting group).

The protecting groups may be any conventional protecting groups, for example as described in "Protective Groups in Organic Synthesis" by Theodora Greene (John Wiley and Sons Inc., 1981). Examples of carboxyl protecting groups include C$_{1-6}$ alkyl such as methyl or t-butyl, or C$_{7-10}$ aralkyl such as benzyl.

When R$^3$ is a tetrazole group, this may be protected with, for example, the trityl group —C(phenyl)$_3$, or a p-nitrobenzyl or 1-ethoxyethyl group.

Deprotection to yield the compound of general formula (I) may be effected using conventional techniques. Thus, for example, aralkyl groups may be cleaved by hydrogenolysis in a suitable organic solvent such as an alcohol, e.g. ethanol, in the presence of a noble metal catalyst such as palladium or platinum or an oxide thereof on a support such as charcoal, and conveniently at room temperature and pressure. Carboxyl protecting groups such as alkyl groups may be cleaved by hydrolysis using a base such as an alkali metal hydroxide (e.g. sodium hydroxide or potassium hydroxide) in a suitable solvent (e.g. an aqueous alcohol such as methanol or ethanol) at any suitable temperature up to reflux. Deprotection of the tetrazole group when protected with a trityl group may be effected by acid hydrolysis using trifluoroacetic acid or a mineral acid such as hydrochloric acid in a suitable solvent such as ethanol conveniently at room temperature. Alternatively, when possible, deprotection of the tetrazolyl group can be effected by catalytic hydrogenation as previously described.

In another general process (C) a compound of general formula (I) in which the substituent R$^3$ in the group Ar represents a C-linked tetrazolyl group (and the imidazolyl group represented by Het is not substituted by a cyano group), may also be prepared from a compound of general formula (Ia)

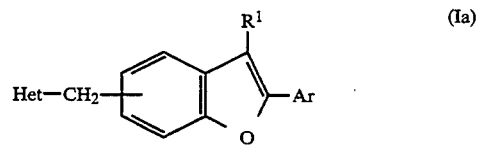
(Ia)

(wherein R$^1$, Ar and Het are as defined in general formula (I) except that in the group Ar, R$^3$ represents a nitrile group) by reaction with a suitable azide such as sodium azide, ammonium azide (preferably prepared in situ from sodium azide and ammonium chloride), trialkyl-(e.g. triethyl) ammonium azide (preferably prepared in situ from sodium azide and a trialkylamine (e.g. triethylamine)) or tributyl tin azide. The reaction is conveniently effected in a solvent such as xylene at an elevated temperature, such as the reflux temperature of the solvent, for between 1 and 10 days. Where the azide is tributyl tin azide the reaction may conveniently be effected in the absence of a solvent at a temperature between room temperature and 180° C. Such a reaction leaves the tetrazolyl group protected with a tributyl tin group, which can readily be removed using aqueous base or acid. Where aqueous base is used to effect this deprotection, the compound may be treated with an aqueous acid to liberate the free acid.

Compounds of general formula (Ia) may be prepared by processes analogous to those described herein commencing from a compound of formula (VIII) and a corresponding benzofuran intermediate.

The intermediate compounds of general formula (Ia) and their acid addition salts are novel compounds and form a further aspect of the present invention.

In another general process (D) a compound of general formula (I) in which the substituent R$^3$ in the group Ar represents —NHSO$_2$CF$_3$, may also be prepared from a compound of general formula (Ib)

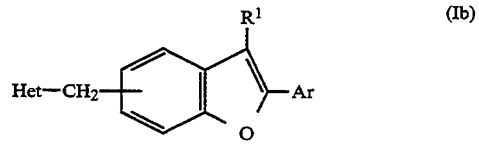
(Ib)

(wherein R$^1$ Ar and Het are as defined in general formula (I) except that in the group Ar, R$^3$ represents an amino group) by reaction with trifluoromethanesulphonic anhydride, in a suitable solvent such as dichloromethane.

Compounds of general formula (Ib) may be prepared by processes analogous to those described herein commencing from a compound of formula (IX) and a corresponding benzofuran intermediate.

Alternatively, compounds of general formula (Ib) may be prepared by a Curtius rearrangement of a compound of formula (I) wherein R$^3$ in the group Ar is —CO$_2$H (provided that this is the only carboxyl group in the molecule) using, for example, diphenylphosphorylazide in the presence of a base such as triethylamine and in a solvent such as an alcohol (e.g. tert-butanol) to form a carbamate followed by deprotection of the amine in a conventional manner, for example by acid hydrolysis using hydrochloric acid in a solvent such as ethanol.

The intermediate compounds of general formula (Ib) and their acid addition salts are novel compounds and form a further aspect of the present invention.

In the processes (A),(B), (C) and (D) described above, the compounds of general formula (I) may be obtained in the form of a salt, conveniently in the form of a physiologically acceptable salt. Where desired, such salts may be converted into the corresponding free acids or free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

The intermediate compounds of general formula (II) may be prepared from a compound of formula (V):

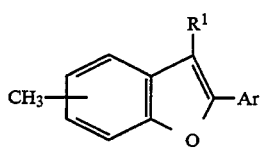
(V)

using any suitable reagent well known in the art for converting the methyl on the 6-membered ring into the group —CH$_2$L (wherein L is as defined above). Thus, for example, when L is a halogen atom, a compound of formula (V) can be conveted into a compound of general formula (II) using N-chloro amides, tert-butyl hypochlorite or N-bromosuccinimide. Halogenation of the side chain may be catalysed by light, thus the reaction can be illuminated with a suitable artificial light source, and preferably in the presence of a free radical initiator such as azobisisobutyronitrile (AIBN)or benzoyl peroxide.

Compounds of formula (V) wherein R$^1$ is a halogen atom, for example, a bromine atom, may be prepared by halogenation of a compound of formula (V) wherein R$^1$ represents a hydrogen atom, using for example, bromine, in a suitable solvent such as a halogenated hydrocarbon, e.g. carbon tetrachloride.

Compounds of formula (V) may be prepared by reaction of a compound of formula (VI)

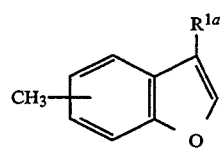
(VI)

(wherein R$^{1a}$ represents a hydrogen atom or a group selected from C$_{1-6}$alkyl or C$_{2-6}$alkenyl) with a compound of formula (VII)

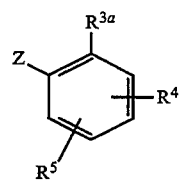
(VII)

(wherein Z represents a bromine or iodine atom or the group —OSO$_2$CF$_3$, R$^4$ and R$^5$ are as defined in general formula (I) and R$^{3a}$ is as defined for R$^3$ in general formula (I) or is a protected derivative thereof).

The compound of formula (VI) is first treated with an alkyl lithium compound such as n-butyl lithium at a reduced temperature, for example, between −100° C. and 0° C. in a solvent such as an ether (e.g. tetrahydrofuran). The mixture is then treated with a tri-alkylborate compound such as triisopropylborate and the temperature conveniently brought up to room temperature. Subsequently, water may be added and the mixture treated with a mineral acid such as sulphuric acid thus producing a compound of formula (VIa)

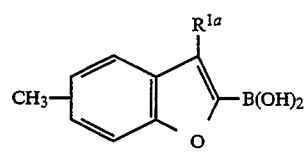
(VIa)

The intermediate compound of formula (VIa) is then reacted with a compound of formula (VII) in the presence of a palladium (0) compound such as tetrakis(triphenylphosphine) palladium (0) in a solvent such as an ether (e.g. dimethoxyethane), and in the presence of a base such as sodium carbonate or thallium hydroxide. The reaction is conveniently effected at an elevated temperature, such as the reflux temperature of the solvent.

Compounds of formula (V) in which the substituent R$^3$ in the group Ar represents a C-linked tetrazolyl group may be prepared from a precursor of a compound of formula (V) wherein the substituent R$^3$ represents a nitrile group using the reagents and conditions described in process (C).

Similarly, intermediates of formula (VII) wherein R$^{3a}$ represents a C-linked tetrazolyl group may be prepared from a compound of formula (VIII)

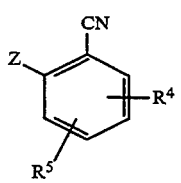
(VIII)

(followed where necessary by protection of any reactive groups), using methods well-known in the art such as those described in process (C).

Compounds of formula (V) in which the substituent R$^3$ in the group Ar is —NHSO$_2$CF$_3$ may be prepared from a precursor of a compound of formula (V) wherein the substituent R$^3$ is an amine group using the reagents and conditions described in process (D).

Similarly, intermediates of formula (VII) wherein $R^{3a}$ represents —NHSO$_2$CF$_3$ may be prepared from a compound of formula (IX),

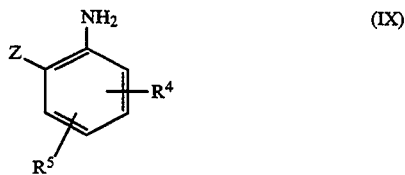

(followed where necessary by the protection of any reactive group) using methods well known in the art such as those described in process (D).

Compounds of formula (V) may also be prepared by an intramolecular cyclisation reaction of a compound of formula (X)

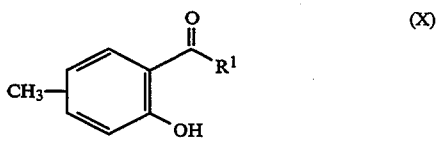

(wherein $R^1$ is as previously deemed) with a suitably substituted benzene of formula (XI)

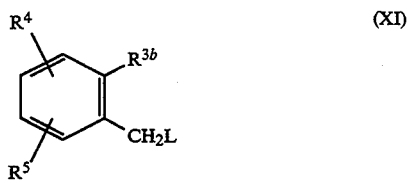

(wherein L is as previously defined and $R^{3b}$ is as defined for $R^{3a}$ in formula (VII) or is a nitrile group suitable for subsequent conversion into a tetrazolyl group or is an amino group suitable for conversion into —NHSO$_2$CF$_3$), in the presence of a base such as sodium hydride or potassium carbonate. The cyclisation is a two step reaction which requires one equivalent of base per step. It will be appreciated however that the reaction can be effected in the presence of two equivalents of base to avoid the need to isolate the intermediate. The reaction is conveniently effected in a solvent such as an ether e.g. tetrahydrofuran, an alcohol e.g. ethanol or a substituted amide e.g. dimethylformamide, at a temperature between room temperature and the reflux temperature of the solvent.

It will be appreciated that compounds of formula (V) in which $R^1$ represents a hydrogen or halogen atom may also be converted into compounds of formula (V) in which $R^1$ represents the group methyl (via hydrogenolysis of the Mannich base), —CHO or —COR$^2$ (wherein $R^2$ is as defined in general formula (I)) using techniques well known in the art, such as those described in "Heterocyclic Chemistry" by J. A. Joule and G. F. Smith, Van Nostrand Reinhold Company, London (1972), "Heterocyclic Chemistry" by A. Albert, 2nd Edition, The Athlone Press, London (1968), "Heterocyclic Compounds", Vol. 29 by A. Mustafa, John Wiley and Sons Inc., New York (1974), "Heterocyclic Compounds", Vol. 2 by R. C. Elderfield, John Wiley and Sons Inc., New York (1951 ) and "Advances in Heterocyclic Chemistry", Vol. 29 by A. R. Katritsky and A. J. Boulton, Academic Press, New York (1981).

The imidazoles of formula (III) may be prepared as described in European Specification No. 0253310A and in U.S. Pat. No. 4355040 or by methods analogous to those described therein. The content of these references is hereby incorporated by reference.

Intermediates of formulae (VI), (VII), (VIII), (IX), (X) and (XI), are either known compounds or may be prepared by methods analogous to those used for the preparation of the known compounds.

The following examples illustrate the invention. Temperatures are in 0° C. "Dried" refers to drying using magnesium sulphate. Thin layer chromatography (t.l.c.) was carried out over silica and column chromatography was carried out on silica (Merck 9385 unless otherwise stated), using one of the following solvent systems:A-ether:hexane, B-ether:dichloromethane, C-dichloromethane:ethanol:conc. aqueous ammonia, D-dichloromethane:ethyl acetate, or E-dichloromethane:ether:acetic acid. The following abbreviations are used: THF-tetrahydrofuran; DME-dimethoxyethane; AIBN -azobisisobutyronitrile; DMF-dimethylformamide; TMEDA-tetramethylethylenediamine; NBS-N-bromosuccinimide; DMAP-4-dimethylaminopyridine; DEAD-diethyl azodicarboxylate.

Intermediate 1

5-Methylbenzofuran-2-boronic acid n-Butyl lithium (35.16 ml) was added dropwise to a stirred solution of TMEDA (9.58 ml) and 5-methylbenzofuran (8.22 g) in ether (250 ml) maintaining the temperature below −60° C. throughout. The solution was warmed to about −10° C. over 45 minutes and stirred at this temperature for 30 minutes. A precipitate formed on warming. The suspension was cooled and triisopropylborate (43 ml) was added, maintaining the temperature below −60° C. The solution was warmed gradually to room temperature before quenching with 2N HCl (70 ml). The mixture was extracted with ether (3×50 ml) and the combined organic extracts washed with 2N HCl (4×30 ml), water (2×30 ml) and dried before evaporation to give the title compound as an orange solid (12.75 g).

t.l.c. System A (1:1), Rf0.3.

Intermediate 2

Methyl 2-(5-methyl-2-benzofuranyl)benzoate A solution of methyl 2-bromobenzoate (11.70 g), Intermediate 1 (12.75 g) and tetrakistriphenylphosphine palladium (0) (0.5 g) in DME (300 ml) and 2N Na$_2$CO$_3$ (60 ml) was heated to reflux with vigorous stirring under nitrogen. After 1.5 h a further 500 mg of catalyst was added and stirring at reflux under nitrogen continued. After about 5 h the reaction was cooled to room temperature and diluted with ether (300 ml). The organic layer was separated and washed with water (3×100 ml) and dried. Filtration and evaporation gave a yellow oily suspension (19.27 g) which was purified by chromatography eluting with System A (1:9) to give a yellow oil (11.06 g). This was further purified by Kugelrohr distillation to give the title compound (4.31 g).

t.l.c. System A (1:9), Rf 0.5.

Intermediate 3

Methyl 2-[5-(bromomethyl)-2-benzofuranyl]benzoate

A solution of Intermediate 2 (0.20 g) and NBS (0.098 g) in carbon tetrachloride (8 ml) was heated to reflux and irradiated with a 200 W tungsten bulb. After 1 h AIBN (10 mg) was added. After a further 30 minutes the solvent was evaporated to give a yellow crystalline solid which was purified by chromatography eluting with System A (1:9) to give the title compound (0.118 g).

t.l.c. System A (1:9), Rf 0.42.

Intermediate 4

Methyl 2-[5-[(2-butyl-1H-imidazol-1-yl)methyl]-2-benzofuranyl]benzoate

A solution on 2-butylimidazole (0.06 g) and sodium methoxide (0.02 g) in DMF (3 ml) was treated with a solution of Intermediate 3 (0.118 g) in DMF (3 ml). Stirring at room temperature was continued for 72 h. The solution was concentrated in vacuo and the residue dissolved in ether, washed with water (3×20 ml) and the combined aqueous phases back-extracted with ethyl acetate (20 ml). The combined organic phases were dried, filtered and evaporated to give an orange oil which was purified by chromatography eluting with System C (300:8:1) to give the rifle compound as a pale yellow oil (0.244 g).

t.l.c. System B (1: 1 ), Rf 0.2.

Intermediate 5

Methyl 2-(3-bromo-5-methyl-2-benzofuranyl)benzoate

A solution of Intermediate 2 (0.25 g) in carbon tetrachloride (5 ml) was cooled to −20° C. and treated dropwise with 1M bromine in carbon tetrachloride (0.7 ml). Stirring at −20° C. was then continued for 1 h before gradual warming to room temperature. Stirring at room temperature was continued overnight. Cyclohexene (0.1 ml) was added dropwise and the solvents were evaporated in vacuo to give the title compound as an orange oil (0.26 g).

t.l.c. System A (1:9), Rf 0.45.

Intermediate 6

Methyl 2-[3-bromo-5-(bromomethyl)-2-benzofuranyl]benzoate

A solution of Intermediate 5 (0.26 g) in carbon tetrachloride (8 ml) was treated with NBS (0.134 g) and AIBN (10 mg) according to the method of Intermediate 3 to give the title compound as a pale yellow oil (0.19 g).

t.l.c. System A (1:9), Rf 0.4.

Intermediate 7

Methyl 2-[3-bromo-5-[(2-butyl-1H-imidazol-1-yl)methyl]-2-benzofuranyl]benzoate

A solution of 2-butylimidazole (0.078 g) and sodium methoxide (0.025 g) in DMF (3 ml) was treated with a solution of Intermediate 6 (0.197 g) in DMF (3 ml) according to the method of Intermediate 4, to give the title compound as a yellow oil (0.143 g).

t.l.c. System B (1: 1 ), Rf 0.2.

Intermediate 8

2-(5-Methyl-2-benzofuranyl)benzonitrile

Intermediate 1 (20 g) was added to a stirred solution of 2-bromobenzonitrile (10.34 g) and tetrakistriphenylphosphine palladium (0) (1.5 g) in DME (200 ml) and 8% NaHCO₃ (50 ml) at reflux under nitrogen. Further catalyst (1.5 g) was added and the reaction continued overnight. The reaction was cooled to room temperature and diluted with ether (200 ml). The organic layer was separated, washed with water (3×100 ml) and dried. Filtration and evaporation gave a white solid which was purified by chromatography eluting with system A (1:9) to give the title compound (10.58 g) as a white solid.

T.l.c. System A (1:9), Rf 0.45.

Intermediate 8 was also prepared by the alternative two-step reaction a) 2-Hydroxy-5-methoxybenzaldehyde p-Cresol (100 g) in dry THF(100 ml) was added dropwise to a mechanically stirred, freshly prepared solution of ethyl magnesium bromide [magnesium (25.0 g) and bromoethane (75 ml)]in THF (500 ml) under nitrogen at a rate which maintained a slow reflux (about 30 mins). After a further 30 mins toluene (1.21) was added, followed by 1,3-dimethyl-3,4,5,6-tetrahydro-2(1H)-pyrimidone (125 ml), and paraformaldehyde (70 g). The mixture was then heated at reflux for 16 h. The mixture was concentrated by distillation and aqueous hydrochloric acid (2M, 600 ml) then added. Water (600 ml) was added and the mixture filtered through "hyflo". The organic phase was separated, dried, filtered and concentrated in vacuo to give a brown oil. The oil was steam distilled and the product extracted from the distillate with ether (1 liter). The organic extract was dried, filtered and concentrated in vacuo to give a pale yellow slurry which was cooled to −10° C., triturated with ether (precooled to −78° C., 100 ml), filtered off rapidly and washed with ether (precooled to −78° C.) to give the title compound as colourless needles, (131.4 g).

T.l.c. System A (1:5) Rf 0.5.

b) 2-(5-Methyl-2-benzofuranyl)benzonitrile

A solution of the product of step (a) (130 g) in dry DMF (400 ml) was added dropwise to a solution of sodium methoxide (56.2 g) in ethanol (400 ml) mechanically stirred under nitrogen. After a further 20 mins, a solution of 2(bromomethyl)benzonitrile (182.2 g) in dry DMF (400 ml) was added dropwise. The mixture was then heated to 75° C. for 30 mins. The solution was allowed to cool for 1 h. A slurry of sodium methoxide (56.2 g) in dry DMF (100 ml) was added and the mixture heated at reflux for 1.5 h. The mixture was concentrated in vacuo and then poured into iced water. The solid was collected, and then triturated with methanol to give the title compound (Intermediate 8) as a beige solid (149.4 g).

T.l.c. System A (1:9) Rf 0.4.

Intermediate 9

2-(3-Bromo-5-methyl-2-benzofuranyl)benzonitrile

A solution of Intermediate 8 (5.0 g) in dichloromethane (80 ml) was cooled to −20° C. and treated dropwise with 1M bromine in carbon tetrachloride (32 ml). The mixture was stirred at −20° C. for 1 h before being warmed to room temperature. After 1 h at room temperature the reaction mixture was filtered and evaporated. The residue was triturated with ether and the resultant solid collected to give the title compound as an orange solid (3.54 g).

T.l.c. System A (1:9), Rf 0.40.

Intermediate 10

2-[3-Bromo-5-(bromomethyl)-2-benzofuranyl]benzonitrile

A solution of Intermediate 9 (1.70 g) and NBS (0.76 g) in carbon tetrachloride (30 ml) was heated to reflux under nitrogen with benzoyl peroxide (0.08 g). After 18 h the reaction was cooled to room temperature, filtered and the concentrated in vacuo. The residue was triturated with ether to give the title compound as a colourless solid (0.58 g).

T.l.c. System A (1:6), Rf 0.25.

Intermediate 11

2-[3-Bromo-5-[[2-butyl-4-chloro-5-(hydroxymethyl)-1H-imidazol-1yl]methyl-2-benzofuranyl]benzonitrile A solution of 2-butyl-4-chloro-1H-imidazole-5-methanol (1.23 g) and sodium methoxide (0.24 g) in DMF (10 ml) was treated with Intermediate 10 (1.7 g) according to the method of Intermediate 4. Purification by chromatography eluting with system D (4:1) to give the title compound (0.57 g).

T.l.c. System D (4:1), Rf 0.45.

Intermediate 12

5-[2-(5-Methyl-2-benzofuranyl)phenyl]-1H-tetrazole

A suspension of Intermediate 8 (94 g) in tri-n-butyl tin azide (268 g) was heated at 100°–125° C. for 1.25 h under nitrogen. The resulting solution was then heated at 155°–160° C. for 2 h under nitrogen, then poured into a solution of aqueous sodium hydroxide (0.8N, 3070 ml). This solution was extracted with ether. The aqueous phase was acidified to pH1 with 5N hydrochloric acid and the resulting precipitate filtered, washed with water and dried under vacuum. The solid was dissolved in ethyl acetate, washed with brine and dried. The solvent was evaporated to give the title compound as a buff-coloured solid (100.3 g).

T.l.c. SystemA (1:1),Rf 0.2.

Intermediate 13

5-[2-(3-Bromo-5-methyl-2-benzofuranyl)phenyl]-1H-tetrazole

A solution of bromine (58 g), in carbon tetrachloride (140 ml) was added dropwise over 35 mins to a mechanically stirred solution of Intermediate 12 (50 g) in dry dioxan (2090 ml) at room temperature under nitrogen. The resulting solution was stirred at room temperature for 3 h, then cyclohexene (63 ml) was added. Another preparation of the product was carried out simultaneously on the same scale as described above, and at this stage they were combined. The solvent was evaporated and the residual brown oil (260 g) partitioned between ether and aqueous sodium hydroxide. The alkaline solution was acidified to pH1 with hydrochloric acid, then extracted with ethyl acetate. The combined ethyl acetate extracts were washed with brine, dried and evaporated to give a buff solid (125 g) which was triturated under hot toluene, cooled and filtered off to give the title compound as a cream coloured solid (101.8 g).

T.l.c. Ether/petroleum ether/acetic acid (50:50:1), Rf 0.27.

Intermediate 14

5-[2-(3-Bromo-5-methyl-2-benzofuranyl)phenyl]-2-(triphenylmethyl)-2H-tetrazole

Triethylamine (57.4 g) was added to a mechanically stirred suspension of Intermediate 13 (101 g) in dry dichloromethane (2.9 liters) at room temperature under nitrogen. Triphenylmethyl chloride (79.3 g) followed by DMAP (1.0 g) were added at room temperature and the mixture stirred for 3 h under nitrogen. The reaction mixture was washed with water, then brine and dried. The solvent was filtered and concentrated to a volume of about 1.2 liters then filtered through silica (Merck 9385, 14 cm diam. column). Elution with dichloromethane gave a colourless solid (158.4 g) which was triturated with ether and filtered to give the title compound as a colourless solid (147.9 g).

T.l.c. (Dichloromethane/hexane 1:1 ), Rf 0.28

Intermediate 15

5-[2-[3-Bromo-5-(bromomethyl)-2-benzofuranyl]-phenyl]-2-(triphenylmethyl)-2H-tetrazole Intermediate 14 (74 g) was dissolved in carbon tetrachloride (2050 ml) by heating the suspension to reflux. The resulting colourless solution was allowed to cool to 50° C. then NBS (22.1 g) was added, followed by benzoyl peroxide (1.1 g). The reaction mixture was heated at reflux for 3.25 h, under nitrogen, then allowed to cool to room temperature. The reaction mixture was washed with water then brine. Another preparation of the product was carried out simultaneously on the same scale as described above, and at this stage they were combined and dried. The solvent was evaporated to give a colourless solid (168 g) which was triturated with ether/methanol (1:1) and filtered to give the title compound as a colourless solid (160.8 g).

T.l.c. (Dichloromethane/hexane 1:1), Rf 0.15.

Intermediate 16

2-Butyl-4-chloro-1H-imidazole-5-carboxaldehyde

A suspension of 2-butyl-4-chloro-1H-imidazole-5-methanol (22.0 g) in dichloromethane:1,4-dioxan (2:1) (690 ml) was treated with manganese dioxide (63.15 g) and the reaction mixture heated at reflux under nitrogen for 3.5 h. The reaction mixture was cooled, filtered and the filtrate evaporated to leave an off-white solid. The residue was triturated with petroleum ether, filtered and dried to give the title compound as a white solid (17.9 g) m.p. 98°–99° C.

Intermediate 17

1[[3-Bromo-2[2-[2-(triphenylmethyl)-2H-tetrazol-5-yl]phenyl]-5-benzofuranyl]methyl]-2-butyl-4-chloro-1H-imidazole-5-carboxaldehyde A mixture of Intermediate 16 (500 mg), Intermediate 15(2.73 g) and potassium carbonate (407 mg) in dry DMF (20 ml) was heated at 80° C. for 24 h. A further quantity of Intermediate 15 (500 mg) was added and heating continued for 18 h. The reaction mixture was cooled, poured into water (200 ml) and extracted with ethyl acetate. The organic extracts were combined, dried and concentrated in vacuo to a yellow foam (3.6 g). This was purified by chromatography, eluting with petroleum ether/ether 3:1, 1:1 and then ether to give the title compound (1.78 g) as a pale yellow foam.

T.l.c. System A (1:3) Rf 0.28.

Intermediate 18

1-[[3-Bromo-2-2-[2-(triphenylmethyl)-2H-tetrazol-5-yl]phenyl]-5-benzofuranyl]methyl]-2-butyl-4-chloro-1H-imidazole-5-carboxylic acid A solution of sodium chlorite (3.39 g) and sodium dihydrogen phosphate (3.39 g) in water (40 ml), was added to a mixture of Intermediate 17 (2.93 g) in tert-butanol (50 ml) and 2-methyl-2-butene (2M in THF, 22.5 ml) and THF (50 ml). The mixture was stirred overnight at room temperature after which time most of the solvent was removed in vacuo and the residue partitioned between water (containing 2N sodium hydroxide solution to about pH 12) and ether. The aqueous layer was neutralised with saturated ammonium chloride solution and extracted with ethyl acetate. The organic extracts were combined, backwashed with water and brine, dried and concentrated in vacuo to give the title compound as a white solid (2.95 g).

T.l.c. dichloromethane/methanol (10:1), Rf 0.58.

Intermediate 19

5-[2-[3-Bromo-5-[(2-butyl-1H-imidazol-1-yl)methyl]-2-benzofuranyl]phenyl]-2-(triphenylmethyl)-2H-tetrazole Sodium methoxide (400 mg) was added to a solution of 2-butyl-1H-imidazole (400 mg) in dry DMF (40 ml) and the mixture stirred for 30 minutes. Intermediate 15 (2.2 g) was then added and the reaction progressed according to the method of Intermediate 4. Purification by chromatography (ethyl acetate) gave the title compound as a white solid (1.4 g).

T.l.c. ethyl acetate Rf=0.4.

Intermediate 20

2-[5-(Bromomethyl)-2-benzofuranyl]benzonitrile

A solution of Intermediate 8 (1.0 g) in carbon tetrachloride (40 ml) was treated with NBS (0.771 g) and AIBN, (0.14 g) according to the method of Intermediate 3 to give the title compound as an off-white crystalline solid (1.20 g)

T.l.c System A (1:9) Rf 0.35.

Intermediate 21

2-[5-[[2-Butyl-4-chloro-5-(hydroxymethyl)-1H-imidazol-1yl]methyl]-2-benzofuran]benzonitrile A solution of Intermediate 20 (0.70 g) in dry DMF (5 ml) and sodium methoxide (0.17 g) was treated with 2-butyl-4-chloro-1H-imidazole-5-methanol (1.15 g) as a solution in DMF (5 ml) according to the method of Intermediate 4. Purification by chromatography, eluting with System D (2:1) gave the title compound as an off-white solid (0.272 g)

T.l.c. System D (2:1) Rf 0.5.

Intermediate 22

Methyl 2-[3-bromo-5-[2-butyl-4-chloro-5-(hydroxymethyl)-1H-imidazol-1-yl]-2-benzofuranyl]benzoate Sodium methoxide (113 mg) in a stirred solution of 2-butyl-4-chloro-1H-imidazole-5-methanol (358 mg) in dry DMF (10 ml) was treated with Intermediate 6 (1.0 g) according to the method of Intermediate 4. Purification by chromatography eluting with ether followed by ether/ethanol (10:1) gave the title compound as a pale yellow solid (306 mg).

T.l.c. ether, Rf 0.55.

Intermediate 23

2-(3,5-Dimethyl-2-benzofuranyl)benzonitrile

A solution of 1-(2-hydroxy-5-methylphenyl)ethanone (1 g) in DMF (7 ml) was added to a solution of sodium methoxide (0.39 g) in ethanol (7 ml). After about 10 min a solution of 2-(bromomethyl)benzonitrile (1.3 g) in DMF (7 ml) was added and the solution heated to 110° C. After 2 h further sodium methoxide (0.39 g) was added and heating at 110° C. continued. After a further 30 min, the reaction was cooled to room temperature and the ethanol evaporated. The solution was poured into water/ice (200 ml) and extracted into ethyl acetate (4×30 ml). The combined organic extracts were washed with water (4×20 ml) and dried. Filtration and evaporation gave a yellow oil which was then dissolved in dichloromethane (2 ml) and methanol (30 ml). Concentration gave a solid which was collected and washed with further methanol to give the title compound as a white solid (0.53 g).

Assay Found: C,82.3; H,5.1; N,5.4. $C_{17}H_{13}NO$ requires: C,82.6; H,5.3; N,5.6%.

Intermediate 24

5-[(3,5-Dimethyl-2-benzofuranyl)phenyl]-1H-tetrazole

Intermediate 23 (0.27 g) was added to tri-n-butyl tin azide (3 g) with stirring at 160° C. under nitrogen and treated according to the method of Intermediate 12 to give the title compound as a white foam (0.315 g).

Assay Found: C,70.5; H,4.9; N,19.55. $C_{17}H_{14}N_4O$ requires: C,70.3; H,4.9; N, 19.3%

Intermediate 25

5-[(3,5-Dimethyl-2-benzofuranyl)phenyl]2-(triphenylmethyl)-2H-tetrazole

A solution of Intermediate 24 (0.3 g) in dry dichloromethane (10 ml) was treated with triethylamine (0.33 ml), triphenylmethyl chloride (0.2 g) and DMAP (~10 mg). Stirring at room temperature was continued overnight. The reaction mixture was diluted with dichloromethane (20 ml) and washed with water (3×20 ml). The combined organic extracts were dried, filtered and evaporated to give a buff solid (0.78 g) which was purified by chromatography eluting with dichloromethane:hexane (1:1) to give the title compound as a white solid (0.43 g).

T.l.c. dichloromethane:hexane (1:1) Rf 0.25.

Intermediate 26

5-[2-[5-[[2-Butyl-4-chloro-5-(hydroxymethyl)-1H-imidazol-1-yl]methyl]-3-methyl-2-benzofuranyl]-phenyl]-2-(triphenylmethyl)-2H-tetrazole A solution of Intermediate 25 (6.10 g) in carbon tetrachloride (175 ml) was treated with NBS (2.14 g) and AIBN (0.35 g) and then heated to reflux whilst irradiating with a 250 W tungsten bulb. After 0.5 h, the mixture was filtered and washed with water (3×100 ml), dried, filtered and evaporated to give a white foam. A solution of 2-butyl-4-chloro-1H-imidazole-5-methanol (3.24 g) in dry DMF (30 ml) was treated with sodium methoxide (0.93 g) and stirred under nitrogen for about 15 min. A solution of the brominated materials in dry DMF (80 ml) was then added and stirring at room temperature continued for 16 h. The solvent was evaporated and the residue dissolved in ethyl acetate (250 ml) and washed with water (3×100 ml), dried, filtered and evaporated to give an orange oil which was purified by chromatography, eluting with System C (300:8:1) to give a yellow foam. This was further purified by chromatography in ether and then by chromatography eluting with System A (2:1) to give the title compound (0.63 g) as a yellow foam.

T.l.c. ether Rf 0.45

Intermediate 27

2-(3-Methoxy-5-methyl-2-benzofuranyl)benzonitrile 2-(Bromomethyl)benzonitrile (17.6 g) was added to a mixture of methyl 2-hydroxy-5-methylbenzoate (15 g) and sodium hydride (2.7 g, 80% dispersion in oil) in dry THF (150 ml) and the resulting mixture heated at reflux for 5 h. Further sodium hydride (2.7 g, 80% dispersion in oil) was added and heating continued overnight. The mixture was cooled (0° C.), sodium hydride (2.7 g, 80% dispersion in oil) and dimethyl sulphate (17 ml) were added, and the resulting solution stirred at room temperature for 4 h. Solvent was removed in vacuo, the residue taken up in dichloromethane (200 ml) and conc. ammonia solution (200 ml) added carefully. The organic solution was removed and the aqueous solution extracted with dichloromethane (2×200 ml). The combined, dried organic phases were evaporated in vacuo and the residue purified by chromatography, eluting with dichloromethane: hexane (1:1) to give the title compound as a white solid (17 g).

T.l.c. dichloromethane:hexane (1:1) Rf 0.3.

Intermediate 28

2-[5-(Bromomethyl)-3-methoxy-2-benzofuranyl]benzonitrile

A mixture of Intermediate 27 (0.39 g),NBS (0.33 g) and AIBN (100 mg) in carbon tetrachloride (15 ml) was heated at reflux for 4 h. The mixture was filtered and the solvent removed in vacuo to give the title compound as a yellow oil (0.52 g).

T.l.c. dichloromethane:hexane (1:1) Rf 0.35.

Intermediate 29

2-[5-[[2-Butyl-4-chloro-5-(hydroxymethyl)-1H-imidazol-1-yl]methyl]-3-methoxy-2-benzofuranyl]benzonitrile Intermediate 28 (0.52 g) was added to a mixture of 2-butyl-4-chloro-1H-imidazole-5-methanol (0.29 g) and sodium methoxide (81 mg) in DMF (10 ml) and the resulting mixture treated according to the method of Intermediate 4 Purification by chromatography eluting with ether gave the title compound as an off-white solid (0.25 g), m.p. 164°-168° C.

Intermediate 30

Methyl 1-[[3-bromo-2-[2-[2-(triphenylmethyl)-2H-tetrazol-5-yl]phenyl]-5-benzofuranyl]methyl]-2-butyl-4-chloro-1H-imidazole-5-carboxylate To a solution of Intermediate 18 (500 mg) in THF (5 ml) was added diazomethane in ether (0.7 ml). Excess diazomethane was destroyed with acetic acid and the remaining solution concentrated to dryness. This was purified by chromatography, eluting with dichloromethane/methanol (500:1) to give the title compound (357 mg) as a white foam.

T.l.c. dichloromethane/methanol (50:1), Rf 0.72.

Intermediate 31

Ethyl 1-[[3-bromo-2-[2-[2-(triphenylmethyl)-2H-tetrazol-5-yl]phenyl]-5-benzofuranyl]methyl]-2-butyl-4-chloro-1H-imidazole-5-carboxylate A mixture of Intermediate 18 (0.5 g) and 1,1'-carbonyldiimidazole (112 mg) in dry THF (10 ml) was allowed to stir at room temperature for 3 h. Ethanol (0.36 ml) was added to the reaction mixture which was subsequently heated at 70° C. for 24 h. Ethanol (3.6 ml) was added and heating continued for 6 h. The reaction mixture was allowed to cool to room temperature, concentrated in vacuo and then purified by chromatography, eluting with dichloromethane/methanol (500:1) to give the title compound as a white foam (508 mg).

T.l.c. dichloromethane/methanol (50:1), Rf 0.86.

Intermediate 32

Butyl 1-[[3-bromo-2-[2-[2-(triphenylmethyl)-2H-tetrazol-5-yl]phenyl]-5-benzofuranyl]methyl]-2-butyl-4-chloro-1H-imidazole-5-carboxylate A solution of DEAD (120 mg) in dry THF (5 ml) was added dropwise to a solution of Intermediate 18 (0.5 g), triphenylphosphine (181 mg) and n-butanol (0.09 ml) in dry THF (5 ml). The reaction mixture was stirred at room temperature for 3 h, after which time n-butanol (0.09 ml) was added and stirring continued for 1 h. Triphenylphosphine (82 mg) was added to the reaction mixture, followed by the further addition of DEAD (0.05 ml) in dry THF (3 ml) dropwise. Stirring was continued overnight and then the reaction mixture was concentrated in vacuo. The residue was purified by chromatography, eluting with dichloromethane/methanol (500:1) to give the title compound (484 mg) as a white foam.

T.l.c. dichloromethane/methanol (500:1) Rf 0.49.

Intermediate 33

Ethyl 1-[[3-bromo-2-[2-[2-(triphenylmethyl)-2H-tetrazol-5-yl]phenyl]-5-benzofuranyl]methyl-2-(1-bromobutyl)-4-chloro-1H-imidazole-5-carboxylate A mixture of Intermediate 31 (500 mg) and NBS (107 mg) in carbon tetrachloride (200 ml) was irradiated (UV lamp, 125 W, pyrex filter) at room temperature for 1 h and then the solvent was removed in vacuo. The product was purified by chromatography eluting with petroleum ether:ether (3:1) to afford the title compound (270 mg) as an-off white powder.

T.l.c petroleum ether:ether (1:1) Rf 0.67

Intermediate 34

Ethyl 1-[[3-bromo-2-[2-[2-(triphenylmethyl)-2H-tetrazol-5-yl]phenyl]-5-benzofuranyl]methyl-2-but-1(E)-enyl-4-chloro-1H-imidazole-5-carboxylate To a solution of Intermediate 33 (220 mg) in THF (5 ml) was added 1,8-diazabicyclo[5.4.0]undec-7-ene (73 μl) and the resultant solution stirred at room temperature for 72 h. The reaction mixture was concentrated in vacuo and purified by chromatography eluting with petroleum ether:ether (3:1) to afford the title compound (115 mg) as a white solid.

T.l.c. Petroleum ether:ether (3:1) Rf 0.33

Intermediate 35

1-[[3-Bromo-2-[2-[2-(triphenylmethyl)-2H-tetrazol-5-yl]phenyl]5-benzofuranyl]methyl]-4-chloro -2-propyl-1H-imidazole-5-carboxaldehyde.

A mixture of Intermediate 15 (3.1 g),4-chloro-2-propyl-1H-imidazole-5carboxaldehyde (660 mg) and potassium carbonate (700 mg) in DMF (60 ml) was treated according to the method of Intermediate 17. Trituration with ether gave a cream solid which was recrystallised from ethyl acetate to give the title compound as a white powder (1.36 g).

T.l.c. (ether) Rf=0.74.

Intermediate 36

1-[[3-Bromo-2-[2-[2-(triphenylmethyl)-2H-tetrazol-5-yl]phenyl]-5-benzofuranyl]methyl]-4-chloro-2-propyl-1H-imidazole-5-carboxylic acid A solution of sodium chlorite (565 mg) and sodium dihydrogen phosphate (593 mg) in water (10 ml) was added to a mixture of Intermediate 35 (500 mg) in tert-butanol (8 ml) and 2-methyl-2-butene (2M in THF, 4 ml) and THF (10 ml). The mixture was allowed to stir at room temperature overnight. The solvents were removed in vacuo and the residue partitioned between ether and 0.25M sodium hydroxide solution. The ether layer was separated and discarded. The aqueous sodium hydroxide phase was neutralised with saturated ammonium chloride solution and then extracted with ethyl acetate. The combined ethyl acetate extracts were washed with water, brine, dried and concentrated to give the title compound as a white solid (472 mg).

T.l.c. (ether) Rf=0.67.

Intermediate 37

2-Butylimidazole-4,5-dicarboxylic acid

To a suspension of tartaric acid (15 g) in concentrated nitric acid (32.4 ml) was added fuming nitric acid (32.4 ml) and the resultant suspension stirred at room temperature for 30 mins. Concentrated sulphuric acid was added at a rate to maintain a temperature at about 40° C. The precipitate was cooled to 10° C. and allowed to stand for 30 mins. The solid was collected, dried and transferred in portions to finely cracked ice (300 g). The resultant mixture was then poured into a flask at −12° C. and concentrated ammonium hydroxide (ca. 40 ml) was added dropwise to neutrality ensuring the temperature did not exceed −5° C. Further concentrated ammonium hydroxide (30 ml) was added followed by pentanal (8.61 g). The solution was stirred at 0° C. for 5½ h and was then allowed to stand at room temperature for 30 mins. The reaction mixture was cooled to 0° C. and concentrated HCl was added to pH 5 and the solids removed by filtration. Drying gave the title compound (12.2 g) as a pale yellow solid.

n.m.r. δ(250 MHz, DMSO) 0.88 (3H,t), 1.27 (2H, sex), 1.61 (2H,quin), 2.6 (2H,t).

Intermediate 38

Diethyl 2-butylimidazole-4,5-dicarboxylate

Acetylchloride (20.1 ml) was added dropwise over 10 mins to a mixture of Intermediate 37 (10.0 g) in ethanol (200 ml) and the resultant mixture heated at reflux for 23 h. The reaction mixture was concentrated in vacuo and the residue dissolved in water (100 ml) and the pH adjusted to pH 7.5 (8% $Na_2CO_3$). The aqueous phase was extracted into ethyl acetate (3×100 ml) and the combined organic phases dried and concentrated in vacuo to afford the title compound as a yellow solid (7.81 g).

n.m.r δ(250 MHz, CDCl$_3$) 0.90 (3H,t), 1.31 (2H,sex), 1.38 (6H,t), 2.79 (2H,t), 4.4 (4H,q), 10.7 (1H,br).

Intermediate 39

2,2,2-Trifluoro-1-(2-hydroxy-5-methylphenyl)ethanone

A solution of 2-bromo-4-methylphenol (35 g) in dry ether (300 ml) was cooled in an ice bath and treated dropwise with n-butyl lithium (227 ml) under nitrogen maintaining the temperature below 5° C. Following completion of addition the reaction was warmed to room temperature. Stirring at this temperature was continued for ~2 h. The solution was cooled to about −60° C. and treated dropwise with freshly distilled trifluoroacetic anhydride (26.2 ml). The resulting solution was stirred at low temperature for a further 1 h before warming to room temperature. Stirring at this temperature was continued overnight. The resulting reaction mixture was washed with saturated aqueous ammonium chloride (3×150 ml) and the organic phases dried. The remaining ether was removed by evaporation at atmospheric pressure on a rotary evaporator. The resulting solution was purified by column chromatography eluting with hexane to give the title compound as a yellow/orange crystalline solid (13.12 g).

T.l.c. Hexane, Rf 0.5

Intermediate 40

[2-(2,2,2-Trifluoro-1-oxoethyl)-4-methyl]phenoxy-2-methylbenzonitrile

A solution of Intermediate 39 (2.23 g) in dry DMF (20 ml) was stirred under nitrogen and treated with sodium hydride (0.361 g). The solution was stirred at room temperature for about 15 mins before addition of 2-(bromomethyl)benzonitrile (2.14 g). Stirring at room temperature was continued for 1 h. The material was poured into water (100 ml) and extracted into ether (3×50 ml). The combined organic phases were washed with water (3×30 ml), dried, filtered and evaporated to give a yellow oil (3.22 g). Purification by column chromatography eluting with System A (1:9) gave the title compound as a white solid (1.84 g).

T.l.c. System A (1:9) Rf 0.3

Intermediate 41

2-5-Methyl-3-(trifluoromethyl)-2-benzofuranyl]benzonitrile

A solution of Intermediate 40 (0.157 g) in dry DMF (6 ml) was stirred under nitrogen and treated with sodium hydride (80% in oil; 0.015 g). Stirring was continued at about 90° C. overnight. The reaction mixture was cooled to room temperature and poured into water (70 ml). The resulting suspension was extracted into ethyl acetate (4×20 ml), and dichloromethane (20 ml) and the combined organic phases washed with water (3×20 ml). The organic phases were dried, filtered and evaporated to give an orange oil (0.23 g). Purification by column chromatography eluting with System A (1:9) gave the title compound as an off-white powdered solid (0.015 g).

T.l.c. System A (1:9) Rf 0.45

Intermediate 42

5-[2-[5-Methyl-3-(trifluoromethyl)-2-benzofuranyl]-phenyl]-1H-tetrazole

A suspension of Intermediate 41 (0.548 g) in tri-n-butyl tin azide (1.5 g) was heated to ~150° C. After 1 h the solution was cooled to room temperature and the residue dissolved in 2N NaOH. The resulting solution was washed in ether (4×20 ml) before acidification to about pH2. A suspension formed which was extracted into ethyl acetate (4×25 ml) and the combined organic phases dried, filtered and evaporated to give the title compound as an off-white foam (0.635 g).

n.m.r. δ(CDCl$_3$+DMSO+base) 8.01 (1H,broad d), 7.6–7.55 (3H,m), 7.45 (1H,d), 7.3 (1H,d), 7.2 (1H,d), 2.45 (3H,s).

Intermediate 43

5-[2-[5-Methyl-3-(trifluormethyl)-2-benzofuranyl]-phenyl]-2-(triphenylmethyl)-2-H-tetrazole

A solution of Intermediate 42 (1.17 g) in dry dichloromethane (50 ml) was treated with chlorotriphenylmethane (1.05 g), triethylamine (10.86 ml) and DMAP (~250 mg). The resulting solution was stirred at room temperature overnight under nitrogen. The solution was diluted with dichloromethane (50 ml) before washing with water (3×25 ml). The organic phase was dried, filtered and evaporated to give a pale yellow solid. Purification by column chromatography eluting with dichloromethane:hexane (1:1) gave the title compound as a pale yellow solid, (1.63 g).

T.l.c dichlomethane:hexane (1:1) Rf 0.45

Intermediate 44

5-[2-[5-(Bromomethyl)-3-(trifluoromethyl)-2-benzofuranyl]phenyl]-2-(triphenylmethyl)-2H-tetrazole

A solution of Intermediate 43 (0.963 g) in carbon tetrachloride (30 ml) was treated with NBS (0.325 g) and AIBN (~100 mg) according to the method of Intermediate 3 to give the title compound as an orange/yellow solid (1.13 g).

T.l.c. dichloromethanne:hexane (1:1) Rf 0.45

Intermediate 45

2-Butyl-4-chloro-1-[[3-(trifluoromethyl)-2-[[2-(triphenylmethyl)-2H-tetrazol-5-yl]phenyl]-5-benzofuranyl]methyl]-1H-imidazole-5-carboxaldehyde A mixture of Intermediate 16 (0.186 g), Intermediate 44 (0,665 g) and potassium carbonate (0.145 g) in DMF was treated according to the method of Intermediate 17. Purification by column chromatography eluting with System A (1:1) gave the title compound as a white foam (0.48 g).

T.l.c. System A (1:1) Rf0.3

Intermediate 46

2-Butyl-4-chloro-1-[[3-(trifluoromethyl)-2-[[2-(triphenylmethyl)-2H-tetrazol-5-yl]phenyl]5-benzofuranyl]methyl]-1H-imidazole-5-carboxylic acid A solution of sodium chlorite (0.552 g) and sodium dihydrogen phosphate (0.552 g) in water (5 ml) was added to a mixture of the Intermediate 45 (0.47 g) in tert-butanol (10 ml), 2 methyl-2-butene (2M in THF; 3.66 ml) and THF (10 ml) and the reaction mixture treated according to the method of Intermediate 36 to yield the title compound as a white foam (0.504 g).

T.l.c. ether, Streak Rf 0.5

Intermediate 47

3-Bromo-2-(bromomethyl)benzonitrile

A mixture of NBS (3.45 g), dibenzoyl peroxide (100 mg) and 3-bromo-2-methylbenzonitrile (3.47 g) in carbon tetrachloride (40 ml) was heated at reflux under nitrogen for 48 h. The mixture was then cooled to room temperature, filtered and concentrated in vacuo to give a pale yellow solid. Chromatography eluting with dichloromethane gave the title compound as a white solid (4.23 g) m.p. 90°–93° C.

Intermediate 48

3-Bromo-2-(5-methyl-2-benzofuranyl)benzonitrile

A solution of 2-hydroxy-5-methylbenzaldehyde (2.00 g) and sodium methoxide (0.854 g) in dry DMF (20 ml) was added to a solution of Intermediate 47 (4.17 g) in dry DMF (10 ml) with the mixture stirred at room temperature for 1 h. Sodium methoxide (0.854 g) was added and the solution heated at 100° C. for 2 h. The solution was concentrated in vacuo before adding ethyl acetate (50 ml) and washing with water (2×100 ml). The organic phase was dried, filtered and concentrated in vacuo to give an oil. Chromatography eluting with System A (1:10) gave the title compound as a pale yellow oil (1.18 g).

T.l.c. System A (1:9), Rf 0.35

Intermediate 49

3-Bromo-2-[5-[[2-butyl-4-chloro-5-(formyl)-1H-imidazol-1-yl]methyl]-2-benzofuranyl]benzonitrile A mixture of Intermediate 48 (1.16 g), NBS (0.727 g) and AIBN (200 mg) was heated at reflux in carbon tetrachloride (20 ml) under nitrogen whilst irradiating with a 150 W lamp for 2 h. The mixture was cooled to room temperature, filtered and concentrated in vacuo to give a yellow oil. Dichloromethane (100 ml) was added and the solution washed with water (10 ml), dried, filtered and concentrated in vacuo to give a yellow oil. A mixture of the oil, Intermediate 16 (0.700 g) and potassium carbonate (0.70 g) in dry DMF (20 ml) was heated at 80° C. under nitrogen for 16 h. The mixture was concentrated in vacuo, ethyl acetate (40 ml) added and the mixture then washed with water (2×50 ml),followed by saturated ammonium chloride (10 ml), dried, filtered and concentrated in vacuo to give a brown oil. Chromatography eluting with System A (2:3) gave the title compound as a pale yellow oil (1.07 g).

T.l.c. System A (1:1) Rf0.4

Intermediate 50

1-[[2-(2-Bromo-6-cyanophenyl)-5-benzofuranyl]methyl]-2-butyl-4-chloro-1H-imidazole-5-carboxylic acid A mixture of sodium chlorite (1.51 g) and sodium dihydrogenphosphate (1.55 g) in water (15 ml) was added to a vigorously stirred mixture of Intermediate 49 (1.06 g) and 2-methylbut-2-ene (2M in THF; 9.5 ml) in THF (20 ml) and tert-butanol (20 ml) and the reaction mixture treated according to the method of Intermediate 36 to give the title compound as a pale yellow foam (1.08 g).

T.l.c. ether, Rf 0.3

Intermediate 51

1-(Acetoxy)methyl 1-[[3-bromo-2-[2-(triphenylmethyl)-2H-tetrazol-5-yl]phenyl]-5-benzofuranyl]methyl]-2-butyl-4-chloro-1H-imidazole-5-carboxylate A mixture of Intermediate 18 (2.14 g) and potassium carbonate (370 mg) in DMF (30 ml) was stirred for 20 minutes. Bromomethyl acetate (410 mg) was added and the reaction mixture stirred for 24 h. The reaction mixture was poured into water and extracted with ethyl acetate. The combined organic extracts were washed with water, brine, dried and concentrated to give the title compound as a white foam (2.3 g).

T.l.c. (Ether). Rf=0.5.

Similarly prepared

Intermediate 52

1-[[3-Bromo-2-[2-[2-(triphenylmethyl)-2H-tetrazol-5-yl]phenyl]-5-benzofuranyl]methyl]-2-butyl-4-chloro-1H-imidazole-5-carboxylic acid, (acetyloxy)ethyl ester as a white foam (2.1 g). T.l.c. (ether) Rf=0.8

From Intermediate 18 (2.07 g) and potassium carbonate (358 mg) in DMF (30 ml). 1-Bromoethyl acetate (433 mg) was added; reaction time 3 hours.

Intermediate 53

Benzoyloxymethyl 1-[[3-bromo-2-[2-(triphenylmethyl)-2H-tetrazol-5-yl]phenyl]-5-benzofuranyl]methyl]-2-butyl-4-chloro-1H-imidazole-5-carboxylate as a white foam (2.07 g).

Assay Found: C,65.3; H,4.3; N,8.6; $C_{50}H_{42}BrClN_6O_5$ requires C,65.1; H,4.6; N,9.1%

From Intermediate 18 (2 g) in DMF(25 ml) and potassium carbonate (0.35 g). Chloromethylbenzoate (0.43 g) was added; reaction time 20 hours. Purification by column chromatography eluting with ethyl acetate afforded the title compound.

Intermediate 54

1-(Ethoxycarbonyloxy)ethyl 1-[[3-bromo-2-[2-[2-(triphenylmethyl)-2H-tetrazol-5-yl]phenyl]-5-benzofuranyl]methyl]-2-butyl-4-chloro-1H-imidazole-5-carboxylate as a white foam (1.87 g).

Assay Found: C,62.9; H,4.7; N,8.9; Br, 8.7; Cl,3.9; $C_{48}H_{42}BrClN_6O_6$ requires C,63.1; H,4.6; N,9.2; Br, 8.7; Cl,3.8%

From Intermediate 18 (2 g) in DMF (25 ml) and potassium carbonate (0.35 g). 1-Chloroethyl ethyl carbonate (0.38 g) was added; reaction time 3 days after addition of further potassium carbonate (0.19 g). Purification by column chromatography eluting with ether afforded the title compound.

Intermediate 55

[4-(Aminocarbonyl)phenyl]methyl 1-[[3-bromo-2-[2-[2-(triphenylmethyl)-2-H-tetrazol-5-yl]phenyl]-5-benzofuranyl]methyl]-2-butyl-4-chloro-1H-imidazole-5-carboxylate as a white solid (300 mg). mp 105°–107°.

From Intermediate 18 (2 g) in DMF (20 ml) and potassium carbonate (0.35 g). 4-Bromomethylbenzamide (0.38 g) was added; reaction time 60 hours. Purification by chromatography eluting with System C (200:8:1) afforded the title compound.

Intermediate 56

2-(N,N-dimethylaminoethyl)1-[[3-bromo-2-[2-[2-(triphenylmethyl)-2H-tetrazol-5-yl]phenyl]-5-benzofuranyl]methyl]-2-butyl-4-chloro-1H-imidazole-5-carboxylate A solution of DEAD (0.75 ml) in dry THF (5 ml) was added to a solution of Intermediate 18 (2.02 g), triphenylphosphine (1.30 g) and 2-(dimethylaminoethanol) (0.40 ml) in dry THF (20 ml) stirred at room temperature under nitrogen. After 3 h, the solution was concentrated in vacuo and the residual gum purified by chromatography, eluting with ethyl acetate to give the title compound as a white foam (0.97 g).

T.l.c. (ethyl acetate) Rf 0.15
Similarly prepared

Intermediate 57

2-(1,3-Di(triphenylmethyl)oxy)propyl1-[[3-bromo-2-[2-[2H-tetrazol-5-yl]phenyl]5-benzofuranyl]methyl]-2-butyl-4-chloro-1-(triphenylmethyl)-2H-imidazole-5-carboxylate as a pale yellow foam (2.00 g). T.l.c (dichloromethane) Rf 0.7

From DEAD (0.75 ml) in dry THF (5 ml), Intermediate 18 (2.00 g), triphenylphosphine (1.30 g) and 1,3-di(-triphenylmethyloxy)propan-2-ol (2.30 g) in dry THF (20 ml); reaction time 16 hours. Purification by chromatography eluting with dichloromethane: hexane (1:1) afforded the title compound.

Intermediate 58

2-Methoxyethyl1-[[3-bromo-2-[2-[2-(triphenylmethyl)-2H-tetrazol-5-yl]phenyl]-5-benzofuranyl]methyl]-2-butyl-4-chloro-1H-imidazole-5-carboxylate as a colourless foam (261 mg).

T.l.c. dichloromethane/methanol (500:1). Rf=0.2.

From DEAD (0.65 g), intermediate 18 (2 g), triphenylphosphine (0.98 g) and 2-methoxyethanol (0.57 g) in dry THF (50 ml); reaction time 12 hours. Purification by chromatography eluting with dichloromethane/ethanol (500:1) afforded the title compound.

Intermediate 59

1-Methylethyl1-[[3-bromo-2-[2-[2-(triphenylmethyl)-2H-tetrazol-5-yl]phenyl]-5-benzofuranyl]methyl]-2-butyl-4-chloro-1H-imidazole-5-carboxylate as a yellow gum (781 mg). T.l.c. Petroleum ether/ether (1:1) Rf 0.5.

From DEAD (0.33 g) in dry THF (10 ml), Intermediate 18 (1 g), triphenylphosphine (493 mg) and propan-2-ol (0.14 ml) in dry THF (10 ml); reaction time 3 days. Purification by chromatography, eluting with petroleum/ether (3:1), afforded the title compound.

Intermediate 60

1 -[[3-Bromo-2-[2-[2-(triphenylmethyl)-2H-tetrazol-5-yl]-5-benzofuranyl]methyl]-2-butyl-4-chloro-1H-imidazole-5-carboxamide To a solution of Intermediate 18 (1 g) in dry THF (10 ml) was added 1,1'-carbonyldiimidazole (244 mg). After stirring at room temperature for 1 h a further quantity of 1,1'-carbonyldiimidazole (163 mg) was added and stirring continued overnight. Ammonia (2 ml) was added to the reaction mixture which was stirred for 3 h and then concentrated in vacuo. The residue was purified by chromatography, eluting with petroleum ether/ether (1:2) to give the title compound as a white foam (254 mg).

T.l.c. ether, Rf 0.52.

Intermediate 61

1-[[1-[[3-Bromo-2-[2-[2-(triphenylmethyl)-2H-tetrazol-5-yl]phenyl]-5-benzofuranyl]methyl]-2-butyl-4-chloro-1H-imidazol-5-yl]carbonyl]pyrrolidine To a solution of Intermediate 18 (1.45 g) in dry THF (10 ml) was added 1,1'carbonyldiimidazole (442 mg), and the mixture to stirred overnight. A further quantity of 1,1'-carbonyldiimidazole was added (442 mg). After stirring for 2 h pyrrolidine (0.3 ml) was added to the reaction mixture and after a further 2 h more pyrrolidine (0.3 ml) was added. After stirring for 2 h the reaction mixture was concentrated in vacuo and the residue purified by chromatography, eluting with ether, to give the title compound as a white foam (1.23 g).

T.l.c. ether, Rf 0.53.
Similarly prepared

Intermediate 62

1-[[3-Bromo-2-[2-[2-(triphenylmethyl)-2H-tetrazol-5-yl]phenyl]-5-benzofuranyl]methyl]-2-butyl-4-chloro-N-methyl-1H-imidazole-5-carboxamide as a white foam (1.37 g).

T.l.c. ether, Rf 0.62.

From Intermediate 18 (1.45 g) in dry THF (10 ml), 1,1'-carbonyldiimidazole (442 mg), and a further quantity of 1,1'-carbonyldiimidazole (442 mg). Methyl amine (0.31 ml) was added to the reaction mixture and the addition repeated after 2 h, 18 h and 26 h. Purification by chromatography, eluting with ether, afforded the title compound.

Intermediate 63

1-[[3-Bromo-2-[2-[2-(triphenylmethyl)-2H-tetrazol-5-yl]phenyl]-5-benzofuranyl]methyl]-2-butyl-4-chloro-N,N-dimethyl-1H-imidazole-5-carboxamide as a white foam (1.19 g).

T.l.c. ether, Rf 0.61.

From Intermediate 18 (1.45 g) in dry THF (10 ml), 1,1'-carbonyldiimidazole (442 mg), and a further quantity of 1,1'-carbonyldiimidazole (442 mg). Dimethyl amine (0.45 ml, 40% aqueous solution) was added to the reaction mixture and the addition repeated after a further 2 h. Purification by chromatography, eluting with ether, afforded the title compound.

Intermediate 64

1-[[3-Bromo-2-[2-[2-(triphenylmethyl)-2H-tetrazol-5-yl]phenyl]-5-benzofuranyl]methyl]-2-butyl-4-chloro-N-methyl-1H-imidazole-5-acetamide 1,1'carbonyldiimidazole (148 mg) was added to a stirring solution of Intermediate 98 (250 mg) in THF (5 ml) and the resultant solution was stirred at room temperature for 4 h. Methylamine hydrochloride (249.5 mg) and then triethylamine (546 μl) were added and the reaction mixture stirred at room temperature for 16 h. Methylamine hydrochloride (249.5 mg) and triethylamine (546 μl) were again added and after 6 h the solids were removed by filtration and the filtrate concentrated in vacuo. Chromatography eluting with ether gave the title compound (111 mg) as a white solid.

T.l.c. Rf ether=0.21

Intermediate 65

1-[[3-Bromo-2-[2-[2-(triphenylmethyl)-2H-tetrazol-5-yl]phenyl]-5-benzofuranyl]methyl]-2-butyl-4-chloro-N-ethyl-1H-imidazole-5-carboxamide 1,1'-carbonyldiimidazole (1.21 g) was added to a stirring solution of Intermediate 18 (2 g) in THF (15 ml) and the resultant solution stirred at room temperature for 5 h. Ethylamine (70% in water, 968 mg) was added and the resulting solution stirred for further 16 hours. The reaction mixture was concentrated in vacuo and the residue purified by column chromatography eluting with ether:petroleum ether (5:1) to afford the title compound (1.80 g) as a white solid.

Rf ether=0.78

Intermediate 66

2-Ethyl-1H-imidazole-5-methanol

Dihydroxyacetone (65 g) was added slowly to liquid ammonia (250-300 ml), followed by ethyl propanimidate hydrochloride (65 g). The suspension was transferred to an autoclave and heated at 90° C. for 16 h. The ammonia was allowed to evaporate and then the reaction mixture concentrated in vacuo. The residue was dissolved in methanol, washed with charcoal, and then purified by chromatography, eluting with a gradient of System C (300:8:1 to 50:8:1). Trituration with acetone gave the title compound (29.83 g) as a white solid.

T.l.c. System C (50:8:1) Rf 0.21

Intermediate 67

4-Chloro-2-ethyl-1H-imidazole-5-methanol

A solution of Intermediate 66 (19.66 g) in 2-methoxyethanol (175 ml) and 1,4-dioxan (175 ml) was stirred with N-chlorosuccinimide (21.23 g) in the dark at room temperature for 18 h. The solvent was removed in vacuo and the residue partitioned between water, brine and ethyl acetate. The organic extracts were combined, backwashed with water and brine, dried and concentrated in vacuo to a yellow solid. This was triturated twice with dichloromethane to give the title compound as a white solid (11.49 g).

T.l.c. System C (50:8:1) Rf 0.55

Intermediate 68

4-Chloro-2-ethyl-1H-imidazole-5-carboxaldehyde

Intermediate 67 (11.35 g) was treated with manganese dioxide (30.59 g) according to the method of Intermediate 16 to give the title compound as a white solid (6.41 g)

T.l.c. System C (50:8:1) Rf 0.73

Intermediate 69

1-[[3-Bromo-2-[2-[2-(triphenylmethyl)-2H-tetrazol-5-yl]phenyl]-5-benzofuranyl]methyl]-4-chloro-2-ethyl-1H-imidazole-5-carboxaldehyde A mixture of Intermediate 68 (2 g), Intermediate 15 (12.8 g) and potassuim carbonate (2.61 g) in dry DMF (150 ml) was treated according to the method of Intermediate 17. Trituration with ether and ethyl acetate gave a pale brown solid (1.08 g). This was combined with a further quantity (3.46 g) which crystallised from the mother liquor, and recrystallised from ethyl acetate to give the title compound (2.68 g)

T.l.c. petroleum ether:ether (1:1) Rf 0.24

Intermediate 70

1-[[3-Bromo-2-[2-[2-(triphenylmethyl)-2H-tetrazol-5-yl]phenyl]-5-benzofuranyl]methyl]-4-chloro-2-ethyl-1H-imidazole-5-carboxylic acid A solution of sodium chlorite (3.18 g) and sodium dihydrogen phosphate (3.18 g) in water (40 ml) was added to a mixture of Intermediate 69 (2.65 g) in tert-butanol (40 ml), 2-methyl-2-butene (2M in THF, 21.6 ml) and THF (40 ml) and treated according to the method of Intermediate 18. Purification by chromatography, eluting with dichloromethane/methanol (20:1) gave the title compound (2.17 g).

T.l.c. dichloromethane/methanol (10:1) Rf 0.48

Intermediate 71

1-[[3-Bromo-2-[2-[2-(triphenylmethyl)-2H tetrazol-5-yl]phenyl]-5-benzofuranyl]methyl]-4-chloro-2-ethyl-N-methyl-1H-imidazole-5 carboxamide. Intermediate 70 (503 mg) was dissolved in THF (5 ml), 1,1'- carbonyldiimidazole (338 mg) added, and the solution stirred at room temperature for 3.5 h. Methylamine (323 mg) was added and the solution stirred at room temperature for 48 h. The mixture was concentrated in vacuo and the purified by column chromatography, eluting with ether, to yield the rifle compound (445 mg).

T.l.c. ether Rf=0.30

Intermediate 72

2-Butyl-1H-imidazole-5-carboxaldehyde

To a suspension of 2-butyl-1H-imidazole-5-methanol (2.02 g) in dry dichloromethane (40 ml) and dry dioxan (60 ml) was added manganese dioxide (7.05 g). The reaction mixture was heated at reflux for 3.5 h before being filtered, and the filtrate concentrated in vacuo to give the title compound as a white solid (1.69 g).

T.l.c. System C (100:16:1) Rf 0.38

Intermediates 73 and 74

1-[[3-Bromo-2-[2-[2-(triphenylmethyl)-2H-tetrazol-5-yl]phenyl]-5-benzofuranyl]methyl]-2-butyl-1H-imidazole-5-carboxaldehyde, and 1-[[3-Bromo-2-[2-[2-(triphenylmethyl)-2H-tetrazol-5-yl]phenyl]-5-benzofuranyl]methyl]-2-butyl-1H-imidazole-4-carboxaldehyde A mixture of Intermediate 72 (1 g), Intermediate 15 (6.14 g) and potassium carbonate (0.98 g) in dry DMF (160 ml) was treated according to the method of Intermediate 17. Purification by chromatography eluting with ethyl acetate/hexane (1:1) and again using dichloromethane:methanol (70:1) gave Intermediates 73 and 74 (556 mg and 640 mg, respectively).

T.l.c. dichloromethane/methanol (70:1): Intermediate 73 Rf=0.31 Intermediate 74 Rf=0.24

Intermediate 75

1-[[3-Bromo-2-[2-[2-(triphenylmethyl)-2H-tetrazol-5-benzofuranyl]methyl]-2-butyl-1H-imidazole-5-carboxylic acid A solution of sodium chlorite (665 mg) and sodium dihydrogen phosphate (665 mg) in water (10 ml), was added to a mixture of Intermediate 73 (550 mg) in tert-butanol (10 ml) and 2-methyl-2-butene (2M in THF, 4.4 ml) and THF (10 ml) and treated according to the method of Intermediate 18, to give the title compound as a white solid (44 mg).

T.l.c. dichloromethane/methanol (10:1) Rf 0.47

Intermediate 76

1-[[3-Bromo-2-[2-[2-(triphenymethyl)-2H-tetrazol-5-yl]phenyl]-5-benzofuranyl]methyl]-2-butyl-1H-imidazole-4-carboxylic acid A solution of sodium chlorite (762 mg) and sodium dihydrogen phosphate (762 mg) in water (10 ml), was added to a mixture of Intermediate 74 (630 mg) in tert-butanol (10 ml) and 2 methyl-2-butene (2M in THF, 5 ml) and THF (10 ml) and treated according to the method of Intermediate 18 to give the title compound as a pale yellow solid (433 mg).

T.l.c. dichloromethane/methanol 10:1, Rf 0.51

Intermediate 77

1-[[3-Bromo-2-[2-[2-(triphenylmethyl)-2H-tetrazol-5-yl]phenyl]-5-benzofuranyl]methyl]-4-chloro-2-propyl-N-methyl-1H-imidazole-5-carboxamide 1,1'-carbonyldiimidazole (1.0 g) was added to a solution of Intermediate 36 (1.9 g) in dry THF (30 ml) and the mixture stirred overnight under nitrogen. Methylamine (2 ml; 40% aqueous solution) was added and the reaction mixture stirred for 6 h. The solvents were removed in vacuo and the residue chromatographed eluting with ether to give the title compound (1.56 g).

T.l.c. ether Rf=0.5.

Intermediate 78

1-[[3-Bromo-2-[2-[2-(triphenylmethyl)-2H-tetrazol-5-yl]phenyl]-5-benzofuranyl]methyl]-2-butyl-4-chloro-N-isopropyl-1H-imidazole-5-carboxamide.

Intermediate 18 (1.5 g) was dissolved in dry THF (10 ml), 1,1'-carbonyldiimidazole (0.93 g) added, and the resulting solution stirred at room temperature for 16 h. Isopropylamine (1.29 ml) was added and the solution stirred for 2 h. The mixture was concentrated in vacuo and purified by column chromatography, eluting with System A (5:1) to give the title compound (1.17 g).

T.l.c. ether Rf=0.70.

Intermediate 79

2-Butyl-4-iodo-5-hydroxymethyl-1H-imidazole

N-iodosuccinimide (15.9 g) was added to a stirred solution of 2-butyl-1H-imidazole-5-methanol (10.4 g) in dioxan (200 ml) and the mixture stirred at room temperature in the dark for 16 h. The solvent was evaporated and the residue triturated with ethyl acetate (50 ml) and water (50 ml). The cream precipitate was filtered and washed well with water and dried in vacuo to give a cream powder (14.1 g). The aqueous mother liquors were extracted with ethyl acetate (×3). The combined organic extracts were washed with water (×2), brine, dried and concentrated to give the title compound a cream powder (2.8 g).

T.l.c. System C (100:8:1). Rf=0.7.

Intermediate 80

2-Butyl-4-iodo-1H-imidazole-5-carboxaldehyde

Intermediate 79 (16.9 g) was treated with manganese dioxide (30 g) according to the method of Intermediate 16 to give the title compound as a pale yellow solid (15.15 g).

T.l.c. (ether) Rf=0.8.

Intermediate 81

1-[[3-Bromo-2-[2-[2-(triphenylmethyl)-2H-tetrazol-5-yl]phenyl]-5-benzofuranyl]methyl]-2-butyl-4-iodo-1H-imidazole-5-carboxaldehyde A mixture of Intermediate 15 (16.6 g), Intermediate 80 (5 g) and potassium carbonate (3.4 g) in DMF (200 ml) was treated according to the method of Intermediate 17. Trituration with ether:ethyl acetate (5:1; 150 ml) gave a pale yellow precipitate which was filtered and dried in vacuo gave the title compound as a pale yellow powder (9.25 g).

T.l.c. petroleum ether:ether (1:1) Rf=0.4.

Intermediate 82

1-[[3-Bromo-2-[2-[2-(triphenylmethyl)-2H-tetrazol-5-yl]phenyl]-5-benzofuranyl]methyl]-2-butyl-4-iodo-1H-imidazole-5-carboxylic acid A solution of sodium chlorite (7,45 g) and sodium dihydrogenphosphate (9.7 g) in water (50 ml) was added to a mixture of Intermediate 81 (9.0 g) in tert-butanol (100 ml), 2-methyl-2-butene (13 ml) and THF (160 ml) and treated according to the method of Intermediate 18 to give the title compound as white foam (9.3 g).

T.l.c. petroleum ether:ether (1:1) Rf=0.1.

Intermediate 83

Ethyl 1-[[3-bromo-2-[2-[2-(triphenylmethyl)-2H-tetrazol-5-yl]phenyl]-5-benzofuranyl]methyl]-2-butyl-4-iodo-1H-imidazole-5-carboxylate A solution of (DEAD) (1.79 g) in THF (50 ml) was added to a solution of Intermediate 82 (8.3 g), triphenylphosphine (2.69 g) and ethanol (1.4 g) in THF (100 ml) and the reaction mixture stirred at room temperature overnight. The solvent was removed in vacuo and the residue chromatographed eluting with dichloromethane:ether (98:2) to give the title compound as a white foam (6.5 g).

T.l.c. dichloromethane:ether, (98:2) Rf=0.3.

Intermediate 84

Ethyl 1-[[3-bromo-2-[2-[2-(triphenylmethyl)-2H-tetrazol-5-yl]phenyl]-5-benzofuranyl]methyl]-2-butyl-4-trifluoromethyl-1H-imidazole-5-carboxylate Dibromodifluoromethane (10.5 g) was added to a stirred suspension of cadmium metal (11.2 g) in dry DMF (25 ml) under nitrogen over a period of 40 mins, (CARE: Very exothermic reaction results; external cooling is necessary.) The reaction mixture was stirred for 2 h at room temperature and then the dark brown solution filtered through a "filter stick" under nitrogen into a clean dry flask. This solution is approx 1M in $CF_3Cd$. Copper(1) bromide (1,.5 g) was added to 8 ml (approx 8 mmol) of the above trifluoromethyl cadmium reagent followed by hexamethylphosphoramide (8 ml) and the mixture stirred at room temperature for 10 mins. A solution of Intermediate 83 (2.1 g) in DMF (5 ml) was added and the reaction mixture heated at 70° C. for 2 h. The dark reaction mixture was poured into water and extracted with ethyl acetate. The combined organic extracts were washed with water and brine, then dried and evaporated to give a dark brown oil. This oil was chromatographed to give the title compound as a pale yellow foam (220 mg).

T.l.c. dichloromethane:ether; (98:2) Rf=0.7.

Intermediate 85

Ethyl 2-butyl-4-methyl-1H-imidazole-5-carboxylate

Potassium carbonate (6.36 g) and ethyl 2-amino-3-oxobutanoate (3.99 g) were added under nitrogen to a stirred solution of ethyl pentamidate (5.15 g) in ethanol (30 ml). Stirring was continued overnight. The resulting suspension was filtered and evaporated to give an orange oil. This was purified by column chromatography eluting with ether to afford the title compound as a white solid (137 mg).

T.l.c. ether, Rf 0.4

Intermediate 86

Ethyl 1-[[3-bromo-2-[2-[2-triphenylmethyl-1H-tetrazol-5-yl]phenyl]5-benzofuranyl]methyl]-2-butyl-4-methyl-1H-imidazole-5-carboxylate A solution of Intermediate 15 (0.65 g) in DMF (10 ml) was treated with Intermediate 85 (0.15 g) and sodium hydride (0.22 g) and stirred overnight. The solvent volume was reduced and the residue partitioned between water and ethyl acetate. The aqueous phase was further extracted with ethyl acetate and the combined organic extracts dried, filtered and evaporated. The resulting orange oil was purified by column chromatography eluting with System A (9:1) to give the title compound as a yellow solid (0.25 g).

T.l.c. ether, Rf 0.6

Intermediate 87

2-Butyl-4,5-dichloro-1H-imidazole

A solution of 2-butyl-1H-imidazole-5-methanol (30 g) in 2-methoxyethanol (250 ml) and 1,4-dioxan (250 ml) was treated with N-chlorosuccinimide (28.6 g) and stirred in the dark for 18 h. The solvent was removed in vacuo to give a light yellow solid which was partitioned between water:brine (1:1) (3×100 ml) and ethyl acetate (300 ml). The aqueous phase was saturated with sodium chloride and extracted with ethyl acetate (3×50 ml). The mixture was filtered and the combined organic extracts and washings were evaporated in vacuo to give a brown solid. This was triturated with dichloromethane (75 ml) and the triturates concentrated in vacuo and purified by chromatography eluting with System C (100:8:1) to give the title compound (4.8 g) as a light orange solid.

T.l.c. System C (100:8:1), Rf 0.71

Intermediate 88

3-Bromo-5-[[2-butyl-4,5-dichloro-1H-imidazol-1-yl]methyl]-2-]2-]2-(triphenylmethyl)-2H-tetrazol-5-yl]phenyl]benzofuran Intermediate 15 (1.0 g) was added to a solution of Intermediate 87 (0.281 g) and sodium methoxide (0.078 g) in dry DMF (25 ml) and treated according to the method of Intermediate 4. Purification by chromatography eluting with System A (1:2) gave the title compound (0.53 g) as a pale yellow solid.

n.m.r.(CDCl$_3$) 8.2 δ(m,1H), 7.65 δ(m,3H), 6.75–7.32 δ(m,18H), 5.18 δ(m,2H), 2.58 δ(t,2H), 1.67 δ(m,2H), 1.32 δ(m,2H). 0.88 δ(t,3H).

Intermediate 89

2-Hydroxy-4-methylbenzenecarboxaldehyde

A solution of ethyl bromide (13.8 ml) in THF (100 ml) was added dropwise, under nitrogen to a stirred mixture of magnesium turnings (4.44 g) in dry THF (50 ml). After complete Grignard formation a solution of m-cresol (20 g) in THF (100 ml) was added dropwise. The resulting suspension was stirred for 15 mins before a solution of 1,3-dimethyl-3,4,5,6-tetrahydropyrimidin-2-one (23.7 g) in dry toluene (300 ml) was added dropwise followed by paraformaldehyde (13.85 g). The resulting suspension was heated at reflux overnight. After cooling the suspension was treated with 10% HCl (200 ml) and filtered before separating the organic phase. The organic extracts were washed with water (4×100 ml), dried and evaporated to a yellow crystalline solid (11 g). Low temperature crystallisation from ether gave the title compound as a white crystalline solid (5.31 g). A second crop (0.695 g) was also obtained.

T.l.c. System A (1:9) Rf 0.50

Intermediate 90

2-(2-Benzofuranyl-6-methyl)benzoninile

Sodium methoxide (2.55 g) was added to a stirred solution of Intermediate 89 (5.79 g) in DMF (30 ml) and the phenoxide was formed as a precipitate. Stirring at room temperature was continued for ~15 mins before addition of α-bromo-o-tolunitrile (8.43 g). After 2 h a further equivalent of sodium methoxide (2.55 g) was added and the reaction heated to 80° C. After 30 min, the reaction was poured into water (200 ml) and the solid collected by filtration to give a pale orange solid (7.54 g). This was crystallised from methanol to give the title compound as an off-white crystalline solid (5.04 g).

T.l.c. System A (1:9), Rf 0.45

Intermediate 91

2-(2-Benzofuranyl-3-bromo-6-methyl)benzoninile

A solution of Intermediate 90 (4.142 g) in carbon tetrachloride (100 ml) was treated with a 1M solution of bromine in carbon tetrachloride (23 ml), dropwise under nitrogen at −10° C. The reaction mixture was stirred at room temperature overnight. Further bromine solution was added. (12.6 ml). After a further 3 h the reaction was diluted with dichloromethane (100 ml) and washed with sodium thiosulphate (3×50 ml), and water (50 ml), dried, filtered and evaporated to give the title compound as a yellow solid (6.65 g) found to be a 1:1 mixture with 2-[3-Bromo-6-(bromomethyl)-2-benzofuranyl]benzonitrile.

T.l.c. System A (1:9) Rf 0.3, 0.35 (two spots)

Intermediate 92

2-[2-Benzofuranyl-3-bromo-6-(bromomethyl)]benzonitrile

A solution of Intermediate 91 (4.1 g) in carbon tetrachloride (100 ml) was treated with a 1M solution of bromine in carbon tetrachloride (23 ml) as in Intermediate 92. Purification by chromatography, eluting with System A (1:1), gave the title compound as a pale yellow solid (0.4 1 g).

T.l.c. System A (1:1), Rf 0.8

Intermediate 93

2-(2-Benzofuranyl)-3-bromo-6-[[2-butyl-4-chloro-5-formyl-1H-imidazol-1-yl]methyl]benzonitrile A mixture of Intermediate 16 (0.20 g) and the Intermediate 92 (0.41 g) in DMF containing potassium carbonate (0.17 g) was heated at 80° C. for 16 h under nitrogen. After cooling, the yellow solution was poured into water (60 ml) and extracted with ethyl acetate (3×70 ml). The combined organic extracts were washed with water (4×75 ml), dried and concentrated in vacuo, to afford a yellow oil which was purified by chromatography, eluting with System A (1:1) to give the title compound as a pale yellow foam (0,32 g).

T.l.c. System A (2:1), Rf 0.4

Intermediate 94

1-[6-[3-Bromo-2-(2-cyanophenyl)benzofuranyl]methyl]-2-butyl-4-chloro-1H-imidazole-5-carboxylic acid A solution of sodium chlorite (80% tech, 1.51 g) and sodium dihydrogen orthophosphate (1.55 g) in water (15 ml) was added to a stirred mixture of Intermediate 93 (0.8 g) and 2-methylbut-2-ene (9.5 ml, 2M solution in THF) in THF (20 ml) and tert-butanol (20 ml). The mixture was stirred vigorously at room temperature for 16 h, before being partitioned between saturated ammonium chloride (60 ml) and ethyl acetate (100 ml). The separated organic phase was washed with water (100 ml), dried and evaporated in vacuo to afford the title compound as a white foam (0.82 g).

T.l.c. ether, Rf 0.45

Intermediate 95

1-[[3-Bromo-2-[2-[2-(triphenylmethyl)-2H-tetrazol-5yl]-phenyl]-5-benzofuranyl]methyl]-2-butyl-4-chloro-1H-imidazole-5-methanol Triethylamine (182 μl) was added to a stirring suspension of the product of Example 3 (700 mg) in dichloromethane (2.5 ml) and then chlorotriphenylmethane (352 mg) was added and the resultant solution stirred at room temperature for 2 h. The reaction mixture was then partitioned between water (20 ml) and dichloromethane. The separated organic phases were washed with water (20 ml), dried and concentrated in vacuo to afford the title compound as a white solid (571 mg).

T.l.c ether Rf=0.77.

Intermediate 96

1-[[3-Bromo-2-[2-[2-(triphenylmethyl)-2H-tetrazol-5-yl]phenyl]-5-benzofuranyl]methyl]-2-butyl-4-chloro-5-(chloromethyl)-1H-imidazole Dimethylsulphide (114 μl) was added to a stirring solution of N- chlorosuccinimide (190 mg) at 0° C. in dichloromethane and the resultant white suspension cooled to −20° C. prior to the addition of Intermediate 95 (1 g) in dichloromethane (70 ml) dropwise over 30 min. The suspension was warmed to 0° C. and stirred at 0° C. for 4 h and then at room temperature for 48 h. The reaction mixture was concentrated in vacuo and purified by column chromatography eluting with ether:petroleum ether (2:1) to afford the title compound (301 mg) as a white solid.

T.l.c ether:petroleum ether (2:1) Rf=0.72.

Intermediate 97

1-[[3-Bromo-2-[2-[2-(triphenylmethyl)-2H-tetrazol-5-yl]phenyl]-5-bezonfuranyl]methyl]-2-butyl-4-chloro-5-(cyanomethyl)-1H-imidazole A solution of Intermediate 96 (300 mg) in DMSO (3 ml) was added to a stirring solution of sodium cyanide (109 mg) in DMSO (7.5 ml) and the resultant solution stirred at room temperature for 24 hours. Water (30 ml) was added and the resultant mixture extracted into ethyl acetate (3×30 ml). The combined organic extracts were washed with water (2×30 ml), dried and concentrated in vacuo to afford the crude product which was purified by column chromatography eluting with petroleum ether:ether (2:1) to afford the title compound (57 mg) as a white solid.

I.r (Nujol) 2210, 1709, 1253, 1465, 1450, 1252, 761, 748, 698 cm$^{-1}$

Intermediate 98

1-[[3-Bromo-2-[2-[2-(triphenylmethyl)-2H-tetrazol-5-yl]phenyl]-5-benzofuranyl]methyl]-2-butyl-4-chloro-1H-imidazole-5-acetic acid Triethylamine (82 μl) was added to a stirring mixture of the product of Example 48 (100 mg) in dichloromethane (10 ml) and then chlorotriphenylmethane (94.5 mg) was added to the resultant solution followed by DMAP (2 mg) and the solution stirred at room temperature for 5 h. Water (10 ml) was added and the mixture stirred vigorously at room temperature for 5 min. The separated aqueous phase was extracted into dichloromethane (10 ml) and the combined organic extracts dried and concentrated in vacuo to afford the crude product. Column chromatography eluting with dichloromethane:acetic acid:methanol (96:2:2) gave the title compound (60 mg) as a white solid.

T.l.c dichloromethane:acetic acid:methanol (96:2:2) Rf=0.45

Intermediate 99

Ethyl 2-(5-methyl-2-benzofuranyl)benzoate

Sodium carbonate (1N; 60 ml) was added to a mixture of Intermediate 1 (4.7 g), ethyl 2-bromobenzoate (5.89 g) and tetrakis- triphenylphosphine palladium (0) (0.88 g) in DME (100 ml). The mixture was heated at reflux for 18 h, cooled to room temperature and then concentrated in vacuo. The residue was extracted with ether (3×100 ml) and the combined extracts washed with brine (1×100 ml) and dried. The solvent was evaporated to give a brown oil (5 g) which was purified by column chromatography eluting with System A (1:20) to give the title compound as a pale yellow oil (2.89 g).

T.l.c. System A (1:20), Rf=0.2.

Intermediate 100

Ethyl 2-(3-bromo-5-methyl-2-benzofuranyl)benzoate

Bromine (1.05 ml) in carbon tetrachloride (5 ml) was added dropwise to a solution of Intermediate 99 (2.88 g) in dry dioxan (50 ml) at 25° C. under nitrogen. The mixture was stirred for 1 h, then cyclohexene (2 ml) was added. The solvent was evaporated and the residue purified by column chromatography eluting with petroleum ether:ether (20:1) to give the title compound as a colourless oil (3.57 g).

T.l.c. petroleum ether:ether (20:1) Rf=0.25.

Intermediate 101

Ethyl 2-(3-bromo-5-bromomethyl-2-benzofurany)benzoate

NBS (1.94 g) was added to a solution of Intermediate 100 (3.56 g) in carbon tetrachloride (80 ml). Dibenzoyl peroxide (0.25 g) was added and the mixture heated under reflux for 3 h. The cooled mixture was filtered and the filtrate evaporated. The residue was purified by column chromatography eluting with System A (1:30) to give the title compound as a colourless gum (3.66 g).

T.l.c. petroleum ether:ether (20:1), Rf=0.2.

Intermediate 102

Ethyl 2-[[3-bromo-5-[(2-butyl-4-chloro-5-formyl)-1H-imidazol-1-yl]methyl]-2-benzofuranyl]benzoate A mixture of Intermediate 16 (1.43 g), Intermediate 101 (3.66 g) and potassium carbonate (1.17 g) in dry DMF (60 ml) was treated according to the method of Intermediate 17 to give title compound as a colourless gum (3.67 g).

T.l.c. ether:petroleum ether (1:1) Rf=0.4.

Intermediate 103

5-[2-[5-[[5-(Azidomethyl)-2-butyl-4-chloro-1H-imidazol-1-yl]methyl]-3-bromo-2-benzofuranyl]-phenyl]-2-(triphenylmethyl)-2H-tetrazole Mesyl chloride (0.10 ml) was added dropwise to a mixture of Intermediate 95 (1.02 g) and triethylamine (0.13 g) in dry dichloromethane (15 ml) and stirred at room temperature under nitrogen. After 1 h, lithium azide (200 mg) and 12-crown-4-ether (50 mg) were added to the solution. The mixture was concentrated in vacuo, DMF (15 ml) added and the mixture heated at 60° C. for 2 h. The mixture was concentrated in vacuo to give a colourless gum. Purification by chromatography eluting with ether:dichloromethane:hexane (0:1:1→1:10:5) gave the title compound (213 mg) as a colourless gum.

T.l.c. ether Rf 0.85.

Intermediate 104

1-[[3-Bromo-2-[2-[2-(triphenylmethyl)-2H-tetrazol-5-yl]phenyl]-]5]benzofuranyl]methyl]-2-butyl-4-chloro-1H-imidazole-5-methanamine A solution of Intermediate 102 (516 mg) and triphenylphosphine (200 mg) in dry dichloromethane (10 ml) under nitrogen was stood at room temperature for 15 h. The solution was concentrated in vacuo, the residue taken up in conc.aqueous ammonia (2 ml), methanol (10 ml) and dichloromethane (2 ml) and stood at room temperature for 16 h. The solution was concentrated in vacuo and the product isolated by chromatography, eluting with the ethyl acetate to give a pale yellow oil (438 mg). The oil was purified by chromatography eluting with System C (300:8:1) to give the title compound (352 mg) as a pale yellow oil.

T.l.c. ethyl acetate Rf 0.2

Intermediate 105

N-[[1-[[3-Bromo-2-[2-[2-(triphenylmethyl)-2H-tetrazol-5-yl]phenyl]-5-benzofuranyl]methyl]2-butyl-4-chloro-1H-imidazol-5-yl]methyl]acetamide A solution of Intermediate 104 (409 mg), triethylamine (150 μl) and acetic anhydride (100 μl) in dry dichloromethane (10 ml) was stood at room temperature for 3 h. The product was isolated by chromatography, eluting with System B (1:1) to give the title compound as a white foam (405 mg).

T.l.c. System B (1:1) Rf 0.3
Similarly prepared

Intermediate 106

Methyl [[1-[[3-bromo-2-[2-[2-(triphenylmethyl)-2H-tetrazol-5-yl]phenyl]-5-benzofuranyl]methyl]-2-butyl-4-chloro-1H-imidazol-5-yl]methyl]carbamate as a white foam (434 mg).

T.l.c System B (4:1) Rf=0.45.

From a solution of Intermediate 104 (500 mg), triethylamine (200 μl) and methyl chloroformate (100 μl) in dry dichloromethane (10 ml).

Intermediate 107

N-[[1-[[3-Bromo-2-[2-[2-(triphenylmethyl)-2H-tetrazol-5-yl]phenyl]-5-benzofuranyl]methyl]-2-butyl-4-chloro-1H-imidazol-5-yl]methyl]formamide A solution of Intermediate 104 (398 mg) in ethyl formate (10 ml) was heated at reflux for 3 h under nitrogen. The solution was concentrated in vacuo and the product isolated by chromatography, eluting with System B (1:4) to give the title compound as a colourless gum.

T.l.c. System B (1:4), Rf0.2

Intermediate 108

[[1-[[3-Bromo-2-[2-[2-(triphenylmethyl)-2H-tetrazol-5-yl]phenyl]-5-benzofuranyl]methyl]-2-butyl-4-chloro-1H-imidazol-5-yl]methyl]urea Silicon tetraisocyanate (35 mg) was added to a solution of Intermediate 104 (505 mg) in dry toluene and stirred at room temperature under nitrogen. After 10 mins, the solution was heated to 100° C. After 30 mins the mixture was cooled and the solvent removed in vacuo. Isopropanol (9 ml) and water (1 ml) were added and the solution heated at reflux for 30 mins. The solution was cooled to room temperature and concentrated in vacuo. Chromatography, eluting with ethyl acetate gave a white foam which was triturated with ether to give the title compound as a white powder (171 mg).

T.l.c. ethyl acetate, Rf 0.2

Intermediate 109

1-(2-Bromo-4-methyl)phenyl-2,2-dimethylpropanoate

A solution of 2-bromo-4-methylphenol (9.14 g) in dry dichloromethane was cooled in an ice-bath under nitrogen and treated with 2,2-dimethylpropanoyl chloride (12.08 ml) and DMAP (17.8 g). Stirring at room temperature was continued overnight. The reaction was washed with 2N HCl, water 8% NaHCO$_3$, water, and dried. Filtration and evaporation gave a pale yellow oil (17.19 g). Purification by column chromatography eluting with System A (1:20) gave the title compound as a colourless oil (8.07 g).

T.l.c. System A (1:2), Rf 0.8

Intermediate 110

1-(2-Hydroxy-4-methyl)phenyl-2,2-dimethylpropan-1-one

A solution of Intermediate 109 (18.3 g) in dry THF (540 ml) and dry ether (96 ml) was cooled to 100° C. and treated dropwise with s-butyl lithium (2M+9;90 ml). After ~30 mins the temperature was warmed to −78° C. and stirring at this temperature continued overnight. The reaction was quenched with saturated aq. NH$_4$Cl and warmed to room temperature. The organic phase was separated and the aqueous phase extracted with ether. The combined organic extracts were washed with water, dried, filtered and evaporated to give a yellow/orange oil (14.4 g). Purification by column chromatography eluting with System A (1:20) gave the title compound as a yellow oil (10.32 g).

T.l.c. hexane Rf=0.35.

Intermediate 111

2-(3-tert-Butyl-5-methyl-2-benzofuranyl)benzonitrile

A solution of Intermediate 110 (9.23 g) in dry DMF (200 g) was treated with sodium hydride (1.59 g) with stirring under nitrogen for 30 mins. Additional DMF (75 ml) was added followed by α-bromo-o-tolunitrile (9.41 g). Stirring at room temperature was continued for 1.5 h. A further equivalent of sodium hydride (1.59 g) was added and the solution heated to 80° C. Stirring at this temperature was continued overnight. The solvent volume was reduced and the residue poured into water and extracted with ethyl acetate and the combined organic extracts washed with water and brine. Drying, filtration and evaporation gave a brown oil (19.76 g). Purification by column chromatrography eluting with System A (1:9) gave the title compound as a pale orange solid (3.09 g).

T.l.c. System A (1:9) Rf 0.45

Intermediate 112

2-[5-(Bromomethyl)-3-[1,1-(dimethylethyl)]-2-benzofuranyl]benzonitrile

A solution of Intermediate 111 (1.98 g) in carbon tetrachloride (40 ml) was treated with NBS (1.35 g) using benzoyl peroxide as a radical initiator according to the method of intermediate 3 to give the title compound as a white foam (0.96 g).

T.l.c. System A (1:9) Rf 0.35

Intermediate 113

2-[5-[2-Butyl-4-chloro-5-(oxomethyl)-1H-imidazol-1-yl]methyl-3-[1, 1-(dimethylethyl)]-2-benzofuranyl]benzonitrile A solution of Intermediate 112 (0.95 g) and Intermediate 16 (0.479 g) in dry DMF (10 ml) was treated with potassium carbonate (0.373 g) according to the method of Intermediate 17. Purification by column chromatography eluting with System A (1:1) gave an off-white foam (0.806 g). Further purification by chromatography eluting with System B (1:10) gave the tire compound as an off-white foam (0.731 g).

T.l.c. System A (1:9), Rf 0.3.

Intermediate 114

1-[[3-(1,1-Dimethylethyl)-2-(cyanophenyl)-5-benzofuranyl]methyl]-2-butyl-4-chloro-1H-imidazole-5-carboxylic acid A solution of Intermediate 113 (0.8 g) in THF (10 ml), tert-butanol (10 ml) and 2-methylbut-2-ene (10.14 ml) was treated with a solution of sodium chlorite (1.52 g) and sodium dihydrogen phosphate (1.52 g) in water (10 ml). Stirring at room temperature was continued overnight. The solvent volume was reduced and the residue partitioned between 1N HCl and ethyl acetate. The aqueous phase was extracted with further ethyl acetate and the combined organic extracts dried, filtered and evaporated to give the title compound as a yellow solid (0.68 g).

T.l.c. ether Rf 0.5

Intermediate 115

2-[5-[-2-Butyl-4-chloro-5-(hydroxymethyl)-1H-imidazol-1-yl]methyl-3-[1,1-(dimethylethyl)]-2-benzofuranyl]benzonitrile A solution of Intermediate 114 (0.29 g) in methanol (8 ml) was treated with sodium borohydride (0.025 g) with stirring under nitrogen. After 1 h the solvent was evaporated and the residue purified by column chromatography eluting with System B (1:2) to give the title compound as a white crystalline solid (0.256 g).

T.l.c. System B (1:10), Rf 0.25.

Intermediate 116

3-Chloro-5-methyl -2-[2-[2-(triphenylmethyl)-2H-tetrazol-5-yl]phenyl]benzofuran n-Butyl lithium (1.67M solution in hexane, 1.5 ml) was added dropwise to a stirred solution of Intermediate 14 (0.98 g) in THF (35 ml) at −73° under nitrogen. After 5 mins, a solution of hexachloroethane (1.15 g) in THF (10 ml) was added dropwise. After 10 mins, brine (1 ml) was added before the cooling bath was removed. After warming to room temperature, the mixture was partitioned between ethyl acetate (40 ml) and water (40 ml). The organic phase was dried and concentrated in vacuo to afford a white solid (1.28 g). Purification by chromatography eluting with System A (1:4) afforded the title compound (0.9 g) as a white solid.

T.l.c. System A (1:9) (1:3), Rf 0.7

Intermediate 117

1-[5-[3-Chloro-2-2-[2-(triphenylmethyl)-2H-tetrazol-5-yl]benzofuranyl]methyl]-2-butyl-4-chloro-1H-imidazole-5-carboxaldehyde NBS (0.35 g) was added to a warm (65°) solution of the Intermediate 116 (0.9 g) in carbon tetrachloride (30 ml) followed by dibenzoyl peroxide (0.05 g). The suspension was then stirred at reflux for 4 h whilst being irradiated with a 250 Watt lamp. The yellow suspension was filtered and the solution concentrated in vacuo to afford an orange solid (0.99 g) which was treated with Intermediate 116 (0.27 g) and potassium carbonate (0.32 g) in DMF (30 ml) according to the method of Intermediate 36. Purification by chromatography eluting with System A (1:7) increasing to (1:1) afforded a yellow semi-solid (0.325 g). Repeated purification by chromatography eluting with System C (300:8:1) gave the title compound (0.107 g) as a near colourless oil.

T.l.c. System A (1:1), Rf 0.3

Intermediate 118

1-[5-[3-Chloro-2-[2-[2-(triphenylmethyl)-2H-tertrazol-5-yl]phenyl]benzofouranyl]methyl]-2-butyl-4-chloro-1H-imidazole-5-carboxylic acid A solution of sodium chlorite (80%, 0.49 g) and sodium dihydrogen orthophosphate (0.51 g) in water (10 ml) was added to a stirred solution of Intermediate 117 (0.46 g) in tert-butanol (10 ml) and THF (10 ml) containing 2-methylbut-2-ene (2M solution in THF, 3 ml). The mixture was vigorously stirred for 16 h before most of the solvent was removed in vacuo and the residue partitioned between ethyl acetate (50 ml) and water (50 ml). The separated organic phase was dried and concentrated in vacuo to afford the title compound (0.38 g) as a yellow viscous oil.

T.l.c. System A (1:1) Rf 0.15

Intermediate 119

Ethyl 1-[[3-bromo-2-[2-[2-(triphenylmethyl)-2H-tetrazole-5-yl]phenyl]-5-benzofuranyl]methyl]-4-chloro-2-formyl-1H-imidazole-5-carboxylate Osmium tetroxide (10 mg) was added to a solution of Intermediate 34 (780 mg) and sodium periodate (819 mg) in 10% aqueous dioxane and the resultant mixture was stirred at room temperature for 2 h. Sodium metabisulphite was added until a colourless mixture was observed. The resultant mixture was extracted into ethyl acetate (3×50 ml) the organic extracts dried and con-

Intermediate 120

Ethyl 1-[[3-bromo-2-[2-[2-(triphenylmethyl)-2H-tetrazole-5-yl]phenyl]-5-benzofuranyl]methyl]-2-but-1(Z)-enyl-4-chloro-1H-imidazole-5-carboxylate Potassium tert-butoxide (64 mg) was added to a stirring suspension of n-propyltriphenylphosphonium bromide (232.5 mg) at 0° C. in THF (3 ml) and the resultant orange mixture stirred at 0° C. for 20 mins prior to the addition of Intermediate 119 (235 mg) in THF (5 ml) over 30 seconds. The resultant white suspension was stirred at 0° C. for 30 mins and the temperature was allowed to attain room temperature and the reaction mixture stirred at room temperature for 1 h. Further n-propyltriphenylphosphonium bromide (100 mg) and potassium tert-butoxide (30 mg) were added and the resultant mixture stirred for 4.5 h. Saturated aqueous ammonium chloride (5 ml) was added and the separated aqueous phase extracted into ethyl acetate (2×5 ml). The combined organic extracts were dried and concentrated in vacuo. The residue was purified by column chromatography eluting with petroleum ether:ether (4:1) to afford the title compound (100 mg).

T.l.c. petroleum ether:ether (1:1) Rf=0.57.

Intermediate 121

Ethyl 1-[[3-bromo-2-[2-[2-(triphenylmethyl)-2H-tetrazol-5-yl]phenyl]-5-benzofuranyl]methyl]-4-chloro-2-pent-1 (Z)-enyl-1H-imidazole-5-carboxylate Intermediate 119 (455 mg) in THF (10 ml) was treated with potassium ten-butoxide (196 mg) and butyltriphenylphosphonium bromide (682 mg) in THF (10 ml) according to the method of Intermediate 120 to give the title compound (102 mg) as a white solid.

T.l.c. petroleum ether:ether (1:1) Rf=0.57.

Intermediate 122

2-[5-[(2-Butyl-4-chloro-5-formyl-1H-imidazol-1-yl)methyl]-3-methoxy-2-benzofuranyl]benzonitrile Activated manganese dioxide (1.2 g) was added to a stirred suspension of Intermediate 29 (1 g) in dichloromethane (10 ml) and 1,4-dioxan (5 ml), and the resulting mixture heated at reflux for 16 h. The reaction was filtered, the filtrate evaporated in vacuo and the residual oil purified by chromatography eluting with ether. A white solid precipitated out of a yellow solution and this was triturated further and filtered to give the title compound (0.46 g) m.p. 118°-120° C.

Intermediate 123

2-Butyl-4-chloro-1-[[2-(2-cyanophenyl)-3-methoxy-5-benzofuranyl]methyl]-1H-imidazole-5-carboxylic acid A solution of sodium chlorite (0.8 g, 80%) and sodium dihydrogen phosphate (0.8 g) in water (5 ml), was added to a mixture of Intermediate 122 (0.4 g) in tert-butanol (10 ml), 2-methyl-2-butene (5.4 ml, 2M in THF) and THF (10 ml) and the mixture treated according to the method of Intermediate 18 to give the title compound as a white solid (0.4 g).m.p. 158°-160° C.

Intermediate 124

(±) 2-Methoxy-1-methylethyl 1-[[3-bromo-2-[2-[2-(triphenylmethyl)-2H-tetrazol-5-yl]phenyl]-5-benzofuranyl]methyl]-2-butyl-4-chloro-1H-imidazole-5-carboxylate DEAD (0.75 ml) was added dropwise to a solution of Intermediate 18 (2.00 g), triphenylphosphine (1.30 g) and (±)-1-methoxy-2-propanol (360 mg) stirred at room temperature under nitrogen. After 16 h, the solution was concentrated in vacuo. Chromatography eluting with trichloromethane gave the title compound as a white foam (2.02 g).

T.l.c. trichloromethane, Rf 0.2

Intermediate 125

Ethyl 1-[[3-bromo-2-(2-cyanophenyl)-5-benzofuranyl]methyl]-2-butyl-5-Chloro-1H-imidazole-4-carboxylate A mixture of ethyl 2-butyl-5-chloro-1H-imidazole-4-carboxylate (494 mg), Intermediate 10 (838 mg) and potassium carbonate (326 mg) in dry DMF (20 ml) was heated at 70° for 3 h. The cooled mixture was partitioned between ethyl acetate (50 ml) and brine/water (1:1) (3×25 ml). The organic extract was dried and the solvent evaporated. The residue was purified by column chromatography eluting with ether:petroleum ether (1:1) to give the title compound (151 mg)

T.l.c. ether/petroleum ether (1:1) Rf 0.15

Intermediate 126

1-[[3-Bromo-2-(2-cyanophenyl)-5-benzofuranyl]methyl]-2-butyl-5chloro-1H-imidazole-4-carboxylic acid A mixture of Intermediate 125, ethanol (1.10 ml), potassium hydroxide (31.2 mg) and water (0.247 ml) was stirred at room temperature for 2 h after which time a further amount of ethanol (1.10 ml), potassium hydroxide (31.2 mg) and water (0.247 ml) were added. 4 h later a further 2 equivalents of all the reagents were added and the reaction mixture stirred at room temperature for 6 h. The reaction mixture was concentrated in vacuo and the residue diluted with water (5 ml) prior to acidification to pH3(2N HCl). The aqueous phase was extracted into ethyl acetate (3×10 ml) and the combined organic extracts dried and concentrated in vacuo to afford the title compound (91 mg) as a white solid.

n.m.r δ(250 MHz), 0.88(3H,t),1.30(2h sex), 1.80(2H,pent), 2.80 (2H,t),5.35(2H,s),7.1(1H,d),7.26(1H,s),7.5(2H,m),7.65(1H,t),7.8(1H,d,8.0(1H,d).

Intermediate 127

2-(3-Bromo-5-methyl-2-benzofuranyl)benzoic acid

A solution of Intermediate 5 (2.20 g) in methanol (20 ml) was treated with sodium hydroxide (2N.~3 ml). The solution was heated to reflux and heating was continued for 3 h. The solvent was removed in vacuo and the residue diluted with water. The basic aqueous phase was washed with ether (3×30 ml) before acidification to pH~2 using 2N HCl. A white suspension formed. This was extracted with ether (4×20 ml) and the combined organic extracts dried, filtered and evaporated to give the title compound as a pale yellow solid (1.93 g).

T.l.c. ether, Rf 0.7

Intermediate 128

1,1-Dimethylethyl[2-(3-bromo-5-methyl-2-benzofuranyl)phenyl]carbamate

A solution of Intermediate 127 (1 g) in dry dioxan (25 ml) was treated with diphenylphosphorylazide (0.65 ml), triethylamine (0.42 ml) and tert-butanol (0.5 ml) before heating to reflux under nitrogen. After 6 h the reaction was cooled and solvent evaporated to give an orange oil. Purification by column chromatography, eluting with System A (1:10) afforded the rifle compound as a cream solid (0.67 g).

--- centrated in vacuo to afford the title compound (697 mg) as a cream solid.

T.l.c. petroleum ether:ether Rf=0.55

T.l.c. System A (1:1), Rf 0.8

Intermediate 129

Ethyl 1-[[3-bromo-2-[2-[[(1,1-dimethylethoxy)carbonyl]amino]phenyl]-5-benzofuranyl]methyl]-2-butyl-4-chloro-1H-imidazole-5-carboxylate A solution of Intermediate 128 (2.20 g) in carbon tetrachloride (50 ml) was treated with NBS (1.02 g) and dibenzoyl peroxide (230 mg) and heated to reflux whilst irradiating with a 250 W tungsten bulb. After 2 h the reaction was cooled to room temperature and filtered. The organic phase were washed with water, dried and evaporated to give an orange oil. This was dissolved in DMF and added dropwise at 0° C. to a solution of ethyl 2-butyl-4-chloro-1H-imidazole-5-carboxylate [imidazole (1.26 g)+sodium hydride (60%, 0.218 g) in DMF] and stirred at room temperature under nitrogen overnight. Solvent was removed under reduced pressure and the residue partitioned between ethyl acetate and water. The organic phase was washed with water, dried, filtered and evaporated to give a brown oil (3.90 g). This was purified by column chromatography eluting with System A (1:2) to give the title compound as a yellow foam (0.832 g).

T.l.c. System A (1:1), Rf 0.50.

Intermediate 130

Ethyl 1-[[2-(2-aminophenyl)-3-bromo-5-benzofuranyl]methyl]-2-butyl-4-chloro-1H -imidazole-5 -carboxylate.

A solution of Intermediate 129 (0.124 g) in ethanol (6 ml) was treated dropwise with 2N HCl (2 ml). Stirring at room temperature was continued for 1.5 h. The reaction was heated to reflux and stirring continued for 1 h. The solution was cooled to room temperature and neutralised to pH7 using 2N NaOH. The solvent was evaporated and the residue partitioned between water (30 ml) and ethyl acetate (30 ml). The aqueous phase was further extracted with ethyl acetate (2×15 ml) and the combined organic extracts dried, filtered and evaporated to give the title compound as a brown oil (0.089 g).

T.l.c. System A (1:1) Rf 0.30

Intermediate 131

Ethyl 2-(hydroxyimino)-3-oxohexanoate

A solution of sodium nitrite (2.94) in water (7 ml) was added over 1.5 h at 25°–30° C. to a stirred solution of ethyl 3-oxohexanoate (5.0 g) in glacial acetic acid (6 ml). The orange mixture was stirred at 25° C. for 0.5 h before dilution with water (2 ml) and stirring at 20° C. for 15.5 h. The mixture was extracted with ether (2×20 ml) and the combined extracts washed with water (20 ml), 8% sodium bicarbonate (2×20 ml) and saturated sodium chloride solution (20 ml). The yellow solution was then dried and evaporated in vacuo, to afford a mobile yellow oil (4.95 g).

n.m.r. $\delta(CDCl_3)$ 94 (1H,brs),4.30–4.44 (2H,2×q),2.68–2.82 (2H,2×t),1.6–1.78 (2H,2×m),1.3–1.4 (3H,2×t),0.9–1.1 (3H,2×t).

Intermediate 132

Ethyl 2-amino-3-oxohexanoate hydrochloride

A solution of Intermediate 131 (55.0 g) in ethanol (600 ml) containing concentrated hydrochloric acid (30 ml) was added to prereduced 5% platinum oxide on carbon catalyst (4.0 g). The mixture was stirred under a hydrogen atmosphere for 20 h. The catalyst was removed by filtration through acid(HCl)-washed celite and evaporated to an oil which was dried by azeotropic distillation with ethanol. The resultant solid was washed with 10% ethanol in ether, recollected and dried in vacuo to give the title compound as a white solid (43.75 g).

n.m.r. $\delta(CDCl_3$ DMSOd$_6$ 250 MHz 9.18(3H,br s),5.08(1H,s),4.33(2H,q),2.82(2H,t),1.6–1.75(2H,m),1.3–6(3H,t),0.95(3H,t).

Intermediate 133

Ethyl 2-butyl-4-propyl-1H-imidazole-5-carboxylate

Anhydrous potassium carbonate (13.8 g) was added to a stirred solution of Intermediate 132 (10.5 g) and methyl pentanimidate (8.2 g) in ethanol (250 ml). The mixture was stirred at room temperature for 16 h and then evaporated to dryness. The residue was purified by column chromatography eluting with ether. The title compound was obtained as a clear viscous yellow oil (3.0 g)

n.m.r. $\delta(CDCl_3$ 250 MHz)10.1 & 10.8(1H,2×v br s)4.32(2H),q)2.87(2H,br t), 2.7(2H,t)1.6–1.8(4H,m)1.3–1.45(5H,m+t)0.82–1.0(6H,2×t).

Intermediate 134

Ethyl 1-[[3-bromo-2-[2-[2-(triphenylmethyl)-2H-tetrazol-5-yl]phenyl]-5-benzofuranyl]methyl]-2-butyl-4-propyl-1H-imidazole-5-carboxylate.

Anhydrous potassium carbonate (0.4 g) was added to a mixture of Intermediate 133 (0.71 g) and Intermediate 15 (2.86 g) in dry DMF at room temperature. The mixture was stirred for 16 h at room temperature and then heated at 80° for 24 h. The cooled reaction was concentrated in vacuo to give an oily solid which was poured into water. The mixture was extracted with dichloromethane and ether (each 2×100 ml) and the combined extracts were dried, filtered and evaporated to a viscous oil (2.9 g) which was purified by column chromatography eluting with ether to give the title compound as a viscous clear immobile oil (0.93 g).

n.m.r $\delta(CDCl_3$ 250 MHz)8.18–8.22(1H,m),7.66–7.71(1H,m),7.3–7.62(2H,m) 7.22–7.32, 7.1–7.18, 6.82–6.98(15H, 3×m), 7.06 (1H,br s), 6.93(1H,d) 6.77(1H,dd),5.63 (2H,s)4.18 (2H,q)2.9(2H,br t)2.61 (2H,br t)1.62–1.78(4H,m)1.3–1.4(2H,m)1.27(3H,t),1.0(3H,t)0.87(3H,t).

Intermediate 135

2-[3-Bromo-5-[[2-butyl-4-chloro-5-(oxomethyl)-1H-imidazol-1-yl]methyl]-2-benzofuranyl]benzonitrile A solution of Intermediate 10 (9.8 g), Intermediate 16 (4.8 g) and potassium carbonate (5 g) in DMF (250 ml) was treated according to the method of Intermediate 17. Purification by chromatography eluting with petroleum ether:ether (1:1) gave the title compound (6.2 g) as a white solid.

T.l.c petroleum ether:ether (1:1) Rf=0.35

Intermediate 136

1-[[3-Bromo-2-(2-cyanophenyl)-5-benzofuranyl]methyl]-2-butyl-4-chloro-1H -imidazole-5-carboxylic acid A solution of sodium chlorite (8.7 g) and sodium dihydrogen phosphate (8.8 g) in water (50 ml) was added to a mixture of Intermediate 135 (4.8 g) in tert-butanol (100 ml), 2-methyl-2-butene (2M in THF, 60 ml) and THF (100 ml). The mixture was treated according to the method of Intermediate 36 to give a white foam which was triturated with ether and filtered to give the title compound (3.75 g) as a white powder.

T.l.c ether Rf=0.30.

EXAMPLE 1

2-[5-[(2-Butyl-1H-imidazol-1-yl)methyl]-2-benzofuranyl]benzoic acid

A solution of Intermediate 4 (0.236 g) in methanol (3 ml) was treated with 2N NaOH (1 ml), during which time the solution became cloudy. Further methanol (~1 ml) was added until the solution became clear and the solution was then heated at reflux for 2 h. The reaction was then cooled to room temperature and the methanol removed in vacuo. The residue was diluted in water (~5 ml) and neutralised to pH7 by dropwise addition of 2N HCl. The mixture was extracted with ethyl acetate (3×20 ml) and the combined organic extracts dried, filtered and evaporated to give the title compounds as a pale yellow powder (0.085 g), m.p. 153°–157° C.

hplc, (conditions as in Example 7) Retention time=16.87 minutes

EXAMPLE 2

2-[3-Bromo-5-[(2-butyl-1H-imidazol-1-yl)methyl]2-benzofuranyl]benzoic acid

A solution of Intermediate 7 (0.135 g) in methanol (3 ml) was treated with 2N NaOH (1 ml) during which time the solution became cloudy. Further methanol (~1 ml) was added until the solution became clear. The solution was heated at reflux for about 3 h. The reaction was cooled and the methanol evaporated. The residue was diluted with water (~5 ml) and neutralised to pH7 by dropwise addition of 2N HCl. The resulting suspension was extracted with ethyl acetate (3×20 ml). The combined organic extracts were dried, filtered and evaporated to give the title compound as an off-white powder (0.076 g), m.p. 138°–145°.

Assay found C,61.05;H,4.9;N,6.2% $C_{23}H_{21}BrN_2O_3$ requires C,60.9;H,4.6;N,6.2%

EXAMPLE 3

5-[2-[3-Bromo-5-[[2-butyl-4-chloro-5-(hydroxymethyl)-1H-imidazol-1-yl]methyl]-2-benzofuranyl]phenyl]tetrazole Intermediate 11 (0.5 g) was added to tri-n-butyl-tin azide (3 g) at 160° C. with stirring under nitrogen. The mixture was stirred at 160° C. for 1 h. The resulting solution was cooled to room temperature before being basified with 5N NaOH. The resultant solid was dissolved in methanol and acidified to pH2 using concentrated HCl. The aqueous layer was extracted with ethyl acetate (3×20 ml). The combined organic phases were dried and evaporated to give an orange solid (0.35 g) which was purified by reverse phase h.p.l.c. (acetonitrile/water/TFA) to give the title compound (0.125 g) as a white powder m.p. 193°–197° C.

Assay found: C,52.2;H,3.9;N.15.0 $C_{24}H_{22}BrClN_6O_2 0.1C_2HF_3O_2$ requires: C,52.5;H,4.0;N,15.2%.

EXAMPLE 4

1-[[3-Bromo-2-[2-(1H-tetrazol-5-yl)phenyl]-5-benzofuranyl]methyl]-2-butyl-4-chloro-1H-imidazole-5-carboxaldehyde A mixture of Intermediate 17 (180 mg), water (5 ml), THF (10 ml) and concentrated hydrochloric acid (0.1 ml) was stirred overnight, after which time a further addition of concentrated hydrochloric acid (0.2 ml) was made. Stirring was continued for 3 days, concentrated hydrochloric acid (0.2 ml) was added and after a further 2 days stirring, sodium hydroxide solution (2N) was added to bring the solution to ca. pH 12. Most of the solvent was removed in vacuo and the residue diluted with water and extracted with ether. The aqueous phase was then acidified with dilute hydrochloric acid (2N) to about pH 3 and extracted with ethyl acetate. The organic extracts were combined, backwashed with water and brine, dried and concentrated in vacuo to a white foam (12 1 mg). 100 mg were purified by preparative HPLC to give the title compound as a white solid (60 mg) m.p. 122°–124° C.

T.l.c. ether/acetic acid (100:1), Rf 0.7.

EXAMPLE 5

1-[[3-Bromo-2-[2-(1H-tetrazol-5-yl)phenyl]-5-benzofuranyl]methyl]-2-butyl-4-chloro-1H-imidazole-5-carboxylic acid A mixture of Intermediate 18 (2.9 g), methanol (50 ml) and concentrated hydrochloric acid (0.5 ml) was stirred at room temperature for 1.5 h, after which time sodium hydroxide solution (2N) was added to take the solution to about pH 12. Most of the solvent was removed in vacuo and the residue was diluted with water and extracted with ether. The aqueous phase was acidified with dilute hydrochloric acid (2N) to about pH 3 and extracted with ethyl acetate. The organic extracts were combined, backwashed with water and brine, dried and concentrated in vacuo to a white foam, which was triturated with ether to give the ethanol solvate of the title compound as a white solid (1.22 g), m.p. 183°–185° C.

I.r. (Nujol mull, cm$^{-1}$) 1709, 1529, 1464, 1420, 1377, 1364, 1265, 1142, 1069, 1059, 1043, 780.

Column chromatography of the title compound eluting with System E (75:25:1) provided the non-solvated title compound as a white solid.

I.r. (Nujol mull, cm$^{-1}$) 1709, 1520, 1466, 1452, 1370, 1359, 1281, 1261, 1248, 1222, 1145, 1090, 1072, 999, 985, 775, 767,748.

EXAMPLE 6

5-[2-[3-Bromo-5-[(2-butyl-1H-imidazol-1-yl)methyl]-2-benzofuranyl]phenyl]-1H-tetrazole A suspension of Intermediate 19 (1.4 g) in methanol (80 ml) was treated with concentrated hydrochloric acid (0.8 ml) and the mixture stirred for 18 h. The pH of the reaction mixture was adjusted to about 10 with 2N sodium hydroxide solution and then the methanol removed in vacuo. The residue was diluted with water and washed with ether. The aqueous phase was neutralised with saturated ammonium chloride solution and then extracted with ethyl acetate. The combined ethyl acetate extracts were washed with brine, dried and concentrated to give the title compound a white solid (322 mg).

T.l.c. System C (3:2) Rf 0.1. Found C,56.4; H,4.3;N,16.85. $C_{23}H_{24}BrN_6O 0.7H_2O$ requires C,56.4;H,4.6;N,17.15%.

EXAMPLE 7

5-[2-[5-[[2-Butyl-4-chloro-5-(hydroxymethyl)-1H-imidazol-1-yl]methyl-2-benzofuranyl]phenyl]-1H-tetrazole A suspension of Intermediate (21) (0.27 g) in tri-n-butyl tin azide (2.5 g) was heated to ~150° C. After 1.5 h, the resulting dark solution was cooled to room temperature and diluted with aqueous sodium hydroxide (1M, 50 ml) and this was further diluted with water to give an orange solution. This was washed with ether (5×50 ml) before acidification to about pH2 using 2N HCl. The resulting suspension was extracted into dichloromethane (4×50 ml) and the combined organic extracts dried, filtered and evaporated to give an orange gum (0.38 g). Purification by reverse phase hplc gave the title compound as a pale orange solid (0.117 g).

m.p. 220°–225° C. hplc, Dynamax $C_{18}$ 60 Å 8 μ, 25cm ×41.4i.d. column, mobile phase: acetonitrile/water (containing 0.1% TFA), 9 to 81% acetonitrile over 25 mins. Detection λ230 nm. Retention time =17.8 minutes.

EXAMPLE 8

2-[3-Bromo-5-[[2-butyl-4-chloro-5-(hydroxymethyl)-1H-imidazol-1yl]methyl]-2-benzofuranyl]benzoic acid A solution of Intermediate 22 (270 mg) in sodium hydroxide solution (2N, 2 ml) and methanol (10 ml) was stirred at room temperature for 42 h. The reaction mixture was diluted with water, acidified with dilute hydrochloric acid to about pH 7 and the precipitate was collected and dried in a vacuum oven at 50° C. overnight. The title compound was obtained as a cream solid (210 mg). m.p. 145° C.

T.l.c. ether/acetic acid 100: 1, Rf 0.59.

EXAMPLE 9

5-[2-[5-[[2-Butyl-4-chloro-5-(hydroxymethyl)-1H-imidazol-1-yl]methyl]-3-methyl-2-benzofuranyl]-phenyl]-1H-tetrazole A solution of Intermediate (26) (0.63 g) in methanol (10 ml) was treated with 2N HCl (5 ml) and stirred at room temperature for ~60 h. The reaction mixture was neutralised to pH7 with 2N NaOH and extracted with ethyl acetate (4×15 ml). The combined organic extracts were dried, filtered and evaporated to give an orange gum. This was further purified by hplc to give the title compound (0.02 g) as a white powder.

hplc, (conditions as in Example 7) Retention time =18.1 minutes. n.m.r (DMSO $d_6$)7.8 δ(1H,brd),7.7–7.8 δ(2H,m), 7.7 δ(1H,ddd), 7.3–7.4 δ(2H 2×d),7.0 δ(1H, brd),5.3 δ(2H,s),4.35 δ(2H,s), 2.5 δ2H,t),1.9 δ(3H,s),1.45 δ(2H,m),1.2 δ(2H,m),0.8 δ(3H,t).

EXAMPLE 10

5-[2-[5-[[2-Butyl-4-chloro-5-(hydroxymethyl)-1H-imidazol-1-yl]methyl]-3-methoxy-2-benzofuranyl]-phenyl]-1H-tetrazole A mixture of tri-n-butyl tin azide (0.37 g) and Intermediate (29)(0.23 g) was heated at 100° C. for 1 h. The residue was taken up in methanol (4 ml) and then added to sodium hydroxide solution (2N, 20 ml). The aqueous phase was washed with ether (2×20 ml) then acidified to pHl with conc. hydrochloric acid. The mixture was extracted with dichloromethane (3×20 ml) and the combined extracts dried and evaporated to give a brown solid. The solid was purified by hplc to afford an off-white solid (30 mg). m.p. 179°–181° C. (dec).

n.m.r (CDCl$_3$+1 drop DMSO $d_6$)7.9 δ(1H, brd), 7.7–7.8 δ(2H, m),7.65 δ(1H,brt), 7.6 δ(1H,brs),7.4 δ(1H,d),7.1 δ(1H, brd),5.4 δ(2H,s), 4.4 δ(2H,s). 3.7 δ(3H, s). 2.55 δ(2H, t),1.48 δ(2H,m),1.3 δ(2H,m),0.8 δ(3H,t).

EXAMPLE 11

Methyl 1-[[3-bromo-2-[2-(1H-tetrazol-5-yl)phenyl]-5-benzofuranyl]methyl]-2-butyl-4-chloro-1H-imidazole-5-carboxylate Intermediate 30 (350 mg) was added to methanol (10 ml) and concentrated HCl (0.1 ml) and the mixture stirred at room temperature for 3 h. A further addition of concentrated HCl (0.1 ml) was made and stirring continued for 1 h. Sodium hydroxide solution (2N) was added to ca pH 12, and most of the solvent evaporated in vacuo. The residue was partitioned between water and ether and the aqueous layer was further extracted with ether, acidified with HCl (2N) to ca pH 3, and extracted with ethyl acetate. The organic extracts were combined, backwashed with water and brine, dried, and concentrated in vacuo to a white foam. This was purified by chromatography, eluting with System E (100:5:1) to give the title compound (204 mg) as a white foam. m.p. 110°–112° C.

T.l.c. System E (100:5:1) Rf 0.31.

EXAMPLE 12

Ethyl 1 -[[3-bromo-27-[2-(1H-tetrazol-5-yl)phenyl]-5-benzofuranyl]methyl]-2-butyl-4-chloro-1H-imidazole-5-carboxylate A mixture of Intermediate 31 (0.5 g), ethanol (15 ml)and concentrated HCl (0.15 ml) was allowed to stir at room temperature for 2 h, after which time sodium hydroxide solution (2N) was added to adjust the mixture to ca pH 9. Most of the solvent was removed in vacuo and the residue diluted with water and extracted with ether. The aqueous phase was acidified with dilute HCl (2N) to ca pH 3 and extracted with ethyl acetate. The organic extracts were combined, backwashed with water and brine, dried and concentrated in vacuo to a white foam (272 mg). This was purified by chromatography, eluting with System E (100:5:1) to give the title compound as a white foam (181 mg). m.p. 99°–101° C.

T.l.c. System E (100:5:1) Rf 0.32.

EXAMPLE 13

Butyl 1-[[3-bromo-2-[2-(1H-tetrazol-5-yl)phenyl]-5-benzofuranyl]methyl]-2-butyl-4-chloro-1H -imidazole-5 -carboxylate Intermediate 32 (470 mg) was added to n-butanol (10 ml) and concentrated HCl (0.2 ml) and the mixture stirred at room temperature for 3 days. Sodium carbonate solution (1N) was added to ca pH 10, and most of the solvent removed in vacuo. The residue was partitioned between water and ether. HCl (2N) was added such that the aqueous layer was ca pH 2. The organic layer was separated and added to water containing 1N sodium carbonate solution to ca pH 12. The aqueous layer was acidified to ca pH 3 with HCl (2N) and extracted with ethyl acetate. The organic extracts were combined, dried and concentrated in vacuo to give the title compound as a white foam (263 mg). m.p. 88°–90° C.

T.l.c. System E (100:5:1) Rf0.48.

Example 14

2-Butyl-4-chloro-1-[[2-[(1H-tetrazol-5-yl)phenyl]-5-benzofuranyl]methyl]-1H-imidazole-5-carboxylic acid A solution of Intermediate 18 (0.517 g) in dry THF (20 ml) was cooled to −70° C. and treated dropwise with n-butyl lithium (0.86 ml; 1.51M). After stirring at −70° C. for 20 min methanol (>5 ml) was added. The solution was warmed to room temperature and the solvent evaporated. The residue was partitioned between saturated aqueous ammonium chloride (50 ml) and ethyl acetate (25 ml) and the aqueous solution extracted with ethyl acetate (3×20 ml). The combined organic phases were dried, filtered and evaporated to give a foam (0.46 g). This was dissolved in methanol (10 ml) and treated with concentrated HCl (0.25 ml). The resulting solution was stirred at room temperature for 3 h before basification to pH~12 and evaporation of the solvent. The resulting aqueous phase was washed with ether (3×20 ml) before acidification with 2N HCl to pH~2. The resulting suspension was extracted into ethyl acetate (3×20 ml) and the combined organic phases dried, filtered and evaporated to give a white powder. This was crystallised from ethanol to give the title compound as a white powder (0.14 g). m.p. 209°–210° C.

Assay requires C,60.4;H,4.4;N.17.6 $C_{24}H_{21}ClN_6O_3$ found C,60.45;H,4.45;N17.4%

EXAMPLE 15

Ethyl 1-[[3-bromo-2-[2-(1H-tetrazol-5-yl)phenyl]-5-benzofuranyl]methyl]-2-but-1(E)-enyl-4-chloro-1H-imidazole-5-carboxylate To a solution of Intermediate 34 in ethanol (10 ml) and THF (5.0 ml) was added concentrated HCl (0.1 ml) and the resultant solution stirred at room temperature for 1 h. Sodium bicarbonate (1% aqueous) was added to pH 8.5 and then the mixture was extracted into ether (35 ml) and the organic layer dried and concentrated in vacuo. The residue was purified by chromatography eluting with System E (100:10:1) to afford the title compound (45.5 mg) as a white solid.

T.l.c. System E (100:10:1) Rf 0.72 n.m.r δ(250 MHz, CDCl₃)0.92 (3H,t),2.0 (2H,quin),4.2(2H,q),5.57(2H,s),5.91(1H,d),6.68 (1H,dt),7.0 (1H,dd),7.08 (1H,s), 7.2 (1H,d),7.62 (2H,m), 7.88(1H,dd),8.0 (1H,dd).

EXAMPLE 16

1-[[3-Bromo-2-[2-(1H-tetrazol-5-yl)phenyl]-5-benzofuranyl]-methyl]-2-but-1(E)-enyl-4-chloro-1H-imidazole-5-carboxylic acid A solution of potassium hydroxide (8.7 mg) in ethanol (3 10 μl) was added to the product of Example 15 (45.0 mg) in water (69 μl) and the resultant solution stirred at room temperature for 18 h. HCl (2N aq) was added to pH 2.5 and then water (2 ml) added and the resultant mixture extracted into ethyl acetate (2×3 ml). The organic phases were dried and concentrated in vacuo to afford the title compound as a pale yellow solid (16.6 mg).

T.l.c System E (100:10:1) Rf 0.51 n.m.r. δ(250 MHz, MeOD)0.95 (3H,t),2.18 (2H,quin),5.70 (2H,s),6.35 (1H,dt),6.79 (1H,dt),7.05 (1H,dd),7.11 (1H,s),7.25 (1H,d),7.62 (1H,m),7.8 (2H,m).

EXAMPLE 17

1-[[3-Bromo-2-[2-(1H-tetrazol-5-yl)phenyl]-5-benzofuranyl]methyl]-4-chloro-2-propyl-1H-imidazole-5-carboxylic acid A suspension of Intermediate 36 (380 mg) in methanol (40 ml) was treated with concentrated HCl (0.3 ml) and the mixture stirred for 4 h. The reaction mixture was adjusted to ca pH 10 with 2N sodium hydroxide solution and then the methanol removed in vacuo. The residue was diluted with water and the aqueous solution extracted with ether. These ether extracts were discarded. The aqueous phase was acidified to pH 1 with dilute HCl solution and then extracted with ethyl acetate. The combined ethyl acetate extracts were washed with brine, dried and concentrated to give a white foam. Recrystallisation from ethanol gave the title compound as a white powder (163 mg), m.p 167°–171° C.

T.l.c. (ether:acetic acid; 100:1) Rf=0.5

EXAMPLE 18

Diethyl 1-[[3-bromo-2-[2-(1H-tetrazol-5-yl)phenyl]-5-benzofuranyl]methyl]-2-butyl-1H-imidazole-4,5-dicarboxylate Sodium hydride (60% dispersion, 140 mg) was added to a solution of Intermediate 38 (951 mg) in DMF (40 ml) and the resultant mixture stirred at room temperature for 15 mins prior to the addition of Intermediate 15 (3 g) in 3 portions over 20 mins and then the resultant mixture was stirred at room temperature for 72 h. The solvent was removed in vacuo and the residue dissolved in ethyl acetate (30 ml) and water (30 ml). The separated aqueous phase was extracted into ethyl acetate (2×20 ml) and then the combined organic phases dried and concentrated in vacuo. Purification by chromatograpahy eluting with petroleum ether:ether (9:1) followed by 10% methanol in ether gave the crude adduct which on recrystallisation from 15% aqueous ethanol and chromatography eluting with System E gave the title compound (137 mg).

T.l.c. System E Rf 0.51 n.m.r δ(250 MHz, CDCl₃)0.82 (3H,t),1.20 (6H,t),1.27 (2H,sex),1.52 (2H,quin), 2.3 (2H,t),4.09 (2H,q),4.19 (2H,q),5.4 (2H,s),6.93 (1H,dd),7.13 (1H,s), 7.30 (1H,d),7.65 (2H,m),7.82 (1H,dd),8.1 (2H,dd).

EXAMPLE 19

1-[[3-Bromo-2-[2-(1H-tetrazol-5-yl)phenyl]-5-benzofuranyl]methyl]-2butyl-1H-imidazole-4,5-dicarboxylic acid A mixture of the product of Example 18 (117 mg), potassium hydroxide (31.6 mg), ethanol (1.14 ml) and water (253 μl) were stirred at room temperature for 18 h prior to acidification to pH 4 (2N HCl). The resultant mixture was extracted into ethyl acetate (3×10 ml) and the combined organic phases dried and concentrated in vacuo to afford the title compound (73 mg) as a white solid.

T.l.c System E (100:10:1) Rf 0.05 n.m.r δ(250 MHz, MeOD)0.80(3H,t),1.35(4H,m),3.0(2H,m),6.1(2H,s),7.25- (1H,q),7.4(2H,m),7.71 (2H,m),7.85(1H,m),7.92(1H,dd).

EXAMPLE 20

5-[2-[3-Bromo-5-[[2-butyl-4-chloro-5-(methoxymethyl)-1H-imidazol-1-yl]methyl]-2-benzofuranyl]phenyl]-1H-tetrazole A mixture of the product of Example 3 (780 mg), concentrated sulphuric acid (1.5 ml), and methanol (20 ml) was heated at reflux overnight. The reaction mixture was cooled and the solvent removed in vacuo. The residue was diluted with water, sodium hydroxide solution (2N) was added to pH 3, and this was extracted with ethyl acetate. The organic extracts were combined, backwashed with brine, dried and concentrated in vacuo to a buff-coloured solid which was triturated with ether, and recrystallised from ethanol to give the title compound as an off-white solid (217 mg). m.p. 213°–215° C.

T.l.c. dichloromethane/methanol (10:1) Rf 0.47.

EXAMPLE 21

1-[[2-[(1H-Tetrazol-5-yl)phenyl]-3-(trifluoromethyl)-5-benzofuranyl]methyl]-2-butyl-4-chloro-1H-imidazole-5-carboxylic acid A solution of Intermediate 46 (0.5 g) in methanol (15 ml) was treated with concentrated HCl (0.25 ml) and the solution stirred at room temperature. for 48 h. 2N NaOH was added to pH~12 and the solvent evaporated. The residue was partitioned between water (50 ml) and ether (50 ml) and the aqueous solution washed with further ether (4×25 ml) before acidification to pH~2 using 2N HCl. The milky suspension was extracted with ethyl acetate (3×30 ml) and the combined organic phases dried, filtered and evaporated to give an off-white foam. Re-evaporation from System A (1:1) gave the title compound as a white powder (0.32 g). m.p. 149°–151° C. decomp.

h.p.l.c. (conditions as in Example 53) Retention Time=23.83 mins

EXAMPLE 22

1-[[2-[2-Bromo-6-(1H-tetrazol-5yl)phenyl]-5-benzofuranyl]methyl]-2butyl-4-chloro-1H-imidazole-5-carboxylic acid A mixture of Intermediate 50 (426 mg) and tri-n-butyl tin azide (500 mg) was stirred 160° C. for 2 h under nitrogen. The brown solution was allowed to cool to 60° C. before adding aqueous sodium hydroxide (0.5M, 30 ml). The mixture was stirred until the brown gummy solid had dissolved and then washed with ethyl acetate (2×50 ml). The turbid solution was filtered and then acidified with aqueous HCl (to pHl; 2M, 10 ml). The product was collected by filtration and dried in vacuo to give the title compound as a white powder (213 mg), m.p. 150°–160° C. (dec.).

n.m.r. δ(D$_6$-DMSO)8.07 (1H,dd),7.91 (1H,dd),7.69 (1H,t),7.50 (1H,d),7.23(1H,d),7.05 (1H,dd),6.92 (1H,s),5.69 (2H,s),2.66 (2H,t),1.55 (2H,m),1.29(2H,m),0.80 (3H,t)

EXAMPLE 23

1-[[3-Bromo-2-[2-(1H-tetrazol-5-yl)phenyl]1-5-benzofuranyl]methyl]-2-butyl-4-chloro-1H-imidazole-5-carboxylic acid, 1-(acetyloxy)methyl ester To a suspension of Intermediate 51 (400 mg) in ethanol (30 ml) was added concentrated HCl (0.1 ml) and the mixture stirred at room temperature for 3 h. The reaction mixture was basified with dilute sodium bicarbonate solution and then extracted with ether. These ethereal extracts were discarded. The aqueous phase was neutralised with saturated ammonium chloride solution and then extracted with ethyl acetate. The combined organic extracts were washed with brine, dried and concentrated to give a colourless oil. This oil was triturated with ether and filtered to give the title compound as a white powder (72 mg). m.p. 136°–140° C.

T.l.c. (Ether) Rf=0.4.
Similarly prepared

EXAMPLE 24

1-[[3-Bromo-2-[2-(1H-tetrazol-5-yl)phenyl]-5-benzofuranyl]methyl]-2-butyl-4-chloro-1H-imidazole-5-carboxylic acid, 1-(acetyloxy)ethyl ester as a colourless foam (233 mg).

T.l.c. (ether). Rf=0.5. From Intermediate 52 (0,484 g) in ethanol (30 ml) containing concentrated HCl (0.1 ml).

Example 25

Benzoyloxymethyl 1-[[3-bromo-2-[2-(1H-tetrazol-5-yl)phenyl]-5-benzofuranyl]methyl]-2-butyl-4-chloro-1H-imidazole-5-carboxylate Intermediate 53 (1.0 g) was dissolved in a 1M solution of HCl in methanol and the resultant solution was stood at room temperature for 22 minutes. It was then poured into sodium hydrogen carbonate (8%, 20 ml), washed with ether (1×50 ml, 2×25 ml) and the aqueous phase then acidified to pH3 using 2N HCl. The mixture was extracted with ethyl acetate (1×50 ml, 2×25 ml) and the combined extracts were dried filtered and evaporated to give the title compound as a white foam (488 mg).

I.r. 3200–2300cm$^{-1}$ (NH,broad), 1737cm$^{-1}$ (ester CO) n.m.r. δ(CDCl$_3$)8.07(1H,m),7.94(2H,dd),7.84(1H,m),7.67(2H,m),7.55(1H,t), 7.39(2H,t),7.23(1H,d),6.99(2H,m),6.03(2H,s),5.54 (2H,s),2.26(2H,t), 1.48(2H,m),1.20(2H,m),0.80(3H,t).

Similarly prepared

EXAMPLE 26

1-(Ethoxycarbonyloxy)ethyl 1-[[3-bromo-2-[2-(1H-tetrazol-5-yl)phenyl]-5-benzofuranyl]methyl]-2-butyl-4-chloro-1H-imidazole-5-carboxylate as a white solid (450 mg).

I.r. 3200–2400cm$^{-1}$ (NH), 1758cm$^{-1}$ (carbonate CO), 1717cm$^{-1}$ (ester CO) δn.m.r δ(CDCl$_3$)8.06 (1H,dd),7.87 (1H,dd),7.66 (2H,m),7.30 (1H,d),7.06 (1H,d),6.96 (1H,dd),6.80 (1H,q),5.63 and 5.50 (2H,AB system),4.14 (2H,q), 2.34(2H,t), 1.54 (3H,d),1.52 (2H,m),1.25 (3H,t),1.24 (2H,m),0.82 (3H,t).

From Intermediate 54 (1.0 g), and a 1M solution of HCl in methanol (10 ml).

EXAMPLE 27

[4-(Aminocarbonyl)phenyl]methyl 1-[[3-bromo-2-[2-(1H-tetrazol-5-yl)phenyl]-5-benzofuranyl]methyl]-2-butyl-4-chloro-1H-imidazole-5-carboxylate as an off-white solid (70 mg) m.p. 152°–156° C.

Assay Found: C,54.22;H,3.90;N,13.44% C$_{32}$H$_{27}$BrClN$_7$O$_4$ required C,55.7;H,3.95;N,14.2%

From Intermediate 55 and a 1M solution of HCl in methanol (5 ml).

EXAMPLE 28

2-(N,N-Dimethylaminoethyl)-1-[[3-bromo-2-[2-(1H-tetrazol-5-yl)phenyl]-5-benzofuranyl]methyl]-2-butyl-4-chloro-1H-imidazole-5-carboxylate A solution of Intermediate 56 (904 mg) in methanolic HCl (1M, 10 ml) was stood at room temperature for 30 mins. Water (50 ml) and ethyl acetate (50 ml) were added and the aqueous phase extracted, washed with ethyl acetate (50 ml) and saturated ammonium chloride (70 ml) added. The solution was brought to pH6 with aqueous sodium hydroxide (2M, ~5 ml) and then extracted with ethyl acetate (50 ml). The organic extract was dried, filtered and concentrated in vacuo to give a foam which was triturated with ether (10 ml) to give the title compound as a white powder (115 mg), m.p. 65°–70° C. (dec).

T.l.c. (ethyl acetate) Rf 0.05 streak
Similarly prepared

EXAMPLE 29

2,3-Dihydroxypropyl 1-[[3-bromo-2-[2-(1H-tetrazol-5-yl)phenyl]-5-benzofuranyl]methyl]-2-butyl-4-chloro-1H-imidazole-5-carboxylate as a pale yellow foam (457 mg)

T.l.c. ether: trifluoroacetic acid (100:1), Rf 0.1 I.r. 3600–2600 cm$^{-1}$ (NH,OH), 1707 cm$^{31}$ $^1$ (ester CO)

From Intermediate 57 (1.98 g) and a 1M solution of HCl in methanol (20 ml).

EXAMPLE 30

2-Methoxyethyl 1-[[3-bromo-2-[2-(1H-tetrazol-5-yl)phenyl]-5-benzofuranyl]methyl]-2-butyl-4-chloro-1H-imidazole-5-carboxylate Concentrated HCl (0.1 ml) was added to a solution of Intermediate 58 (25 1 mg) in 2methoxyethanol (4 ml) and the mixture stirred overnight at room temperature. The solution was purified by chromatography on silica (Sorbsil 60) eluting with dichlormethane/methanol (30:1) to give the title compound as a colourless foam (0.12 g).

Analysis Found: C,52.4;H,4.3;N,13.1 C$_{27}$H$_{25}$BrClN$_6$O$_4$ requires C,52.9;H,4.1;N,13.7%. T.l.c. dichloromethane/methanol (30:1). Rf=0.2.

EXAMPLE 31

1-Methylethyl1-[[3-bromo-2-[2-(1H-tetrazol-5-yl)phenyl]-5-benzofuranyl]methyl]-2-butyl-4-chloro-1H-imidazole-5-carboxylate To Intermediate 59 (770 mg) was added propan-2-ol (15 ml) and concentrated HCl (0.3 ml). After stirring for 3 h further quantities of isopropanol (5 ml) and concentrated HCl (0.1 ml) were added and stirring continued overnight. Sodium carbonate solution (1N) was added to ca pH 11, and most of the solvent removed in vacuo. The residue was partitioned between water and ether. The aqueous layer was further extracted with ether, acidified with dilute HCl (2N) to ca pH 1, and then extracted with ethyl acetate. The organic extracts were combined, backwashed with brine, dried and concentrated in vacuo to a pale yellow gum. This was purified by chromatography eluting with System E (100:5:1) to give the title compound as a white foam (273 mg). m.p. 105°–106° C.

T.l.c. System E (100:5:1) Rf 0.24.

EXAMPLE 32

1-[[3-Bromo-2-[2-(1H-tetrazol-5-yl)phenyl]-5-benzofuranyl]methyl]-2-butyl-4-chloro-1H-imidazole-5-carboxamide To Intermediate 60 (240 mg) was added methanol (10 ml) and concentrated HCl (0.2 ml). After stirring at room temperature for 3 h, sodium hydroxide (2N) was added to ca pH 12, and then most of the solvent removed in vacuo. The residue was partitioned between water and ether. The aqueous layer was further extracted with ether, acidified with dilute HCl (2N) to ca pH 2 and then extracted with ethyl acetate. The organic extracts were combined, backwashed with brine, dried and concentrated in vacuo to a white foam. This was purified by chromatography, eluting with System E (75:25:1, to give the title compound as a white foam (131 mg). m.p. 131°–133° C.

T.l.c. System E (75:25:1) Rf 0.26.

EXAMPLE 33

1-[[1-[[3-Bromo-2-[2-(1H-tetrazol-5-yl)phenyl]-5-benzofuranyl]methyl]-2-butyl-4-chloro-1H-imidazol-5-yl]carbonyl]pyrrolidine To Intermediate 61 (1.2 g) was added methanol (40 ml) and concentrated HCl (0.1 ml). After stirring at room temperature for 4 h, sodium hydroxide (2N) was added to ca pH 12 and then most of the solvent removed in vacuo. The residue was partitioned between water and ether. The aqueous layer was further extracted with ether, acidified with dilute HCl (2N) to ca pH 1 and then extracted with ethyl acetate. The organic extracts were combined, backwashed with brine, dried and concentrated in vacuo to give the title compound as a white foam (834 mg). m.p. 120°–122° C.

T.l.c. System E (75:25:1), Rf 0.25.
Similarly prepared

EXAMPLE 34

1-[[3-Bromo-2-[2-(1H-tetrazol-5-yl)phenyl]-5-benzofuranyl]methyl]-2-butyl-4-chloro-N-methyl-1H-imidazole-5-carboxamide as a white foam (9 15 mg) m.p. 218°–220° C.

T.l.c. System E (75:25:1) Rf 0.34.

From Intermediate 62 (1.32 g) in a solution of HCl (1 ml) in methanol (40 ml).

EXAMPLE 35

1-[[3-bromo-2-[2-(1H-tetrazol-5-yl)phenyl]-5-benzofuranyl]methyl]-2-butyl-4-chloro-N,N-dimethyl-1H-imidazole-5-carboxamide as a white foam (754 mg) m.p. 216°–218° C.

T.l.c. System E (75:25:1) Rf 0.28.

From Intermediate 63 (1:15 g) in a solution of HCl in methanol (40 ml).

EXAMPLE 36

1 -[[3-Bromo-2-[2-(1H-tetrazol-5-yl)phenyl]-5-benzofuranyl]methyl]-2-butyl-4-chloro-N-methyl-1H-imidazole-5-acetamide as a white solid (70.7 mg). T.l.c ether:methanol (98:2) Rf=0.10 n.m.r. δ(250 MH$_z$, CDCl$_3$),0.85(3H,t),1.20(2H,t),1.50(2H,t), 2.40(2H,t),2.55(3H,d),3.28(2H,s),5.20(2H, s),5.75(1H,q), 6.90(1H,dd),7.02(1H,s),7.25(1H,m),7.65(1H,m),7.85(1H,m),8.10(1H,m).

From Intermediate 64 (111 mg) in a solution of HCl (0.1 ml) in methanol (5 ml).

EXAMPLE 37

1-[[3-Bromo-2-[2-(1H-tetrazol-5-yl)phenyl]-5-benzofuranyl]methyl]-2-butyl-4-chloro-N-ethyl-1H-imidazole-5-carboxamide as a white solid (655 mg).

T.l.c ether Rf=0.17 Analysis Found C,53.4;H,4.5;N,16.95 C$_{26}$H$_{25}$N$_7$O$_2$ClBr C,53.6;H,4.3;N,16.8%

From Intermediate 65 (1.0 g) in a solution of HCl (0.5 ml). in methanol (30 ml)

EXAMPLE 38

1-[[3-Bromo-2-[2-(1H-tetrazol-5-yl)phenyl]-5-benzofuranyl]methyl]-4-chloro-2-ethyl-1H-imidazole-5-carboxylic acid as a white solid (507 mg), m.p. 158°–160° C.

T.l.c System E (75:25:1) Rf=0.25

From Intermediate 70 (1.0 g) in a solution of HCl (0.6 ml) in methanol (30 ml).

EXAMPLE 39

1-[[3-Bromo-2-[2-(1H-tetrazol-5-yl)phenyl]-5-benzofuranyl]methyl]-4-chloro-2-ethyl-N-methyl-1H-imidazole-5-carboxamide (255 mg).

T.l.c. ether Rf=0.13 I.r (Nujol) 3200–2730, 1652, 1546 and 1462 cm$^{-1}$.

From Intermediate 71 (440 mg) in a solution of HCl (0.4 ml) in methanol (20 ml).

EXAMPLE 40

1 -[[3-Bromo-2-[2-(1H-tetrazol-5-yl)phenyl]-5-benzofuranyl]methyl]-2-butyl-1H-imidazole-5-carboxylic acid (106 mg) m.p. 182°–184° C.

T.l.c. dichloromethane/methanol/acetic acid (10:1:1) Rf 0.33

From Intermediate 75 (430 mg) in a solution of HCl (0.4 ml) in methanol (15 ml).

EXAMPLE 41

1-[[3-Bromo-2-[2-(1H-tetrazol-5-yl)phenyl]-5-benzofuranyl]methyl]-2butyl-1H-imidazole-4-carboxylic acid as a buff-coloured solid (186 mg) m.p. 170°–172° C.

T.l.c. dichloromethane/methanol/acetic acid (10:1:1) Rf 0-31

From Intermediate 76 (420 mg) in a solution of HCl (0.4 ml) in methanol (15 ml).

EXAMPLE 42

1-[[3-Bromo-2-[2-(1H-tetrazol-5-yl)phenyl]-5-benzofuranyl]methyl]-4-chloro-2-propyl-N-methyl-1H-imidazole-5-carboxamide as a white solid (880 mg) m.p. 109°–116° C.

T.l.c. ether:acetic acid (100:1) Rf=0.36. From Intermediate 77 (1.4 g) in a solution of HCl (1 ml) in methanol (60 ml).

EXAMPLE 43

1 -[[3-Bromo-2-[2-(1H-tetrazol-5-yl)phenyl]5-benzofuranyl]methyl]-2-butyl-4-chloro-N-isopropyl-1H-imidazole-5-carboxamide (0.74 g).

T.l.c ether Rf=0.17 Analysis found C,54.3;H,4.6;N,16.4. $C_{27}H_{27}N_7O_2$ ClBr requires C,54.3;H,4.5;N,16.1%

From Intermediate 78 (1.15 g) in a solution of HCl (0.5 ml) in methanol (35 ml).

EXAMPLE 44

1-[[3-Bromo-2-[2-(1H-tetrazol-5-yl)phenyl]-5-benzofuranyl]methyl]-2-butyl-4-iodo-1H-imidazole-5-carboxylic acid as a white powder (350 mg) mp 184°–189° C.

T.l.c ether Rf=0.1

From Intermediate 82 (1.0 g) in a solution of HCl (0.1 ml) in methanol (30 ml).

EXAMPLE 45

1-[[3-Bromo-2-[2-(1H-tetrazol-5-yl)phenyl]-5-benzofuranyl]methyl]-2-butyl-4-trifluoromethyl-1H-imidazole-5-carboxylic acid as a white solid (12 mg) m.p 144°–149° C.

T.l.c. petroleum ether:ether (1:1) Rf=0.1.

From Intermediate 84 (210 mg) in a solution of HCl (0.1 ml) in ethanol (20 ml).

EXAMPLE 46

1-[[3-Bromo-2-[2-(1H-tetrazol-5-yl)phenyl]-5-benzofuranyl]methyl]-2butyl-4-methyl-1H-imidazole-5-carboxylic acid, hydrochloride (1:1) as a pale yellow powder (0.119 g) m.p. 179°14 181° C.

H.p.l.c. (conditions as in Example 53) R.T. 16.87 min

From Intermediate 86 (0.25 g) in a solution of HCl in methanol (10 ml).

EXAMPLE 47

3-Bromo-5-[[2-butyl-4,5-dichloro-1H-imidazol-1-yl]methyl]-2-[2-(1H-tetrazol-5-yl)phenyl]benzofuran trifluoroacetic acid salt Intermediate 88 (0.85 g) was suspended in methanol (25 ml) and treated with 2N hydrochloric acid (5 ml). THF (10 ml) was added and the suspension was stirred at room temperature for 62 h. The solvent was removed in vacuo to give a white solid which was partitioned between water (25 ml) and dichloromethane (4×15 ml). The combined organic extracts were dried and concentrated in vacuo to give a white solid which was dissolved in acetonitrile (10 ml) and trifluoroacetic acid (2 drops) added. The resultant precipitate was filtered to give the title compound (0.256 g) as a white solid, m.p. 197°–199°.

n.m.r. (DMSOd$_6$)7.75–8.0 δ(m,4H),7.58 δ(d,1H),7.27 δ(d,1H),7.13 δ(dd,1H),5.42 δ(brs,2H),2.69 δ(t,2H),1.55 δ(m,2H), 1.3 δ(m,2H), 0.85 δ(t,3H).

EXAMPLE 48

1-[[3-Bromo-2-[2-(1H-tetrazol-5-yl)phenyl]-5-benzofuranyl]methyl]-2-butyl-4-chloro-1H-imidazole-5-acetic acid A mixture of Intermediate 97 (130 mg) and glacial acetic acid:conc.HCl (1:1) (5 ml) was heated at reflux for 2.5 h. The solution was basified to pH 10 (5N, NaOH) and then extracted into ether (3×15 ml). The aqueous phase was acidified to pH 5 (2N HCl) and then extracted into ethyl acetate and the combined organic extracts dried and concentrated in vacuo to afford the title compound (83 mg) as a pale cream solid.

T.l.c petroleum ether:ether:acetate acid:methanol (50:50:1:1) Rf=0.07 n.m.r. δ(250 MHz, DMSO-d6)0.85 (3H,t),1.25 (2H,quin),1.51 (2H,sex)2.55 (2H, t),3.55 (2H,s),5.35 (2H,s),7.07 (2H, dd),7.2 (1H,d),7.5 (1H,d),7.78 (2H,m), 7.9 (1H,dd),7.98 (1H,m).

EXAMPLE 49

Ethyl 1-[[3-Bromo-2-[2-(1H-tetrazol-5-yl)phenyl]-5-benzofuranyl]methyl]-2-butyl-4-chloro-1H-imidazole-5-acetate A solution of the product of Example 48 (100 mg) in ethanol (10 ml) and conc.HCl (1 drop) was heated at reflux for 2 h after which time anhydrous magnesium sulphate (200 mg) was added and the reaction mixture heated at reflux for 7 h. The solids were removed by filtration and the filtrate concentrated in vacuo. The residue was purified by column chromatography eluting with dichloromethane:ethanol: acetic acid (96:2:2) to afford the rifle compound product as a colourless glass (14 mg).

T.l.c. dichloromethane:methanol (98:2) Rf=0.55 n.m.r. δ(CDCl$_3$ 250MHz),0.78 (3H,t),1.12 (3H,t),1.3 (4H,c),2.0 (2H,t), 3.33 (2H,S),4.0 (2H,q),5.15 (2H,s)6.95 (2H,m)7.30 (1H,m),7.65 (2H,t), 7.88 (1H,dd), 8.0 (1H,dd).

EXAMPLE 50

1-[6-[3-Bromo-2-[2-(1H-tetrazol-5-yl)phenyl]benzofuranyl]methyl]-2-butyl-4-chloro-1H-imidazole-5-carboxylic acid A mixture of Intermediate 94 (0.5 g) and tri-n-butyl tin azide (0.7 g) was stirred at 160° C. for 1.5 h. After cooling, the viscous gum was partitioned between 1N sodium hydroxide (20 ml) and ether (15 ml). The separated aqueous phase was further washed with ether (20 ml) then was acidified to pH1 with 2N hydrochloric acid. The resultant solid was filtered off and dried to give the title compound as a solid (383 mg) m.p. 132°–140° C. n.m.r. δ(DMSO)7.95 (m,1H),7.88 (m,1H),7.75 (m,2H),7.52 (d,1H),7.23(brs,1H),7.03 (dd,1H),5.72 (brs,2H),2.64 (t,2H),1.55 (m,2H),1.3(m,2H), 0.82(t,3H).

EXAMPLE 51

1-[[3-Bromo-2-[2-(ethoxycarbonyl)phenyl]-5-benzofuranyl]methyl]-2-butyl-4-chloro-1H-imidazole-5-carboxylic acid A solution of sodium chlorite (5.6 g) and sodium dihydrogen phosphate (5.6 g) in water (30 ml) was added to a mixture of Intermediate 102 (3.364 g), 2-methyl-2-butene (2N; 37 ml) and tert-butanol (40 ml) in THF (40 ml) at room temperature under nitrogen. The mixture was stirred for 2.5 h, then the organic solvent evaporated. The residue was extracted with ethyl acetate (3×50 ml), the combined extracts were washed with brine (1×100 ml) and dried. The solvent was evaporated and the residue purified by column chromatography eluting with System E (200:25:1) to give a foam which was dissolved in ethanol (10 ml). The title compound crystallised out as colourless microcrystals (2.7 g). m.p. 148°–150° C.

T.l.c System E (200:25:1) Rf=0.50

EXAMPLE 52

1-[[3-Bromo-2-(2-carboxyphenyl)-5-benzofuranyl]methyl]2-butyl-4-chloro-1H-imidazole-5-carboxylic acid Sodium hydroxide (89 mg) in water (0.2 ml) was added to a suspension of the product of Example 51 (0.5 g) in ethanol (5 ml). The solution was heated under reflux for 16 h, cooled, then evaporated in vacuo. The residue was dissolved in water (5 ml), and HCl (2N; 1 ml) was added dropwise resulting in the precipitation of the title compound which was filtered off, washed with water (2×5 ml) and dried to give the title compound as a colourless solid (391 mg). m.p. 148°–152° C.

T.l.c. System E (25:5:0.2) Rf=0.45.

EXAMPLE 53

N-[[1-[[3-Bromo-2-[2-(1H-tetrazol-5-yl)phenyl]-5-benzofuranyl]methyl]-2-butyl-4-chloro-1H-imidazol-5-yl]methyl]acetamide A solution of Intermediate 105 (375 mg) in methanolic hydrochloric acid (1M, 10 ml) was stood at room temperature for 3 h. Aqueous sodium hydroxide (2M, 6 ml) and water (20 ml) were added. The mixture was washed with ether (2×50 ml), and then acidified with aq. hydrochloric acid (2M, 10 ml). The turbid solution was extracted with ethyl acetate (20 ml) and the extract dried, filtered and evaporated in vacuo. Trituration with ether gave a white powder (218 mg), m.p. 148°–150° C. (dec.).

H.p.l.c. Dynamax-60A Solvent A: H₂O (0.05% TFA), Solvent B: acetonitrile: H₂O (9:1+0.05% TFA)

Gradient: 10–90% B in 25 mins Retention time=18.65 minutes

Similarly prepared

EXAMPLE 54

Methyl [[1-[[3-Bromo-2-[2-(1H-tetrazol-5-yl)phenyl]-5-benzofuranyl]methyl]-2-butyl-4-chloro-1H-imidazol-5-yl]methyl]carbamate as a white powder (275 mg) m.p. 183°–185° C.

h.p.l.c (conditions as in Example 53) Retention time=21.72 mins From a solution of Intermediate 106 (403 mg) in methanolic hydrochloric acid (1M, 10 ml).

EXAMPLE 55

N-[[1-[[3-Bromo-2-[2-(1H-tetrazol-5-yl)phenyl]-5-benzofuranyl]methyl]-2-butyl-4-chloro-1H-imidazol-5-yl]methyl]formamide as an off-white solid (91 mg) m.p. 148°–152° C.

h.p.l.c (conditions as in Example 53) Retention time=19.02 minutes From a solution of Intermediate 107 (397 mg) in methanolic hydrochloric acid (1M, 10 ml)

EXAMPLE 56

[[1-[[3-Bromo-2-[2-(1H-tetrazol-5-yl)phenyl]-5-benzofuranyl]methyl]-2-butyl-4-chloro-1H-imidazol-5-yl]methyl]urea as an off-white powder (91 mg) m.p. 206°–210° C.

h.p.l.c (conditions as in Example 53) Retention time=17.0 mins From a solution of Intermediate 108 (154 mg) in methanolic hydrochloric acid (1M, 6 ml)

EXAMPLE 57

1-[[3-(1,1-Dimethylethyl)-2-[2-(1H-tetrazol-5yl)-phenyl]-5-benzofuranyl]methyl]-2-butyl-4-chloro-1H-imidazole 5-carboxylic acid A suspension of Intermediate 114 (0.68 g) in n-butyl tin azide (4 g) was treated according to the method of Example 3 to give the title compound as a pale yellow powder (0.24 g). m.p. 129°–132° C.

h.p.l.c (conditions as in Example 53) Retention time=25.39 minutes

EXAMPLE 58

5-[2-[5-[2-Butyl-5-chloro-4-(hydroxymethyl)-1H-imidazol-1-yl]-3-[1, 1-(dimethylethyl)]-2-benzofuranyl]phenyl]tetrazole A suspension of Intermediate 115 (0.25 g) in n-butyl tin-azide (3 g) was treated according to the method of Example 3. Trituration with hexane gave the title compound as a pale yellow powder (0.087 g). m.p. 124°–127° C.

h.p.l.c (conditions as in Example 53) Retention time=21.10 minutes

EXAMPLE 59

1-[5-[3-Chloro-2-[2-(1H-tetrazol-5-yl)phenyl]benzofuranyl]methyl]-2-butyl-4-chloro-1H-imidazole-5-carboxylic acid Concentrated hydrochloric acid (1.5 ml) was added dropwise to a stirred mixture of Intermediate 118 (0.76 g) in methanol (40 ml). After stirring for 4.5 h, the solution was basified with 2N sodium hydroxide to pH 12 before being washed with ether (2×80 ml). The separated aqueous layer was acidified cautiously with concentrated hydrochloric acid before being extracted with ethyl acetate (2×80 ml). The combined organic extracts were dried and concentrated in vacuo to afford a yellow oil which was azeotroped with toluene (3×50 ml) and dried in vacuo 55° for 6 h to give the title compound (0.265 g) as a pale yellow solid, m.p. 117°–121°.
n.m.r. (DMSO)7.78–7.98 δ(m,3H),7.55 δ(d,1H),7.08–7.3 δ(m,3H),5.74 δ(brs,2H), 2,68 ε(t,2H),1.55 δ(m,2H),1.3 δ(m,2H),0.83 δ(t,3H).

EXAMPLE 60

Ethyl 1-[[3-bromo-2-[2-(1H-tetrazol-5-yl)phenyl]-5-benzofuranyl]methyl]-2-but-1(Z)-enyl-4-chloro-1H-imidazole-5-carboxylate A solution of Intermediate 120 (100 mg) and concentrated HCl (0.05 ml) in ethanol (5 ml) and THF (2 ml) was stirred at room temperature for 3 h. 1% Aqueous sodium hydrogen carbonate was added to pH 9 and the solvents were removed in vacuo. The crude isolate was purified by column chromatography eluting with System E (100:10:1) to afford the title compound (25 mg) as a white solid.

T.l.c petroleum ether:ether:acetic acid:methanol (100:100:1:1) Rf=0.59. n.m.r δ(CDCl$_3$, 250 MHZ),0.90 (3H,t),1.21 (3H,t),2.0 (2H, quin.),4.2 (2H,q), 5.57 (2H,d,J=16Hz),6.68 (1H, dt, J=16,7Hz),7.0 (1H,dd),7.09 (1H,s),7.25(1H,m),7.62 (2H,m),7.85 (1H,dd),8.0 (1H,dd).

Similarly prepared

EXAMPLE 61

Ethyl 1-[[3-bromo-2-[2-(1H-tetrazol-5-yl)phenyl]-5-benzofuranyl]methyl]-2-pent-1(Z)-enyl-4-chloro-1H-imidazole-5-carboxylate as a white solid (37 mg).
n.m.r δ(CDCl$_3$, 250 MHZ)0.9 (3H,t),1.30 (3H,t), 1.42 (2H, sex),2.59 (2H, dq), 4.27 (2H,q),5.7 (2H,s),6.11(1H,dt,J=12.7 Hz),6.3(1H,dt,J=12, Hz),7.0–8.0 (m,7H).

T.l.c petroleum ether:ether:acetic acid:methanol (100:100:1:1) Rf=0.61

From a solution of Intermediate 121 (100 mg) and concentrated HCl (0.05 ml) in ethanol (5 ml) and THF (2 ml).

EXAMPLE 62

1-[[3-Methoxy-2-[2-(1H-tetrazol-5-yl)phenyl]-5-benzofuranyl]methyl]-2-butyl-4-chloro-1H-imidazole-5-carboxylic acid A mixture of Intermediate 123 (380 mg) and tri-n-butyl tin azide (0.6 g) was treated according to the method of Example 3 to give the title compound as a white powder (180 mg) m.p. 140°–144° C.
Assay C,57.23;H,4.56;N,15.83% C$_{25}$H$_{23}$N$_6$O$_4$Cl.0.84-H$_2$O requires C,57.51;H,4.76;N,16.10% Water assay found 2.91% H$_2$O=0.84 mol H$_2$O

EXAMPLE 63

(±)2-Methoxy-1-methylethyl 1-[[3-bromo-2-[2-(1H-tetrazol-5-yl)phenyl]-5-benzofuranyl]methyl]-2-butyl-4-chloro-1H-imidazole-5-carboxylate A solution of Intermediate 124 (761 mg) in (+)-1-methoxypropan-2-ol (10 ml) and conc. hydrochloric acid (5 drops) was stood at room temperature for 2 h. Aqueous sodium bicarbonate (1%, 50 ml) was added and the mixture washed with ether (2×30 ml), before re-acidifying with hydrochloric acid (2M, pH1). The turbid solution was then extracted with ethyl acetate (20 ml), and the organic extract washed with hydrochloric acid (2M, 3×50 ml), dried, filtered and concentrated in vacuo to give an off-white foam (441 mg).
n.m.r.(d$_6$ DMSO)7.77–8.0 δ(4H,2×m), 7.55 δ(1H,d),7.20 δ(1H,d), 7.10 δ(1H,dd), 5.71 δ(2H,s),5.15 δ(1H,m), 3.4 δ(2H+H$_2$O,d), 3.22 δ(3H,s), 2.7 δ(2H,t),158 δ(2H,m),1.31 δ(2H,m),1.18 δ(3H,d),0.85 δ(3H). H.p.l.c. Dynamax -60A Solvent A: H$_2$O (0.05% TFA), Solvent B: CH$_3$CN:H$_2$O (9:1+0.05% TFA) 10–90% B in 25 mins; 90–100% B in 2 mins; 100–10% B in 4 mins Retention time=28.95 mins

EXAMPLE 64

1-[[3-Bromo-2-[2-(1H-tetrazol-5-yl)phenyl]-5-benzofuranyl]methyl]-2-butyl--5-chloro-imidazole-4-carboxylic acid A mixture of Intermediate 126 (91 mg) and tri-n-butyl tin azide (1.353 g) was treated according to the method of Example 3 to give the title compound (42 mg) as a white solid.
T.l.c. dichloromethane:ethanol:acetic acid (96:2:2) Rf=0.08 n.m.r δ(250 MHz CDCl$_3$+DMSO d$_6$)0.88(3H,t),1.32(2H sex)1.75(2H), 2.75(2H,t),5.28(2H,s),6.8–8.0(7H,m).

EXAMPLE 65

Ethyl 1-[[3-bromo-2-[2-[[(trifluoromethyl)sulphonyl]amino]phenyl]-5-benzofuranyl]methyl]-2-butyl-4-chloro-1H-imidazole-5-carboxylate A solution of Intermediate 130 (0.15 g) and triethylamine (0.082 ml) in dry dichloromethane (10 ml) was cooled in an ice-bath to −80° C. and treated dropwise with a 1M solution of triflic anhydride in dichloromethane (0.42 ml). After 1 h further triethylamine (0.082 ml) and triflic anhydride (0.42 m) were added and stirring at −70° C. continued. After a further 0.5 h reaction was complete. The reaction was quenched, with water (3 ml) at −70° C. and warmed to room temperature. The organic phase was separated, dried, filtered and evaporated to give an orange gum (0.226 g). This was purified by column chromatography eluting with system A (1:2) to give the title compound as a cream solid (0.153 g). m.p. 158°–159° C.
T.l.c. System A (1:1) Rf 0.40

EXAMPLE 66

1-[3-Bromo-2-[2-[[(trifluoromethyl)suphonyl]amino]phenyl]-5-benzofuranyl]methyl]-2-butyl-4-chloro-1H-imidazole-5-carboxylic acid A solution of product of Example 65 in methanol was treated with 2N NaOH and heated to reflux. Heating was continued for 2 h before cooling to room temperature. The reaction was acidified to pH~2 using 2N HCl and extracted with ethyl acetate. The combined organic extracts were dried, filtered and evaporated to give an off-white solid (0.098 g). This was crystallised from aqueous methanol to give the title compound as a cream solid (51 mg), m.p. 161°–162° C.
Assay Found: C,45.4;H,3.2;N,6.4 C$_{24}$H$_{20}$BrClF$_3$N$_3$O$_5$S requires C,45.4;H,3.2;N,6.6%

EXAMPLE 67

Ethyl 1-[[3-bromo-2-[2-(1H-tetrazol-5-yl)phenyl]-5-benzofuranyl]methyl]-2-butyl-4-propyl-1H-imidazole-5-carboxylate Hydrochloric acid (1M in methanol) was added to a solution of Intermediate 134 (0.85 g) in ethanol (3 ml). The solution was stirred at room temperature for 30 min before it was poured into saturated aqueous sodium hydrogen carbonate. The mixture was washed with ether (3×30 ml) after 15 mins and was then acidified to pH4–5 by the addition of 2N hydrochloric acid. The mixture was then extracted with ethyl acetate (3×30 ml). The combined extracts were dried, filtered and evaporated to give the title compound as a clear viscous yellow gum (0.30 g).

H.p.l.c. column Dynamax/60A $C_{18}$ Solvent A $H_2O+0.05\%$ TFA Solvent B acetonitrile $+H_2O$ (9:1)+0.05% TFA Gradient elution 10–90% B in 25 mins Retention time=21.1 minutes n.m.r. δ(250 MHz, CDCl$_3$)8.05–8.13(1H,m), 7.88–7.93 (1H,m),7.66–7.73(2H,m), 7.3(1H,d),6.89–6.95(2H,m),5.49(2H,s),4.12 (2H,q),2.38–2.48(2H,m), 1.83–1.92(2H,m),1.0–1.42(9H,m),0.75(3H,t),0.6 (3H,t).

EXAMPLE 68

1-[[3-Bromo-2-[2-(1H-tetrazol-5-yl)phenyl]-5-benzofuranyl]methyl]-2-butyl-4-propyl-1H-imidazole-5-carboxylic acid.

The product of Example 67 (220 mg) was dissolved in methanol (10 ml). 2N aqueous sodium hydroxide (10 ml) was added followed by methanol (~1 ml) to effect complete dissolution. The mixture was stirred at room temperature for 24 h, diluted with water (20 ml), washed with ether (3×20 ml) and then acidified to pH4 by the dropwise addition of 2N hydrochloric acid. The resultant precipitate was collected, washed with water on the filter pad, and dried in vacuo to give the title compound as a white amorphous solid (0.16 g).

H.p.l.c. (conditions as in Example 67) Retention time=17.82 minutes n.m.r. δ(DMSO d$_6$ 250 MHz)7.8–7.9(1H,m),7.7–7.8(1H,m),7.48–7.6 (2H,m), 7.19(1H,d),7.0(1H,br s),6.88(1H,dd),5.58(2H,s),2.76–2.87(2H,t),2.6–2.7(2H,t),1.5–1.7(4H,m),1.2–1.34(2H,m),0.72–0.9(6H, 2×t)

EXAMPLE 69

1-[[3-Bromo-2-[2-(1H-tetrazol-5-yl)phenyl]-5-benzofuranyl]methyl]-2-butyl-4-chloro-1H-imidazole-5-carboxylic acid A mixture of Intermediate 136 (6 g), sodium azide (4.5 g), and triethylamine hydrochloride (8 g) in DMF (50 ml) was stirred at 130° C. for 3 h. The mixture was cooled and diluted with water (100 ml) and the solution was washed with ethyl acetate (50 ml). The aqueous extract was acidified to pH3.5 with 4M hydrochloric acid and extracted with ethyl acetate (75 ml). The organic layer was extracted with saturated sodium bicarbonate solution (60 ml). The alkaline extract was washed with ethyl acetate (3×30 ml), and then acidified to pH3.2 with 4M hydrochloric acid and extracted with ethyl acetate (75 ml). The organic extract was washed with water (2×30 ml) and the solvent removed to give a solid residue. The solid was recrystallised from methanol/water (3:2) to give the title compound (5.13 g) as a monohydrate. m.p. 182° C.

n.m.r. δ(DMSO-d$_6$)0.82(t,J=7Hz, 3H),1.29(m,2H),1.58(m,2H),2.65(t,J=7 Hz, 2H),5.71(s,2H),7.08(dd, J=8 2Hz,2H),7.2(d, J=2Hz, 1H),7.49(d,J=8 Hz, 1H),7.70–8.00(m, complex, 4H).

Still further preferred compounds of the present invention include
1-[[3-bromo-2-[2-(1H-tetrazol-5-yl)phenyl]-5-benzofuranyl]methyl]-2-butyl-4-chloro-1H-imidazole-5-carboxylic acid, dipotassium salt;
ethyl 1-[[3-bromo-2-[2-(1H-tetrazol-5-yl)phenyl]-5-benzofuranyl]methyl]-4-chloro-2-ethyl-1H-imidazole-5-carboxylate;
1-[[3-bromo-2-[2-(1H-tetrazol-5-yl)phenyl]-5-benzofuranyl]methyl]-4-chloro-2-ethyl-N-isopropyl-1H-imidazole-5-carboxamide;
ethyl-1-[[3-bromo-2-[2-(1H-tetrazol-5-yl)phenyl]-5-benzofuranyl]methyl]-4-chloro-2-propyl-1H-imidazole-5-carboxylate;
ethyl-1-[[3-bromo-2-[2-(1H-tetrazol-5-yl)phenyl]-5-benzofuranyl]methyl]-4-methyl-2-propyl-1H-imidazole-5-carboxylate;
ethyl 1-[[3-bromo-2-[2-(1H-tetrazol-5-yl)phenyl]-5-benzofuranyl]methyl]-4methyl-1H-imidazole-5-carboxylate;
ethyl 1-[[3-bromo-2-[2-(1H-tetrazol-5-yl)phenyl]-5-benzofuranyl]methyl-5-methyl-1H-imidozole-4-carboxylate;
ethyl 1-[[3-bromo-2-[2-(1H-tetrazol-5-yl)phenyl]-5-benzofuranyl]methyl]-4-chloro-2-methyl-1H-imidazole-5-carboxylate;
ethyl 1-[[3-bromo-2-[2-(1H-tetrazol-5-yl)phenyl]-5-benzofuranyl]methyl]-2-ethyl-4-methyl-1H-imidazole-5-carboxylate hydrochloride;
1-[[3-bromo-2-[2-(1H-tetrazol-5-yl)phenyl]-5-benzofuranyl]methyl]-2-ethyl-4-methyl-N-methyl-1H-imidazole-5-carboxamide hydrochloride;
butyl 1-[[3-bromo-2-[2-(1H-tetrazol-5-yl)phenyl]-5-benzofuranyl]methyl]-4chloro-2-ethyl-1H-imidazole-5-carboxylate;
1-[[3-bromo-2-[2-(1H-tetrazol-5-yl)phenyl]-5-benzofuranyl]methyl]-4-methyl-2-propyl-1H-imidazole-5-carboxylic acid;
1-[[3-bromo-2-[2-(1H-tetrazol-5-yl)phenyl]-5-benzofuranyl]methyl]-4-methyl-1H-imidazole-5-carboxylic acid;
ethyl 1-[5-[3-bromo-2-[2-(1H-tetrazol-5-yl)phenyl]-5-benzofuranyl]methyl]-2-butyl-4-methyl-1H-imidazole-5-carboxylate;
1-[[3-bromo-2-[2-(1H-tetrazol-5-yl)phenyl]-5-benzofurany]methyl]-4chloro-2methyl-1H-imidazole-5-carboxylic acid;
1-[[3-bromo-2-[2-(1H-tetrazol-5-yl)phenyl]-5-benzofuranyl]methyl]-2-ethyl-4-methyl-1H-imidazole-5-carboxylic acid hydrochloride;
ethyl 1-[[3-bromo-2-[2-(1H-tetrazol-5-yl)phenyl]-5-benzofuranyl]methyl]-4-methyl-2-pentyl-1H-imidazole-5-carboxylate;
1-[[3-bromo-2-[2-(1H-tetrazol-5-yl)phenyl]-5-benzofuranyl]methyl]-4-methyl-2-pentyl-1H-imidazole-5-carboxylic acid;
ethyl 1-[[3-bromo-2-[2-(1H-tetrazol-5-yl)phenyl]-5-benzofuranyl]methyl]-2,4-dimethyl-1H-imidazole-5-carboxylate;
1-[[3-bromo-2-[2-(1H-tetrazol-5-yl)phenyl]-5-benzofuranyl]methyl]-2,4-dimethyl-1H-imidazole-5-carboxylic acid;
ethyl 1-[[3-bromo-2-[2-[[(trifluoromethyl)sulphonyl]amino]phenyl]-5benzofuranyl]methyl]-4-methyl-2-propyl-1H-imidazole-5-carboxylate;
1-[[3-bromo-2-[2-[[(trifluoromethyl)sulphonyl]amino]phenyl]-5benzofuranyl]methyl]-4-methyl-2-propyl-1 H-imidazole-5-carboxylic acid;
1-[[3-bromo-2-[2-[[(trifluoromethyl)sulphonyl]amino]phenyl]-5benzofuranyl]methyl]-2-butyl-4-chloro-N-methyl-1H-imidazole-5-carboxamide; and physiologically acceptable salts, solvates and metabolically labile esters thereof.

These compounds may be prepared as below

Intermediate 137

Ethyl 1-[[3-bromo-2-[2-[2-(triphenylmethyl)-2H-tetrazo-5-yl]phenyl]-5-benzofuranyl]methyl]-4-chloro-2-ethyl-1H-imidazole-5-carboxylate A solution of Intermediate 70 (0.50 g) and 1,1'-carbonyldiimidazole (0.31 g) in THF (12.5 ml) was stirred at room temperature for 16 h and then ethanol (0.38 ml) was added and the resultant solution was stirred at room temperature for 6 h after which time further ethanol (760 ml) was added and the reaction mixture stirred at room temperature for 24 h. The solvent was removed in vacuo and the residue purified by column chromatography eluting with ether:petroleum ether (1:1) to afford the title compound (283 mg) as a white foam.
T.l.c ether Rf=0.90
Similarly prepared

Intermediate 138

1-[[3-Bromo-2-[2-[2-(triphenylmethyl)-2H-tetrazol-5-yl]phenyl]-5-benzofuranyl]methyl]-4-chloro-2-ethyl-N-isopropyl-1H-imidazole-5-carboxamide as a pale pink solid (316 mg).
T.l.c. ether Rf=0.77.

From a solution of Intermediate 70 (0.5 g) and 1,1'-carbonyldiimidazole (0.31 g) in THF (12.5 g) with the addition of isopropylamine (0.551 g).

Intermediate 139

Ethyl 1-[[3-bromo-2-[2-[2-(triphenylmethyl)-2H-tetrazol-5-yl]phenyl]-5-benzofuranyl]methyl]4-chloro-2-prol-1H-imidazole-5-carboxylate as a white solid (810 mg).
T.l.c ether:petroleum ether (1:1) Rf=0.71

From a solution of Intermediate 36 (1.0 g) and 1,1'-carbonyldiimidazole (610 mg) in THF (25 ml) with the addition of ethanol (720 μl).

Intermediate 140

Butyl 1-[[3-bromo-2-[2-[2-(triphenylmethyl)-2H-tetrazol-5-yl]phenyl]-5-benzofuranyl]methyl]4-chloro-2-ethyl-1H-imidaole-5-carboxylate as a white foam (349 mg)
T.l.c. ether Rf=0.93

From a solution of Intermediate 70 (0.50 g) and 1,1'-carbonyldiimidazole (0.31 g) in THF (12.5 g) with the addition of two portions of n-butanol (0.592 ml and 1.00 ml)

Intermediate 141

Ethyl 4-methyl-2-propyl-1H-imidazole-5-carboxylate

Ethyl 2-amino-3-oxobutanoate hydrochloride (10 g) was added to a stirring solution of ethyl butaneimidate (83.5 g) in ethanol (800 ml, freshly distilled from magnesium ethoxide) and triethylamine (85 ml) and the resultant yellow mixture stirred at room temperature for 48 h. The solvent was removed in vacuo and the residue diluted with water (500 ml) and extracted into ethyl acetate (3×200 ml). The combined organic extracts were washed with water (2×100 ml), dried and concentrated in vacuo. The resultant residue was purified by trituration with ether (5×50 ml) and the residual buff solid dried to afford the title compound (4.05 g)
T.l.c. ether Rf=0.31

Intermediate 142

Ethyl 1-[[3-bromo-2-[2-[2-(triphenylmethyl)-2H-tetrazol-5-yl]phenyl]-5-benzofuranyl]methyl]44methyl-2-propyl-1H-imidazole-5-carboxylate A mixture of Intermediate 141 (1.5 g), Intermediate 15 (6.4 g) and potassium carbonate (1.45 g) were heated at 70° C. for 6.5 h in DMF (150 ml). The reaction mixture was allowed to cool to room temperature overnight and then partitioned between water (500 ml), ammonium chloride solution (saturated aqueous, 500 ml) and ethyl acetate (500 ml). The separated organic extracts were washed with water (2×200 ml), brine (100 ml), dried and concentrated in vacuo, to afford the crude product. This was purified by column chromatography eluting with dichloromethane:hexane:acetic acid (50:50:1) and then methanol to afford an enriched product. This product was further purified by chromatography eluting with dichloromethane:ether:ethanol:acetic acid. (95:5:2:1) to afford a more enriched sample of the product and final purification by chromatography eluting with ether:petroleum ether (3:1) gave the title compound as a white solid (350 mg).
Tlc ether:petroleum ether (3:1) Rf=0.31
Similarly prepared

Intermediates 143 and 144

Ethyl 1-[[3-bromo-2-[2-[2-(triphenylmethyl)-2H-tetrazol-5-yl]phenyl]-5-benzofuranyl]methyl]-4-methyl-1H-imidazole-5-carboxylate (375 mg)
T.l.c. petroleum ether:ether (1:1)+4% methanol+2% acetic acid Rf=0.30
Ethyl 1-[[3-bromo-2-]2-]2(triphenylmethyl)-2H-tetrazol-5-yl]phenyl]-5-benzofuranyl]methyl]-5-methyl-2H-imidazole-4-carboxylate (100 mg)
T.l.c. petroleum ether:ether (1:1)+4% methanol+2% acetic acid Rf=0.20

From a solution of Intermediate 15 (1.47 g), ethyl 4-methyl-1H-imidazole-5-carboxylate (320 mg) and potassium carbonate (350 mg) in dry DMF (40 ml). Purification by column chromatography eluting with petroleum ether:ether (1:1)+4% methanol+2% acetic acid afforded the title compounds.

Intermediate 145

2-Ethyl-4-methyl-1H-imidazole-5-methanol

Concentrated HCl (75 ml) was added to a solution of 2-ethyl-4-methyl-1H-imidazole (21 g) and aqueous formaldehyde (37% 14 ml) in water (100 ml) and the mixture heated under reflux for 48 h. The cooled mixture was basified to pH10 with sodium hydroxide (5N) and extracted with chloroform/isopropanol (4:1) (3×100 ml). The combined organic extracts were washed with brine (1×200 ml) and dried. The solution was filtered and evaporated to give a pale yellow gum (18 g) which was purified by column chromatography eluting with chloroform/methanol/ammonia (90:10:1) the title compound as a pale yellow foam (12.6 g)
T.l.c chloroform/methanol/ammonia (90:10:2) Rf 0.3

Intermediate 146

2-Ethyl-4-methyl-1H-imidazole-5-carboxaldehyde

Activated manganese dioxide (20 g) was added to a suspension of Intermediate 145 (7.0 g) in dichloromethane/dioxan (2:1) (200 ml) and the mixture treated according to the method of Intermediate 16. Purification by column chromatography eluting with ether gave the title compound as a colourless crystalline solid (4.0 g)

Tl.c. ether Rf 0.2

Intermediate 147

1-[[3-Bromo-2-[2-[2-(triphenylmethyl)-2H-tetrazol-5-yl]phenyl]-5-benzofuranyl]methyl]-2-ethyl-4-methyl-1H-imidazole-5-carboxaldehyde A mixture of Intermediate 146 (2.0 g), Intermediate 15 (11.24 g) and potassium carbonate (2.4 g) in dry DMF (100 ml) was heated at 80° C. for 5 h. The cooled mixture was partitioned between water (300 ml) and ethyl acetate (3×300 ml). The combined organic extracts were washed with brine/water (1:1) (3×300 ml) and dried. The solvent was evaporated to give a pale yellow gum which was purified by column chromatography eluting with ether to give the title compound as a colourless foam (4.15 g)

T.l.c ether Rf 0.25

Intermediate 148

1-[[3-Bromo-2-[2-[2-(triphenylmethyl)-2H-terrazol-5yl]phenyl]-5-benzofuranyl]methyl]-2-ethyl-4-methyl-1H-imidazole-5-carboxylic acid A solution of sodium chlorite (80%; 4.86 g) and sodium dihydrogen phosphate (4.86 g) in water (20 ml) was added to a mixture of Intermediate 147 (3.94 g), 2-methyl-2-butene (2M;26 ml) and tert-butanol (40 ml) in THF (40 ml). The mixture was stirred vigorously for 24 h and then the organic solvent was evaporated. The residue was filtered to give the title compound as a colourless solid (3.3 g)

T.l.c. (ethyl acetate) Rf 0.2;

Intermediate 149

2-Methyl-1H-imidazole-5-methanol

Ammonia was condensed into a 3-necked 1-liter flask, to give ca 250 ml of liquid. Dihydroxy acetone (966.7 g) was added portionwise followed by methyl ethaneimidate hydrochloride (66.7 g). The suspension was transferred to an autoclave, cooled in an acetone/dry ice bath under nitrogen, which was then sealed and heated at 90° C. with stirring. After 18 h the autoclave was cooled to room temperature and then further cooled to −50° C. The top of the autoclave was removed and the contents were poured into cold (−50° C.) methanol 300 ml. The dark solution was allowed to warm to room temperature then evaporated to give a red oil (140.2 g). A precipitate formed on standing, this was filtered and washed with dichloromethane (2×300 ml), and the filtrate concentrated in vacuo to yield a brown oil (58.7 g). Purification by chromatography eluting with System C (50:8:1) gave the title compound as a yellow solid (32.5 g).

T.l.c. System C (25:8:1) Rf 0.46.

Intermediate 150

4-Chloro-2-methyl-1H-imidazole-5-methanol

N-Chlorosuccinimide (28.04 g) was added to a solution of Intermediate 149 (18.27 g) in dry dioxan (230mi) and dry 2-methoxyethanol (230 ml) at 20° C. and treated according to the method of Intermediate 67. Purification by chromatography eluting with System C (100:8:1) gave the title compound as a yellow solid (4.9 g).

T.l.c. System C (100:8:1) Rf 0.23.

Intermediate 151

4-Chloro-2-ethyl-1H-imidazole-5-carboxaldehyde

Manganese dioxide (1.89 g) was added to a solution of Intermediate 150 (579 mg) in dichloromethane: dioxan (1:2)(30 ml). The suspension was heated at reflux for 5 h, cooled and filtered. The filtrate was concentrated in vacuo to yield a yellow solid (538 mg) which was purified by chromatography eluting with System C (150:8:1) to give the title compound as a pale yellow solid (449 mg).

T.l.c System C (100:8:1) Rf0.38

Intermediate 152

1-[[3-Bromo-2-[2-[2-(triphenylmethyl)-2H-tetrazol- 5-yl]phenyl]-5-benzofuranyl]methyl]-4-chloro-2-methyl-1H-imidazole-5-carboxaldehyde A mixture of Intermediate 151 (2.09 g), Intermediate 15 (14.17 g) and potassium carbonate (2.90 g), in dry DMF (1 50 ml) was heated at reflux for 4 h. The reaction mixture was cooled and poured into water (600 ml). The aqueous phase was extracted with ethyl acetate (3×60 ml) and the combined extracts were dried and concentrated in vacuo to yield a brown oil (25.40 g). Purification by chromatography eluting with ether:petroleum ether (5: 1) gave the title compound as a pale yellow solid (9.8 g).

T.l.c. ether:petroleum ether (5:1) Rf 0.48.

Intermediate 153

1-[[3-Bromo-2-[2-[2-(triphenylmethyl)-2H-tetrazol-5-yl]phenyl]-5-benzofuranyl]methyl]-4-chloro-2-methyl-1H-imidazole-5-carboxylic acid A solution of potassium permanganate (1.14 g) in water (60 ml) was added over 5 mins. to a stirred solution of Intermediate 152 (4.00 g) in acetone (100 ml) at 70° C. The suspension was stirred at 70° C. for 1.5 h, further potassium permanganate (550 mg) in water (30 ml) was added and stirring at 70° C. was continued for 3 h. Sodium metabisulphite solution (5%,100 ml) was added and the mixture was extracted with ethyl acetate (3×40 ml). The combined extracts were dried and concentrated in vacuo to yield a pale yellow foam (2.237 g). Purification by chromatography eluting with dichloromethane: methanol (10:1) gave the title compound as a white powder (500 mg).

T.l.c dichloromethane:methanol (10:1) Rf 0.50

Intermediate 154

Ethyl 1-[[3-bromo-2-[2-[2-(tripthenylmethyl)-2H-tetrazol-5-yl]phenyl]-5-benzofuranyl]-4-chloro-2-methyl-1H-imidazole-5-carboxylate 1,1'-Carbonyldiimidazole (272 mg) was added to a stirred solution of Intermediate 153 (490 mg) in dry THF (5 ml) at 20° C. The solution was stirred for 8 h then sodium ethoxide (265 mg) was added and stirring continued for 12 h. Water (20 ml) was added and the mixture extracted with ethyl acetate (3×30 ml). The combined extracts were dried and concentrated in vacuo to yield a yellow gum (777 mg). Purification by chromatography eluting with ether:petroleum ether (5:1) gave the title compound as a white powder (117 mg)

T.l.c. ether:petroleum ether (5:1) Rf=0.47.

Intermediate 155

Ethyl 1-[[3-bromo-2-[2-[2-(triphenylmethyl)-2H-tetrazol-5-yl]phenyl]benzofuranyl]methyl-2-ethyl-4-methyl-1H-imidazole-5-carboxylate 1,1'-Carbonyldiimidazole (0.324 g) was added to a solution of Intermediate 148 (0.5 g) in dry THF (15 ml) at room temperature under nitrogen. The mixture was stirred for 1 h, then sodium ethoxide (30 mg) was added and the mixture stirred for 48 h. The solvent was evaporated and the residue purified by column chromatography eluting with ethyl acetate to give the title compound as a colourless foam (242 mg).

T.l.c ethyl acetate Rf 0.75

Intermediate 156

1 -[[3-Bromo-2-[2-[2-(triphenylmethyl)-2H-tetrazol-5-yl]phenyl]-5-benzofuranyl]methyl]2-ethyl-4-methyl-N-methyl-1H-imidazole-5-carboxamide 1,1'-Carbonyldiimidazole (324 mg) was added to a solution of Intermediate 148 (0.5 g) in dry THF (15 ml) at room temperature under nitrogen. The mixture was stirred for 1 h, then aqueous methylamine (40%;0.3 ml) was added and the mixture stirred for 16 h. The solvent was evaporated and the residue purified by column chromatography eluting with ethyl acetate to give the title compound as a colourless foam (0.3 g)

T.l.c. ethyl acetate/methanol (5:1) Rf 0.85

Intermediate 157

Ethyl hexaneimidate hydrochloride

Hydrogen chloride was bubbled through a stirred solution of hexanenitrile (50 g) in ethanol (35.9 ml) cooled at $-10°$ C. for 3 h. The solution was allowed to stand at $-5°$ C. for 7 days, then was concentrated in vacuo. The resulting oil was poured into ether (800 ml) and the solution cooled to $-40°$ C. and stirred for 10 min. The resulting solid was filtered off under nitrogen and dried in vacuo to obtain the title compound, (81 g) as a white solid.

Intermediate 158

Ethyl 5-methyl-2-pentyl-1H-imidazole4-carboxylate

Ethyl 2-amino-3-ketobutanoate hydrochloride (3.0 g) was added portionwise to a solution of Intermediate 157 (30 g) and triethylamine (26 ml) in ethanol (500 ml) under nitrogen. The resulting solution was left to stand at 22° for 72 h. The solvent was removed in vacuo, then the residue was dissolved in ethyl acetate (200 ml) and washed with water (200 ml). The aqueous layer was further extracted with ethyl acetate (200 ml). The combined organic extracts were dried, concentrated in vacuo and the residue purified by chromatography eluting with System A (8:2) to obtain the title Compound (3.05 g) as a pale yellow solid, m.p. 89°–90° C.

Intermediate 159

Ethyl 1-[[3-bromo-2-[2-[2-(triphenylmethyl)-2H-tetrazol-5-yl]phenyl]-5-benzofuranyl]methyl]-4-methyl-2-pentyl-1H-imidazole-5-carboxylate A mixture of Intermediate 15 (3.1 g), Intermediate 158 (0.5 g) and potassium carbonate (0.367 g) in DMF (50 ml) was stirred at 22° for 16 h. The reaction mixture was diluted with ether (50 ml) and washed with water (50 ml). The phases were separated and the aqueous layer was extracted with ethyl acetate (50 ml). The combined extracts were dried and concentrated in vacuo to give a yellow oil which was purified by chromatography eluting with system A (6:4) to afford the title compound (0.8 g) as a white solid, m.p. 89°–90° C.

Intermediate 160

Ethyl 2,4-dimethyl-1H-imidazole-5-carboxylate

Ethyl 2-amino-3-oxobutanoate hydrochloride (5 g) was added portionwise to a solution of ethyl ethaneimidate (34.0 g) and triethylamine (42 ml) in ethanol (500 ml), and the resulting yellow solution was stirred overnight. Solvent was removed in vacuo and the residue partitioned between water (200 ml) and ether (200 ml). The organic layer was separated and the aqueous phase further extracted with ether (2×200 ml). The dried organic extracts were evaporated in vacuo and the residue washed with cold ether and filtered to give the title compound as a white solid (1.1 g). m.p. 165–166° C.

Intermediate 161

Ethyl [[3-bromo-2-[2-[2-(triphenylmethyl)-2H-tetrazol-5-yl]phenyl]-5-benzofuranyl]methyl]-2,4-dimethyl-1H-imidazole-5-carboxylate Intermediate 15 (7.6 g) was added to a solution of Intermediate 160 (0.9 g) and potassium carbonate (0.9 g) in DMF (100 ml) and the resulting mixture stirred for 3 days. The mixture was poured into water (300 ml) then extracted with ethyl acetate (5×150mi). The organic extracts were washed with water (150 ml), brine (150 ml), 2% lithium chloride in water (100 ml) then dried. Solvent was removed in vacuo, and the residue purified by chromatography eluting with ether:ethanol (3%) to give the title compound as a white solid (2.1 g) m.p. 98°–100° C.

Intermediate 162

1,1-Dimethylethyl [2-[3-bromo-5-(bromomethyl)-2-benzofuranyl]phenyl]carbamate

A solution of Intermediate 128 (4.29 g) and benzoyl peroxide (30 mg) in dry carbon tetrachloride (100 ml) was heated at reflux whilst being irradiated with a 200 W lamp for 1.5 hours. The mixture was filtered, and the filtrate was washed with water (2×100 ml). The organic solution was dried, filtered and evaporated to give the title compound (5 g).

Intermediate 163

Ethyl 1-[[3-bromo-2-[2-[[(1,1-dimethylethoxy)carbonyl]amino]phenyl]-5-benzofuranyl]methyl]-4-methyl-2propyl-1H-imidazole-5-carboxylate A solution of Intermediate 141 (0.51 g) and sodium hydride (0. 11 g; 60% dispersion in oil) in dry DMF (6 ml) was stirred at ambient temperature for 2 hours. The mixture was cooled to 0° to 5° and Intermediate 162 (1.25 g) was added. The reaction mixture was stirred at 0° rising to ambient temperature for 20 hours. The solvent was evaporated in vacuo and the residue was dissolved in ether (100 ml). The ethereal solution was washed with water (100 ml) aqueous sodium bicarbonate solution (8%;100 ml), aqueous lithium chloride solution (10%;50 ml), dried and evaporated. The residue was purified by column chromatography to give the title compound as an off-white foam (0.2 g).

T.l.c. System B (2:25) Rf=0.65

Intermediate 164

Ethyl 1-[[2-(2-aminophenyl)-3-bromo-5-benzofuranyl]-methyl]-4-methyl-2propyl-1H-imidazole-5-carboxylate A solution of Intermediate 163 (0.19 g) in a mixture of dichloromethane (3 ml) and trifluoroacetic acid (1 ml)

was stirred at 0° to ambient temperature for 4 hours. The solvent was removed in vacuo and ethanol (5 ml) and ammonia (1 ml) were added and the solution was re-evaporated. The residue was purified by column chromatography eluting with dichloromethane/methanol (20:1) to give the title. Compound (0.136 g) as a yellow foam, m.p. 135°-6° C.

EXAMPLE 70

1-[[3-Bromo-2-[2-(1H-tetrazol-5-yl)phenyl]-5-benzofuranyl methyl]-2-butyl-4-chloro-1H-imidazole-5-carboxylic acid, dipotassium salt Ethanolic potassium hydroxide (1.0M), was added to a stirred solution of the product of Example 3 (1.23 g), in ethanol (34 ml). The solution was concentrated to 5 ml then dry ether (40 ml) was slowly added and precipitation occurred. The precipitate was allowed to settle, and the supernatant solution decanted. The precipitate was stirred with dry ether and decanted (2×10 ml). The solid was dissolved in ethanol (8 ml), then precipitated with ether (2×20 ml) and dried to give a white solid (1.445 g). mp. 58°-62° C. (Softens).

Analysis Found C,40.8;H,2.3;N,11.9;K,10.9 $C_{24}H_{18}Br_2ClK_2N_6O_3$ requires C,40.5;H,2.55;N,11.8;K,11.0%

EXAMPLE 71

Ethyl 1-[[3-bromo-2-[2(1H-tetrazol-5-yl)phenyl]-5-benzofuranyl]methyl]-4-chloro-2-ethyl-1H-imidazole-5-carboxylate A solution of Intermediate 137 (283 mg) in ethanol (10 ml) and concentrated HCl (0.2 ml) was stirred at room temperature for 2.5 h and then the pH was adjusted to pH9 (2N aqueous sodium bicarbonate). The solvent was removed in vacuo and the residue dissolved in water (80 ml) and extracted into ether (3×30 ml). The aqueous phase was acidified to pH5 (2N HCl) and then extracted into ethyl acetate (3×30 ml). The combined ethyl acetate extracts were dried and concentrated in vacuo to afford the title compound as a white glassy solid (141 mg). m.p. 106°-108° C.

T.l.c. ether Rf=0.12

Similarly prepared

EXAMPLE 72

1-[[3-Bromo-2-[2-(1H-tetrazol-5-yl)phenyl]-5-benzofuranyl]methyl]-4-chloro-2-ethyl-N-isopropyl-1H-imidazole-5-carboxamide as a white solid (184 mg) m.p. 108°-110° C.

T.l.c ether Rf=0.16

From a solution of Intermediate 138 (310 mg) in ethanol (10 ml) and concentrated HCl (0.2 ml).

EXAMPLE 73

Ethyl 1-[[3-bromo-2-[2-(1H-tetrazol-5-yl)phenyl]-5-benzofuranyl]methyl]-4-chloro-2-propyl-1H-imidazole-5-carboxylate as a buff solid (180 mg)

Tlc ether:petroleum ether Rf=0.09 n.m.r δ(250 MHz,CDCl₃),0.79(3H,t),1.22(3H,t),1.45(2H,sex), 2.22(2H,t),4.2(2H,q),5.58(2H,s),7.0(2H,d+s),7.27(1H,-m), 7.65(2H,m),7.89(1H,m),8.0(1H,m).

From a solution of Intermediate 139 (460 mg) in THF (20 ml), ethanol (30 ml) and concentrated HCl (0.3 ml).

EXAMPLE 74

Ethyl 1-[[3-bromo-2-[2-(1H-tetrazol-5-yl)phenyl]-5-benzofuranyl]methyl]-4-2-propyl-1H-imidazole-5-carboxylate as a white solid (181 mg).

Tlc ether:petroleum ether Rf=0.05 n.m.r δ(250 MH₂, CDCl₃),0.6(3H,t),1.2(2H,t),1.31(2H,sex), 2.0(5H,s+t)4.1(2H,q),5.5(2H,s),6.91(1H,s),7.0(1H,dd), 728(1H,m),7.68(2H,m),7.90(1H,m),8.1(1H,m).

From a solution of Intermediate 142 (350 mg) in ethanol (10 ml) and concentrated HCl (0.2 ml).

EXAMPLE 75

Ethyl 1-[[3-bromo-2-[2-(1H-tetrazol-5-yl)phenyl]-5-benzofuranyl]methyl]-4-methyl-1H-imidazole-5-carboxylate (100 mg), m.p. 192° C.

T.l.c. ether:petroleum ether:ethanol:acetic acid (80:20:2:2) Rf=0.16

From a solution of Intermediate 143 (200 mg) in ethanol (10 ml) and concentrated HCl (0.2 ml).

EXAMPLE 76

Ethyl 1-[[3-bromo-2-[2-(1H-tetrazol-5-yl)phenyl]-5-benzofuranyl]methyl]-5-methyl]-1H-imidozole-4-carboxylate (30 mg) m.p 183°-185° C.

T.l.c. ether:petroleum ether:ethanol:acetic acid (80:20:2:2) Rf=0.09

From a solution of Intermediate 144 (50 mg) in ethanol (5 ml) and concentrated HCl (0.1 ml).

EXAMPLE 77

Ethyl 1-[[3-bromo-2-[2-(1H-tetrazol-5-yl)phenyl]-5-benzofuranyl]methyl]-4-chloro-2-methyl-1H-imidazole-5-carboxylate (74 mg) m.p. 205°-208° C.

T.l.c. dichloromethane:methanol (10:1) Rf=0.42

From a solution of Intermediate 154 (110 mg) in ethanol (2 ml), THF (0.5 ml) and concentrated HCl (0.1 ml).

EXAMPLE 78

Ethyl 1-[[3-bromo-2-[2-(1H-tetrazol-5-yl)phenyl]-5-benzofuranyl]methyl]-2-ethyl-4-methyl-1H-imidazole-5-carboxylate hydrochloride (101 mg) m.p. 160°-165° C.

T.l.c dichloromethane/ethanol (10:1) Rf 0.45.

From a solution of Intermediate 155 (230 mg) in ethanol (15 ml) and concentrated HCl (0.1 ml).

EXAMPLE 79

1.-[[3-Bromo-2-[2-(1H-tetrazol-5-yl)phenyl]-5-benzofuranyl]methyl]-2-ethyl-4-methyl-N-methyl-1H-imidazole-5-carboxamide hydrochloride as a colourless solid (84 mg) m.p. 190°-195° C.

T.l.c ethyl acetate/methanol (5:1) Rf 0.2

From a solution of Intermediate 156 (0.3 g) in methanol (15 ml) and concentrated HCl (0.2 ml).

EXAMPLE 80

Butyl 1-[[3-bromo-2-(1H-tetrazol-5-yl)phenyl]-5-benzofuranyl]methyl]-4-chloro-2-ethyl- 1H-imidazole-5-carboxylate as a white solid (62 mg) m.p. 197°-199° C.

From a solution of Intermediate 140 (349 mg) in n-butanol (10 ml) and concentrated HCl (0.25 ml). Further purification was effected by dissolving the product in sodium bicarbonate solution (1% aqueous, 80 ml) and extraction into ether (3×30 ml).

EXAMPLE 81

1-[[3-Bromo-2-[2-(1H-tetrazol-5-yl)phenyl]-5-benzofuranyl]methyl]-4-methyl-2-propyl-1H-imidazole-5-carboxylic acid A solution of the product of Example 74 (140 mg) and potassium hydroxide (71 mg) in ethanol (1.92 ml) and water (0.48 ml) was stirred at room temperature for 6 h and then further potassium hydroxide (120 mg) was added and the resultant solution stirred at room temperature for 16 h. The reaction mixture was acidified to pH5 and extracted into ethyl acetate (3×10 ml). The combined ethyl acetate phases were dried and concentrated in vacuo. The residue was recrystallised from 10% methanol/ethyl acetate to afford the title compound (11 mg) as a white solid.

Tlc dichloromethane:ether:ethanol:acetic acid (95:5:5:1) Rf: 0.29. n.m.r δ(250 MHz, MeOD),0.9(3H,t,)1.20(2H,sex), 2.5(3H,s),5.92(3H,s),7.1–7.4(5H,m),7.68(1H,m),7.88(1H,m)

EXAMPLE 82

1-[[3-Bromo-2-[2-(1H-tetrazol-5-yl)phenyl]-5-benzofuranyl]methyl]-5-methyl-1H-imidazole-4-carboxylic acid A solution of the product of Example 76 (60 mg), potassium hydroxide (15.1 mg), ethanol (0.54 ml) and water (0.12 ml) was stirred at room temperature for 16 hours. The solvent was removed in vacuo and the residue diluted with water (15 ml). After acidification to pH4 (2N aqueous HCl) the aqueous layer was extracted into ethyl acetate (3×15 ml). The combined organic fractions were dried and the solvent was removed in vacuo to afford the title compound (40 mg). m.p. 248° C.

T.l.c. dichloromethane:ether:ethanol:acetic acid (95:5:2:1) Rf=0.58

EXAMPLE 83

Ethyl 1 -[[3-bromo-2-[2-(1H-tetrazol-5- yl)phenyl]-5-benzofuranyl]-2butyl-4-methyl-1H-imidazole-5-carboxylate A solution of Intermediate 86 (200 mg) in methanol (4 ml) and concentrated hydrochloric acid (2 ml) was stirred at room temperature overnight. Sodium bicarbonate (10 ml) was added cautiously until basic. The mixture was extracted with ethyl acetate (3×15 ml) and the combined extracts were dried and evaporated in vacuo. The residue was purified by chromatography eluting with ether, then ether: 10% acetic acid to give the title compound as a white foam (130 mg) m.p. 101°–105° C.

T.l.c. ether:acetic acid (10:1) Rf 0.4

EXAMPLE 84

1-[[3-Bromo-2-[2-(1H-tetrazol-5-yl)phenyl]5-benzofuranyl]methyl]-4-chloro-2-methyl-1H-imidazole-5-carboxylic acid A solution of potassium permanganate (57 mg) in water (3 ml) was added to a stirred solution of Intermediate 152 (200 mg), in acetone (5 ml) at 70° C. The solution was stirred at 70° C. for 1 h, further potassium permanganate (57 mg in 3 ml water) was added and stirring at 70° C. continued for 2 h. Sodium metabisulphite solution (5%, 15 ml) was added and the aqueous phase extracted with ethyl acetate (3×30 ml). The combined extracts were dried and concentrated in vacuo to yield a white foam (200 mg). Purification by chromatography eluting with dichloromethane:methanol (10:1) gave the title compound as a white powder (84 mg). m.p. 263° C.

T.l.c. dichloromethane:methanol (10:1) Rf 0.16.

EXAMPLE 85

1-[[3-Bromo-2-[2-(1H-tetrazol-5-yl)phenyl]-5-benzofuranyl]methyl]-2-ethyl-4-methyl-1H-imidazole-5-carboxylic acid hydrochloride Concentrated HCl (0.2 ml) was added to a suspension of Intermediate 148 (1 g) in methanol (30 ml) at room temperature under nitrogen. The mixture was stirred for 4 h, then basified to pH12 with 2N sodium hydroxide. The methanol was evaporated off and the residue partitioned between water (75 ml) and ether (3×50 ml). The aqueous phase was acidified to pH1 with 2N HCl resulting in the precipitation of a colourless solid which was filtered off, washed with water (2×10 ml), then ether (2×10 ml) to give the title compound as a colourless solid (0.4 g) m.p. 180°–185°

I.r (Nujol) 3650–2200, 1717, 1250, 761cm−.

EXAMPLE 86

Ethyl 1-[[3-bromo-2-[2-(1H-tetrazol-5-yl)phenyl]-5-benzofuranyl]methyl]-4-methyl-2-pentyl-1H-imidazole-5-carboxylate A solution of Intermediate 159 (0.3 g) in methanol (6 ml) and conc. hydrochloric acid (3 ml) was stirred at 22° for 16 h. The suspension was basified with 2N sodium hydroxide solution until pH=8 and then extracted with ethyl acetate (2×30 ml). The combined extracts were dried and concentrated in vacuo to give a yellow oil which was purified by chromatography eluting with ether-acetic acid (95:5) to obtain the title compound (0.12 g) as a pale yellow foam, m.p. 103°–104° C.

T.l.c. ether-acetic acid (9:1) Rf=0.68

EXAMPLE 87

1 -[[3-Bromo-2-[2-(1H-tetrazol-5-yl)phenyl]-5-benzofuranyl]methyl]-4-methyl-2-pentyl-1H-imidazole-5-carboxylic acid A solution of the product of Example 86 (0.2 g) and aqueous sodium hydroxide solution (2M; 2 ml) in ethanol (10 ml) was stirred at reflux for 1 h. The solution was concentrated in vacuo, then diluted with water (10 ml) and extracted with ethyl acetate (10 ml). The phases were separated and the aqueous layer was acidified with 2N HCl to pH=1. The solid formed was filtered off, washed with water (10 ml) and dried in vacuo to obtain the title compound (0.18 g) as a white solid, m.p. 189°–190° (dec.).

T.l.c. ether-acetic acid (9:1) Rf=0.34

EXAMPLE 88

Ethyl 1-[[3-bromo-2-[2-(1H-tetrazol-5-yl)phenyl]-5-benzofuranyl]methyl]-2,4-dimethyl-1H-imidazole-5-carboxylate A solution of Intermediate 161 (500 mg) in methanol (10 ml) and concentrated hydrochloric acid (5 ml) was stirred at room temperature overnight. The solid which crystallised from the reaction was filtered and sodium bicarbonate solution (8%,25ml) was added cautiously to the filtrate. The mixture was extracted with dichloromethane (3×25 ml) and the combined organic extracts were dried and evaporated in vacuo. The residue was purified by chromatography eluting with ether:ethanol (10:1) then ether:ethanol:acetic acid (10: 1:1) to give the product as a dark solid (200 mg). The solid was washed with chloroform and insoluble material filtered. The filtrate was evaporated in vacuo to give the title compound as a pale green solid (130 mg) m.p. 116°–120°.

T.l.c. ethanol:ether:acetic acid (1:10:1) Rf 0.5

EXAMPLE 89

1-[[3-Bromo-2-[2-(1H-tetrazol-5-yl)phenyl]5-benzofuranyl]methyl]-2,4-dimethyl-1H-imidazole-5-carboxylic acid A solution of Intermediate 161 (200 mg) in methanol (4 ml) and concentrated hydrochloric acid (2 ml) was stirred at room temperature overnight. Water (2 ml) was added and then the solution was basified with 2N NaOH. The basic mixture was extracted with ethyl acetate (2×10 ml) and evaporated in vacuo, and the residue heated at reflux in a solution of ethanol (6 ml) and 2N sodium hydroxide (4 ml) for 3 hours. The mixture was diluted with water, concentrated in vacuo then acidified with 2N hydrochloric acid. Insoluble solid which formed was filtered then washed with ether to give the title compound as an off-white solid (60 mg) mp 185°–190° C. (dec).

hplc (conditions as in Example 53) Retention time 14.80 mins.

EXAMPLE 90

Ethyl 1-[[3-bromo-2-[2-[[(trifluoromethyl)sulphonyl]amino]phenyl]-5-benzofuranyl]methyl]-4-methyl-2-propyl-1H-imidazole-5-carboxylate A solution of Intermediate 164 (0.133 g) and dry triethylamine (33 mg) in dry dichloromethane (5 ml) at −85° was treated with a solution of trifluoromethane sulphonyl anhydride in dry dichloromethane (0.33 ml; 1M). The mixture was stirred at −85° to −75° for 3 h and water (5 ml) was added. The product was extracted with dichloromethane (20 ml). The organic extract was washed with hydrochloric acid (2M; 20 ml), dried, filtered and evaporated in vacuo. The residue was purified by column chromatography eluting with dichloromethane/methanol (50:1) to give the title compound as a white solid (0.135 g), m.p. 123°–5°.

T.l.c dichloromethane:methanol (35:1) Rf=0.45

EXAMPLE 91

1-[[3-Bromo-2-[2-[[(trifluoromethyl)sulphonyl]amino]phenyl]-5-benzofuranyl]methyl]-4-methyl-2-propyl-1H-imidazole-5-carboxylic acid A solution of the product of Example 90 (0.13 g) in a mixture of methanol (6 ml) and aqueous sodium hydroxide solution (2M; 2 ml) was heated at reflux for 3 h. Hydrochloric acid (2M; 2 ml) was added to the cooled mixture and the resulting precipitate was collected by filtration. The solid was crystallized from methanol and water to give the title compound as a white solid, (0.06 g) m.p. 168°–170°.

Assay Found: C,47.3; H,3.5; N,6.6; $C_{24}H_{21}BrF_3N_3O_5S.0.5H_2O$ requires C,47.3; H,3.6; N,6.9%

EXAMPLE 92

1-[[3-Bromo-2-[2-[[(trifluoromethyl)sulphonyl]amino]phenyl]-5-benzofuranyl]methyl]-2-butyl-4-chloro-N-methyl-1H-imidazole-5-carboxamide A solution of the product of Example 65 (0.17 g) in methylamine (10 ml) was heated at 50° for 18 hours. The solvent was allowed to evaporate. The residue was dissolved in dichloromethane (50 ml) and washed with hydrochloric acid (2M:50 ml). The organic solution was purified by column chromatography eluting with dichloromethane/methanol (20:1) to give the title compound as a white foam (0.136 g) m.p. 89°–92° C.

Analysis Found: C,46.1; H,3.6; N,8.35; $C_{25}H_{23}BrClF_3N_4O_4S$ requires C,46.35; H,3.6; N,8.65%

The present invention is further illustrated by the following examples

Intermediate 165

1-[[3-Bromo-2-[2-[[(1,1-dimethylethoxy)carbonyl]amino]phenyl]-5-benzofuranyl]methyl]-4-chloro-2-ethyl-1H-imidazole-5-carboxaldehyde A mixture of Intermediate 162 (9.5 g), Intermediate 151 (2.95 g) and potassium carbonate (3.1 g) in DMF (30 ml) was stirred at room temperature under a nitrogen atmosphere for 18 h. The suspension was diluted with water (50 ml) and extracted with diethyl ether (3×150 ml). The combined extracts were dried and concentrated in vacuo to an oil which was purified by flash chromatography eluting with System A (3:7) to give the title compound (4.55 g) as a white solid, m.p. 65°–66°.

Similarly prepared were

Intermediate 166

1-[[3-Bromo-2-[2-[[(1,1-dimethylethoxy)carbonyl]amino]phenyl]-5-benzofuranyl]methyl]-4-chloro-2-propyl-1H-imidazole-5-carboxaldehyde
m.p. 75°–76° C.

From Intermediate 162 and 4-chloro-2-propyl-1H-imidazole-5-carboxaldehyde

Intermediate 167

1-[[3-Bromo-2-[2-[[(1,1-dimethylethoxy)carbonyl]amino]phenyl]-5-benzofuranyl]methyl]-2-ethyl-4-methyl-1H-imidazole-5-carboxaldehyde
n.m.r. (250 MHz, CDCl$_3$) $\delta$1.34(3H,t),1.48(9H,s),2.73(2H,q),5.69 (2H,s),7.07–7.2(3H,m),7.07–7.2(2H,m),7.63(1H,dd),8.18(1H, brd),9.8(1H,s)

From Intermediate 162 and Intermediate 146.

Intermediate 168

Ethyl 1-[[3-Bromo-2-[2-[[(1,1-dimethylethoxy)carbonyl]amino]phenyl-5-benzofuranyl]methyl2,4-dimethyl-1H-imidazole-5-carboxaldehyde
m.p. 144°–145° C.

From Intermediate 162 and Intermediate 160.

Intermediate 169

1-[[3-bromo-2-[2-[[(1,1-dimethylethoxy)carbonyl]amino]phenyl]-5-benzofurany]methyl]-4-chloro-2-ethyl-1H-imidazole-5-carboxylic acid A solution of Intermediate 165 (4.25 g) and 2-methyl-2-butene (2M in THF; 45.6 ml) in dry THF (125 ml) and t-butanol (29 ml), under nitrogen atmosphere, was treated with a solution of sodium chlorite (80%; 6.87 g) and sodium dihydrogen phosphate dihydrate (6.87 g) in water (100 ml). The mixture was stirred at room temperature for 20 h. The layers were separated and the aqueous layer was extracted with diethyl ether (3×100 ml). The combined extracts were washed with water (200 ml), dried and concentrated in vacuo to give a yellow foam (4.8 g). This material was dissolved in 2M sodium hydroxide solution (50 ml) and then extracted once with diethyl ether (50 ml). The basic layer was acidified to pH3 using 2M HCl. The resultant solid was collected by filtration to give the title compound (3.8 g) as a white solid.

T.l.c.: System E (10:2.5:0.5) Rf=0.78
Similarly prepared were

Intermediate 170

1-[[3-Bromo-2-[2-[[(1,1-dimethylethoxy)carbonyl]amino]phenyl]5-benzofuranyl]methyl]-4-chloro-2-propyl-1H-imidazole-5-carboxylic acid T.l.c. System E (10:2.5:0.5) Rf=0.78
From Intermediate 166.

Intermediate 171

1-[[3-Bromo-2-[2-[[(1,1-dimethylethoxy)carbonyl]amino]phenyl-5-benzofuranyl]methyl]-2-ethyl-4-methyl-1H-imidazole-5-carboxylic acid n.m.r. (250 MHz, DMSO d$_6$) δ1.14(3H,t),2.42(3H,s), 2.62(2H,q),5.73(2H,s) 6.09(1H,dd),7.18(1H,brs),7.27(1H,dt),7.44–7.64(4H,m),-8.98(1H,br,s).

From Intermediate 167.

Intermediate 172

Ethyl 1-[[3-bromo-2-[2-[[(1,1-dimethylethoxy)carbonyl]amino]phenyl]-5-benzofuranyl]methyl]-4-chloro-2-ethyl-N-methyl-1H-imidazole-5-carboxamide Carbonyldiimidazole (0.507 g) was added to a solution of Intermediate 169 (0.6 g) in dry THF (30 ml), under nitrogen atmosphere, and the mixture was stirred at room temperature for 4 h. Methylamine 40% aqueous solution (1.3 ml) was added and the resulting solution was stirred at room temperature for 2 h. The solution was concentrated in vacuo and the residue was purified by flash chromatography eluting with diethyl ether to give the title compound (0.4 g) as a white solid, m.p. 95°–6°.

Intermediate 173

1-[[3-Bromo-2-[2-[[(1,1-dimethylethoxy)carbonyl ]amino]phenyl]-5-benzofurany]methyl]-2-ethyl-4-methyl-N-methyl-1H-imidazole-5-carboxamide n.m.r. (250 MHz, CDCl$_3$) δ1.34(3H,t),1.48(9H,s),2.53(3H,s),2.76(2H,q),2.96(3H,d-),5.63(2H,s),6.1–6.4(1H,vbr.s),7.-08–7.2(3H,m),7.28(1H,dd),7.-42–7.52(2H,m),7.62(1H,dd),8.15(1H,br.d)

From Intermediate 171.

Intermediate 174

1-[[3-Bromo-2-(2-aminophenyl)-5-benzofurany]methyl]-4-chloro-2-ethyl-N-methyl-1H-imidazole-5-carboxamide A solution of Intermediate 172 (0.4 g) in dry dichloromethane (20 ml), under nitrogen atmosphere, was cooled to 0° C. and trifluoroacetic acid (2 ml) was added. The resulting solution was stirred at room temperature for 3 h. Water (10 ml) was added and then aqueous ammonia (10 ml). The layers were separated. The organic phase was dried and concentrated in vacuo. The residue was purified by flash chromatography eluting with ether to give the title compound (0.3 g) as a white foam, m.p. 68°–70°.

Similarly prepared was

Intermediate 175

1-[[3-Bromo-2-(2-aminophenyl)-5-benzofuranyl]methyl]-2-ethyl-4-methyl-N-methyl-1H-imidazole-5-carboxamide T.l.c. System C (100:8:1) Rf=0.4
From Intermediate 173.

Intermediate 176

Ethyl 1-[[3-bromo-2-[2-[[(1,1-dimethylethoxy)carbonyl]amino]phenyl]-5-benzofuranyl]methyl]-4-chloro-2-ethyl-1H-imidazole-5-carboxylate A solution of diethyl azodicarboxylate (0.62 ml) in dry THF (10 ml) was added, dropwise, at room temperature under nitrogen atmosphere to a solution of Intermediate 169 (1.5 g) and triphenylphosphine (1.023 g) in ethanol (0.45 ml) and dry THF (65 ml). The resulting solution was stirred at room temperature for 20 h, and then concentrated in vacuo. The residue was purified by flash chromatography eluting with System A (3:7) to give the title compound (1.2 g) as a white foam, m.p. 73°–4°.

Similarly prepared were

Intermediate 177

Ethyl 1-[[3-bromo-2[2-[[(1,1-dimethylethoxy)carbonyl]amino]phenyl]-5-benzofuranyl]methyl]-4-chloro-2-propyl-1H-imidazole-5-carboxylate m.p. 68°–70° C.
From Intermediate 170.

Intermediate 178

Ethyl 1-[[3-bromo-2-[2-[[(1,1-dimethylethoxy)carbonyl]amino]phenyl]-5-benzofuranyl]methyl]-2-ethyl-4-methyl-1H-imidazole-5-carboxylate n.m.r. (250 MHz, CDCl$_3$) δ1.32(3H,t),1.48(9H,s),2.55(3H,s),2.7(2H,q),5.68(2H,s),-7.04(1H,dd),7.1–7.3(3H,m),7-.4–7.5(2H,m),7.63(1H,dd),8.19(1H,d).

From Intermediate 171.

Intermediate 179

Ethyl 1-[[3-bromo-2-(2-aminophenyl)-5-benzofuranyl]methyl]-4-chloro-2-ethyl-1H-imidazole-5-carboxylate A solution of Intermediate 176 (1.2 g) in dry dichloromethane (30 ml), under nitrogen atmosphere, was cooled to 0° C. and trifluoroacetic acid (6 ml) was added. The solution was stirred at room temperature for 3 h and was then concentrated in vacuo. Methanolic ammonia was added to the residue and the mixture was concentrated in vacuo. Purification of the residue by flash chromatography eluting with ether gave the title compound (0.8 g) as a white foam, m.p. 53°–56°.

Similarly prepared were

Intermediate 180 Ethyl

1-[[3-bromo-2-(2-aminophenyl)-5-benzofuranyl]methyl]-4-chloro-2-propyl-1H-imidazole-5-carboxylate m.p. 45°–46° C.
From Intermediate 177.

Intermediate 181

Ethyl 1-[[3-bromo-2-(2-aminophenyl)-5-benzofuranyl]methyl]-2,4-dimethyl-1H-imidazole-5-carboxylate m.p. 178°–179° C.
From Intermediate 168.

Intermediate 182

Ethyl 1-[[3-bromo-2-(2-aminophenyl)-5-benzofuranyl]methyl]-2-ethyl-4-methyl-1H-imidazole-5-carboxylate T.l.c. System C (100:8:1) Rf=0.5
From Intermediate 178.

Intermediate 183

Ethyl 1-[[3-bromo-[2-[2[[(1,1-dimethylethoxy)carbonyl-]amino]phenyl]-5-benzofuranyl]methyl]2,4-diethyl-1H-imidazole-5-carboxylate From Intermediate 162 and ethyl 2,4-diethyl-1H-imidazole-5-carboxylate according to the method of Intermediate 165.

T.l.c. ether Rf=0.48

Intermediate 184

Ethyl 1-[[3bromo-[2-(2-aminophenyl)-5-benzofuranyl]-methyl]-2,4-diethyl-1H-imidazole-5-carboxylate From Intermediate 183 according to the method of Intermediate 179.

m.p. 54°–55° C.

Intermediate 185

1,1-dimethylethyl 2-[[3-bromo-5-[(5-formyl-4methyl-2-propyl-1H-imidazol-1-yl)methyl]-2-benzofuranyl]-phenyl]carbamate From Intermediate 162 and 4-methyl-2-propyl-1H-imidazole-5-carboxaldehyde according to the method of Intermediate 165.

T.l.c. ether:acetic acid (10:1) Rf=0.45

Intermediate 186

1-[[3-Bromo-2-[2-[[(1,1-dimethylethoxy)carbonyl-]amino]phenyl]-5-benzofuranyl]methyl]-4-methyl-2-propyl-1H-imidazole-5-carboxylic acid From Intermediate 185 according to the method of Intermediate 169.

T.l.c. dichloromethane:methanol (10:1) Rf=0.3

Intermediate 187

1-[[3-Bromo-2-[2[[(1,1-dimethylethoxy)carbonyl-]amino]phenyl]-5-benzofuranyl]methyl]-N-ethyl-4-methyl-2-propyl-1H-imidazole-5-carboxamide From Intermediate 186 according to the method of Example 115.

T.l.c. dichloromethane:methanol (10:1) Rf=0.57

Intermediate 188

1-[[3-Bromo-2-(2-aminophenyl)-5-benzofuranylmethyl]-N-ethyl-4-methyl-2-propyl-1H-imidazole-5-carboxamide From Intermediate 187 according to the method of Intermediate 174.

T.l.c. dichloromethane:methanol (10:1) Rf=0.54

Intermediate 189

1-[[3-Bromo-2-[2-[[(1,1-dimethylethoxy)carbonyl-]amino]phenyl]-5-benzofuranyl]methyl]-4-methyl-2-propyl-1H-imidazole-5-carboxamide From Intermediate 186 according to the method of Example 103

T.l.c. dichloromethane:methanol (10:1) Rf=0.4

Intermediate 190

1-[[3-Bromo-2-(2-aminophenyl)-5-benzofuranyl]methyl]-4-methyl-2-propyl-1H-imidazole-5-carboxamide From Intermediate 187 according to the method of Intermediate 174.

T.l.c. dichloromethane:methanol (10:1) Rf=0.25

Intermediate 191

(2,2-Dimethyl-1-oxopropoxy)methyl 1-[[3-bromo-2-[2-[2-(triphenylmethyl)-2H-tetrazol-5-yl]phenyl]-5-benzofuranyl]methyl]-2-ethyl-4-methyl-1H-imidazole-5-carboxylate Potassium carbonate (92 mg) was added to a solution of Intermediate 148 (500 mg) in DMF (10 ml) and the resultant solution stirred at room temperature for 10 min prior to the addition of chloromethyl pivalate (96 μl) and the resultant solution stirred at room temperature for 72 h, The reaction mixture was poured into water (50 ml) and extracted into ethyl acetate (3×20 ml), The combined organics were washed with water (3×20 ml), dried and concentrated in vacuo to afford the title compound (433 mg) as a colourless glass, m.p. 51°–53° C.

Similarly prepared were

Intermediate 192

2-(Diethylamino)-2-oxoethyl 1-[[3-bromo-2-[2-[2-(triphenylmethyl)-2H-tetrazol-5-yl]phenyl]-benzofuranyl]-methyl]-2-ethyl-4-methyl-1H-imidazole-5-carboxylate as a glassy colourless solid (482 mg) m.p. 57°–59° C.

From a stirred solution of potassium carbonate (92 mg) and Intermediate 148 (500 mg) in DMF (10 ml), and 2-chloro-N,N-diethyl acetamide (91.6 μl).

Intermediate 193

(2-Methyl-1-oxopropoxy)methyl 1-[[3-bromo-2-[2-[2-(triphenylmethyl)-2H-tetrazol-5-yl]phenyl]-5-benzofuranyl]methyl]-2-ethyl-4-methyl-1H-imidazole-5-carboxylate as a colourless glass (537 mg) m.p. 92°–94° C.

From a stirred solution of potassium carbonate (92 mg) and Intermediate 148 (500 mg) in DMF (10 ml), and chloromethyl isobutyrate (91 mg).

Intermediate 194

1-[Ethoxycarbonyl)oxy]ethyl 1-[[3-bromo-2-[2-[2-(triphenylmethyl)-2H-tetrazol-5-yl]phenyl]-5-benzofuranyl]methyl]-2-ethyl-4-methyl-1H-imidazole-5-carboxylate as a colourless solid (533 mg) m.p. 67°–69° C.

From a stirred solution of potassium carbonate (92 mg) and Intermediate 148 (500 mg) in DMF (10 ml), and 1-chloroethyl ethylcarbonate (93 μl).

Intermediate 195

1-(Acetyloxy)ethyl 1-[[3-bromo-2-[2-[2-(triphenylmethyl)-2H-tetrazol-5-yl]phenyl]-5-benzofuranyl]methyl]-2-ethyl-4-methyl-1H-imidazole-5-carboxylate as a pale yellow foam (2.05 g) m.p. 62°–64° C.

From a stirred solution of potassium carbonate (368 mg) and Intermediate 148 (2.00 g) in DMF (30 ml), and bromomethyl acetate (446 mg).

Intermediates 196 to 200 were also prepared according to the method of Intermediate 191

Intermediate 196

(2,2-Dimethyl-1-oxopropoxy)methyl 1-[[3-bromo-2-[2-[2-(triphenylmethyl)-2H-tetrazol-5-yl]phenyl]-5-benzofuranyl]methyl]-4-chloro-2-ethyl-1H-imidazole-5-carboxylate m.p. 62°–65 ° C.

From Intermediate 70 and chloromethyl pivalate.

Intermediate 197

(2-(Diethylamino)-2-oxoethyl 1-[[3-bromo-2-[2-[2-(triphenylmethyl)-2H-tetrazol-5-yl]phenyl]-5-benzofuranyl]methyl]-4-chloro-2-ethyl-1H-imidazole-5-carboxylate m.p. 67°–69° C.

From Intermediate 70 and 2-chloro-N,N-diethyl acetamide.

Intermediate 198

(2-Methyl-1-oxopropoxy)methyl1-[[3-bromo-2-[2-[2-(triphenylmethyl)-2H-tetrazol-5-yl]phenyl]-5-benzofuranyl]methyl]-4-chloro-2-ethyl-1H-imidazole-5-carboxylate m.p. 92°–94° C.

From Intermediate 70 and chloromethyl isobutyrate.

Intermediate 199

1-[(Ethoxycarbonyl)oxy]ethyl1-[[3-bromo-2-[2-[2-(triphenylmethyl)-2H-tetrazol-5-yl]phenyl]-5-benzofuranyl]methyl]-4-chloro-2-ethyl-1H-imidazole-5-carboxylate m.p. 87°–89° C. (shrinks at 80°–82° C.)

From Intermediate 70 and 1-chloroethyl ethylcarbonate.

Intermediate 200

1-(Acetyloxy)ethyl-1-[[3-bromo-2-[2-[2-(triphenylmethyl)-2H-tetrazol-5-yl]phenyl]-5-benzofuranyl]methyl]-4-chloro-2-ethyl-1H-imidazole-5-carboxylate m.p 92°–94° C.

From Intermediate 70 and bromoethyl acetate.

Intermediate 201

1-(2-Methoxy-2-methyl1-oxpropoxy)ethyl 1-[[3-bromo-2-[2-[2-(triphenylmethyl)-2H-tetrazol-5-yl]phenyl]-5-benzofuranyl]methyl]-4-chloro-2-ethyl-1H-imidazole-5-carboxylate To a stirred suspension of Intermediate 70 (0.4 g) and potassium carbonate (75 mg) in dry DMF (5 ml) was added a solution of 1-(2-methoxy-2-methyl-1-oxopropoxy)ethylbromide (0.12 g) in DMF (2 ml) and the resulting mixture stirred overnight. Water (15 ml) was added and the mixture extracted with ether (3×15 ml). The extracts were washed with 10% lithium chloride solution (10 ml), dried and evaporated in vacuo. The residue was purified by chromatography eluting with ether:hexane (5:1) to give the title compound as a yellow foam (290 mg).

T.l.c. ether, Rf=0.76

Intermediate 202

1-(2-Methoxy2-methyl-1-oxopropoxy)ethyl 1-[[3-bromo-2-[2-[2-triphenylmethyl)-2H-tetrazol-5-yl]phenyl]-5-benzofuranyl]methyl]-2-ethyl-4-methyl-1H imidazole-5-carboxylate To a stirred suspension of Intermediate 148 (0.4 g) and potassium carbonate (75 mg) in dry DMF (5 ml) was added a solution of 1-(2-methoxy-2-methyl-1-oxopropoxy)ethylbromide (0.12 g) in DMF (2 ml) and the resulting mixture stirred overnight. Water (15 ml) was added to the reaction which was then extracted with ether (3×15 ml). The extracts were washed with 10% lithium chloride solution (10 ml), dried and evaporated in vacuo. The residue was purified by chromatography eluting with ether to give the title compound as a white foam (230 mg).

T.l.c. ether, Rf=0.33

Intermediate 203

(R,S)-Dihydro-2(3H)-furanone-5yl 1-[[3-bromo-2-[2-[2-(triphenylmethyl)-2H-tetrazol-5-yl]phenyl]-5-benzofuranyl]methyl]-2-ethyl-4-methyl-1H-imidazole-5-carboxylate From intermediate 148 and 4-chloro-2,3-dihydrofuran-1-one according to the method of Intermediate 191.

n.m.r. (250 MHz, CDCl$_3$) δ1.27(3H,t),2.1–2.8(9H,m+s),5.6(2-H,AB),6.68(1H,d),6.75–7.3(18H,m),7.5–7.72(3H,m),8.19(1H,dd).

Intermediate 204

(R,S)-Dihydro-2(3H)-furanone-5-yl 1-[[3-bromo-2-[2-[2-(triphenylmethyl)-2H-tetrazol-5-yl]phenyl]-5-benzofuranyl]methyl]-4-chloro-2-ethyl-1H-imidazole-5-carboxylate From Intermediate 70 and 4-chloro-2,3-dihydrofuran-1-one according to the method of Intermediate 191.

n.m.r. (250 MHz, CDCl$_3$) δ1.27(3H,t),2.2–2.9(6H,m),5.6(2H,AB),6.67(1H,d),6.72–7.33(18H,m),7.52–7.72(3H,m),8.2(1H,dd).

Intermediate 205

1,1-Dimethylethyl2-(3-bromo-5-methyl-2-benzofuranyl)benzoate

From Intermediate 1 and 1,1-dimethylethyl 2-bromobenzoate according to the method of Intermediate 2, followed by bromination according to the method of Intermediate 5.

T.l.c. dichloromethane:hexane (1:2) Rf=0.3

Intermediate 206

1,1-Dimethylethyl2-[3-bromo-5-(bromomethyl)-2-benzofuranyl]benzoate

From intermediate 205 according to the method of Intermediate 6.

T.l.c. System A (1:10) Rf=0.4

Intermediate 207

Ethyl 1-[[3-bromo-2-[2-[[(1,1-dimethylethoxy)carbonyl]amino]phenyl]-5-benzofuranyl]methyl]-2-ethyl-4-(2-methylpropyl)-1H-imidazole-5carboxylate From Intermediate 162 and ethyl 2-ethyl-4-(2-methylpropyl)-1H-imidazole-5carboxylate according to the method of Intermediate 165. t.l.c. ether Rf=0.50

Intermediate 208

Ethyl 1-[[3-bromo-2-(2-aminophenyl)-5-benzofuranyl]methyl]-2-ethyl-4-(2-methylpropyl)-1H-imidazole-5-carboxylate From Intermediate 207 according to the method of Intermediate 179.

t.l.c. ether Rf=0.44

EXAMPLE 93

1-[[3-Bromo-2-[2-[(trifluoromethyl)sulphonyl]amino]phenyl]-5-benzofuranyl]methyl-4-chloro-2-ethyl-N-methyl-1H-imidazole-5-carboxamide A solution of Intermediate 174 (0.28 g) and dry triethylamine (0.08 ml) in dry dichloromethane (9 ml) was cooled to −95° C., under nitrogen atmosphere, and a solution of trifluoromethanesulphonic anhydride (0.116 ml) in dry dichloromethane (1 ml) was added. The mixture was stirred at −95° to −75° for 1 h. Water (5 ml) was added, the layers were separated and the organic phase was washed with 2N HCl (10 ml). The organic solution was dried and concentrated in vacuo to give a foam which was purified by flash chromatography eluting with chloroform/methanol (75:2.5) to give the title compound (0.2 g) as a white solid, m.p. 105°–6° (dec.).

T.l.c. chloroform/methanol (15:0.5) Rf=0.47

Similarly prepared were

EXAMPLE 94

1-[[3-Bromo-2-[2-[[(trifluoromethyl)sulphonyl]amino]phenyl]-5-benzofuranyl]methyl]-2-ethyl-4-methyl-N-methyl-1H-imidazole-5-carboxamide m.p. 165°–175° C. (shrinks 155° C.) MH+599
From Intermediate 175.

EXAMPLE 95

Ethyl 1-[[3-bromo-2-[2-[[(trifluoromethyl)sulphonyl]amino]phenyl]-5-benzofuranyl]methyl]-4-chloro-2-ethyl-1H-imidazole-5-carboxylate m.p. 89°–90° C. T.l.c. ether Rf=0.65
From Intermediate 179.

EXAMPLE 96

Ethyl 1-[[3-bromo-2-[2-[[(trifluoromethyl)sulphonyl]amino]phenyl]5-benzofuranyl]methyl]-4-chloro-2-propyl-1H-imidazole-5-carboxylate m.p. 77°–78° C.
T.l.c. chloroform:methanol (20:0:5) Rf=0.67
From Intermediate 180.

EXAMPLE 97

Ethyl 1-[[3-bromo-2-[2-[[(trifluoromethyl)sulphonyl]amino]phenyl]-5-benzofuranyl]methyl]-2,4-dimethyl-1H-imidazole-5-carboxylate m.p. 226–7 (dec)
T.l.c. ethyl acetate Rf=0.39
From Intermediate 181.

EXAMPLE 98

Ethyl 1-[[3-bromo-2-[2-[[(trifluoromethyl)sulphonyl]amino]phenyl]-5-benzofuranyl]methyl]-2-ethyl-4-methyl-1H-imidazole-5-carboxylate m.p. 105°–107° C. Assay Found: C,48.61H,3.7; N,6.55 $C_{25}H_{23}BrF_3N_3O_5S$ requires C,48.9; H,3.8; N,6.8%
From Intermediate 182.

EXAMPLE 99

1-[[3-Bromo-2-[2-[[(trifluoromethyl)sulphonyl]amino]phenyl]-5-benzofuranyl]methyl]-4-chloro-2-ethyl-1H-imidazole-5-carboxylic acid A solution of product of Example 95 (0.4 g) in methanol (20 ml) and 2M NaOH (4 ml) was heated at reflux for 1.5 h. The solution was concentrated in vacuo. It was then diluted with water (10 ml) and extracted with diethyl ether (10 ml). The aqueous layer was acidified to pH5 with 2N HCl and extracted with ethyl acetate (3×20 ml). The combined organic extracts were dried and concentrated in vacuo to give the title compound (0.35 g) as a pale beige solid, m.p. 109°–110° (dec.).

T.l.c. dichloromethane/methanol 10:0.5, Rf=0.43
Similarly prepared were

EXAMPLE 100

1-[[3-Bromo-2-[2-[[(trifluoromethyl)sulphonyl]amino]phenyl]-5-benzofuranyl[methyl[-4-chloro-2-propyl-1H-imidazole-5-carboxylic acid m.p. 174°–175° C. (dec) T.l.c. System E (10:2.5:0.5) Rf=0.72
From the product of Example 96.

EXAMPLE 101

1-[[3-Bromo-2-[2-[[(trifluoromethyl)sulphonyl]amino]phenyl]-5-benzofuranyl]methyl]-2,4-dimethyl-1H-imidazole-5-carboxylic acid m.p. 184°–185° C. (dec) T.l.c. dichloromethane:methanol:acetic acid (10:1:0.5) Rf=0.23
From the product of Example 97.

EXAMPLE 102

1-[[3-Bromo-2-[2-[[(trifluoromethyl)sulphonyl]amino]phenyl]-5-benzofuranyl]methyl]-2-ethyl-4-methyl 1H-imidazole-5-carboxylic acid m.p. 153°–155° C. MH+586.0
From the product of Example 98.

EXAMPLE 103

1-[[3-Bromo-2-[2-[[(trifluoromethyl)sulphonyl]amino]phenyl]-5-benzofuranyl]methyl]-4-chloro-2-ethyl-1H-imidazole-5-carboxamide Carbonyldiimidazole (0.12 g) was added to a solution of the product of Example 99 (0.15 g) in dry THF (5 ml) under a nitrogen atmosphere. The resulting solution was stirred at room temperature for 3 h. Ammonia 35% aqueous solution (0.2 ml) was added and the resulting solution was stirred at room temperature for 2 h. The solution was concentrated in vacuo, then diluted with ethyl acetate (20 ml) and washed with water (2×15 ml). The organic layer was dried and concentrated in vacuo to a solid which was crystallized from methyl acetate/n-hexane to give the title compound (0.14 g) as a white solid, m.p. 68°–70° C.

T.l.c. System E (10:2.5:0.5) Rf=0.43
Similarly prepared was

Example 104

1-[[3-Bromo-2-[2-[[(trifluoromethyl)sulphonyl]amino]phenyl]-5-benzofuranyl]methyl]-4-chloro-N-methyl-2-propyl-1H-imidazole-5-carboxamide T.l.c. chloroform/methanol (20:2.5) Rf=0.61
From the product of Example 100 and methylamine.

Example 105

1-[[3-Bromo-2-[2-[[(trifluoromethyl)sulphonyl]amino]phenyl]-5-benzofuranyl]methyl]-2,4-dimethyl-N-methyl-1H-imidazole-5-carboxamide Carbonyldiimidazole (0.17 g) was added to a solution of the product of Example 101 (0.2 g) in dry THF (15 ml) under a nitrogen atmosphere. The resulting solution was stirred at room temperature for 4 h, concentrated in vacuo to ~5 ml and then poured into an autoclave with 20 ml of liquid methylamine. The autoclave was heated to 60° C. for 1.5 h and then cooled to −40° C. before opening. The solution was diluted with cold methanol (−35° C.; 50 ml). The resulting solution was concentrated in vacuo and the residue was purified by flash chromatography eluting with chloroform-methanol (10:3) followed by another column eluted with 10–20% methanol in ethyl acetate to give the title compound as a white solid (104 mg), m.p. 208°–210° C.

T.l.c. 20% methanol in ethyl acetate, Rf0.34

Example 106

Ethyl 1-[[3-bromo-2-[2-[[(trifluoromethyl)sulphonyl]amino]phenyl]-5-benzofuranyl]methyl]-2,4-diethyl-1H-imidazole-5-carboxylate From Intermediate 184 according to the method of Example 93.
m.p. 99°–101° C.

Example 107

1-[[3-Bromo-2-[2-[[(trifluoromethyl)suphonyl]amino]-phenyl]-5-benzofuranyl]methyl]-2,4-diethyl-1H-imidazole-5-carboxylic acid From the product of Example 106 according to the method of Example 99.
T.l.c dichloromethane:methanol (10:1) Rf=0.14

Example 108

1-[[3-Bromo-2-[2-[[(trifluoromethyl)sulphonyl]amino]-phenyl]-5-benzofuranyl]methyl-]N-ethyl-4-methyl-2-propyl-1H-imidazole-5-carboxamide From Intermediate 188 according to the method of Example 93.

Example 109

1-[[3-Bromo-2-[2-[[(trifluoromethyl)sulphonyl]amino]-phenyl]-5-benzofuranyl]methyl-]-4-chloro-2-propyl-1H-imidazole-5-carboxamide From the product of Example 100 according to the method of Example 103.
m.p. 198°–200° C. Analysis Found: C,44.6; H.3.0; N,8.95 $C_{23}H_{19}BrClF_3N_4O_4S$ requires C,44.6; H.3.1; N,9.0%

Example 110

1-[[3-Bromo-2-[2-[[(trifluoromethyl)sulphonyl]amino]-phenyl]-5-benzofuranyl]methyl]-2-ethyl-4-methyl-1H-imidazole-5-carboxamide From the product of Example 102 according to the method of Example 103.
m.p. 118°–124° C.

No Examples corresponding to numbers 111 and 112.

Example 113

1-[[3-Bromo-2-[2-[[(trifluoromethyl)sulphonyl]amino]-phenyl]-5-benzofuranyl]methyl]-4-methyl-2-propyl-1H-imidazole-5-carboxamide From Intermediate 190 according to the method of Example 93.

Example 114

1-[[3-Bromo-2-[2-[[(trifluoromethyl)sulphonyl]amino]-phenyl]-5-benzofuranyl]methyl]-N,4-dimethyl-2-propyl-1H-imidazole-5-carboxamide From the product of Example 91 and methylamine according to the method of Example 103.
m.p. 164°–170° C. Analysis Found: C,49.1; H,4.1; N,8.8 $C_{25}H_{24}BrF_3N_4O_4S$ requires: C,48.9; H,3.9; N,9.1%

EXAMPLE 115

1-[[3-Bromo-2-[2-[[(trifluoromethyl)sulphonyl]amino]-phenyl]-5-benzofuranyl]methyl]-N,2-diethyl-4-methyl-1H-imidazole-5-carboxamide 1,1-Carbonyldiimidazole (0.181 g) was added to a stirred solution of the product of Example 102 (0.403 g) in dry THF (25 ml). After stirring for 4 h at room temperature the solution was allowed to stand at room temperature overnight. 70% Aqueous ethylamine (15 ml) was added and the mixture heated with stirring for 1.25 h. After cooling, the solution was partitioned between ethyl acetate (30 ml) and 10% brine (30 ml). The separated aqueous phase was further extracted with ethyl acetate (3×20 ml) and the combined organic extracts were dried, concentrated in vacuo and azeotroped with toluene (3×15 ml) to afford an orange oil (0.7 g). This oil was dissolved in ethyl acetate (40 ml) and washed with 2N hydrochloric acid (1×30 ml, 1×15 ml), dried and concentrated in vacuo to afford an off-white foam (0.31 g). Purification by chromatography eluting with a gradient of System C (150:8:1)→(50:8:1) afforded the title compound (0.25 g) as a white foam, m.p. 110°–115° (softens), melts 140°.
N.m.r. -(DMSOd$_6$)
δ1.08(t,3H),1.25(t,3H),2.3(s,3H),3.0(q,2H),3.28(m,2H), 5.6(br s,2H),6.8–7.6(m,8H),8.5(m,1H).

EXAMPLE 116

1-[[3-Bromo-2-[2-[[(trifluoromethyl)sulphonyl]amino]-phenyl]-5-benzofuranyl]methyl]-4-chloro-N,2-diethyl-1H-imidazole-5-carboxamide From the product of Example 99 according to the method of Example 115.
m.p. 104°–110° C. T.l.c. System E (10:2:0.5) Rf=0.7

EXAMPLE 117

1-[[3-Bromo-2-[2-[[(trifluoromethyl)sulphonyl]amino]-phenyl]-5-benzofuranyl]methyl]-4-chloro-N-ethyl,2-propyl-1H-imidazole-5-carboxamide.

From the product of Example 100 according to the method of Example 115.
m.p. 172° C. Analysis Found C,46.7; H,3.7; N.8.45 $C_{25}H_{23}BrClF_3N_4O_4S$ requires C,46.35; H,3.6; N,8.65%

EXAMPLE 118

1-(2-Methoxy-2-methyl-1-oxopropoxy)ethyl1-[[3-bromo-[2-(1H-tetrazol-5-yl)phenyl]-5-benzofuranyl]methyl]2-ethyl-4-methyl-1H-imidazole-5-carboxylate A solution of Intermediate 202 (220 mg) in ethanol (5 ml) and conc. hydrochloric acid (2 ml) was stirred at room temperature for 3 h. The pH of the solution was adjusted to ~8–9 with 8% sodium bicarbonate and the mixture extracted with ethyl acetate (3×20 ml). The dried organic extracts were evaporated in vacuo and the residue purified by chromatography eluting with ethyl acetate then ethyl acetate:acetic acid (20:1) to give the title compound as a white solid (150 mg) m.p. 135°–140° C.
T.l.c. ethyl acetate:acetic acid (20:1), Rf=0.51
Examples 119 to 123 were prepared in a similar manner from Intermediates 191 to 195, respectively

EXAMPLE 119

(2,2-Dimethyl-1-oxoropoxy)methyl1-[[3-bromo-2-[2-(1H-tetrazol-5-yl)phenyl]-5-benzofuranyl]methyl ]-2-ethyl-4-methyl-1H-imidazole-5-carboxylate
m.p. 129°–132° C. T.l.c. ether Rf=0.08

EXAMPLE 120

27(Diethylamino)-2-oxoethyl1-[[3-bromo-2-[2-(1H-tetrazol,5-yl)phenyl]-5-benzofuranyl]methyl]-2-ethyl-4-methyl-1H-imidazole-5-carboxylate
m.p. 125°–128° C. T.l.c. ethyl acetate Rf=0.09

EXAMPLE 121

(2-Methyl-1-oxopropoxy)methyl1-[[3-bromo-2-[2-(1H-tetrazol-5-yl)phenyl]-5-benzofuranyl]methyl]-2-ethyl-4-methyl-1H-imidazole-5-carboxylate
m.p. 106°–108° C. T.l.c. ether Rf=0.09 (the title compound was obtained following column chromatography eluting with 5% ethanol in ether).

EXAMPLE 122

1-[(Ethoxycarbonyl)oxy]ethyl 1-[[3-bromo-2-[2-(1H-tetrazol-5-yl)phenyl]-5-benzofuranyl]methyl]-2-ethyl-4-methyl-1H-imidazole-5-carboxylate m.p. 139°–142° C. T.l.c. ethyl acetate Rf=0.09

EXAMPLE 123

1-(Acetyloxy)ethyl 1-[[3-bromo-2-[2-(1H-tetrazol-5-yl)phenyl]-5-benzofuranyl]methyl]-2-ethyl-4-methyl-1H-imidazole-5-carboxylate m.p. 125°–128° C. T.l.c. ether Rf=0.09

EXAMPLE 124

1-(2-Methoxy-2-methyl-1-oxopropoxy)ethyl 1-[3-bromo-2-[2-(2H-tetrazol-5-yl )phenyl]-5-benzofuranyl]methyl]-4-chloro-2-ethyl-1H-imidazole-5-carboxylate A solution of Intermediate 201 (280 mg) in ethanol (5 ml) and conc. hydrochloric acid (2 ml) was stirred at room temperature for 3 h. The pH of the solution was adjusted to ~10 with 2N sodium bicarbonate and the mixture extracted with ether (2×20 ml). The aqueous was acidified with 2N hydrochloric acid and extracted with ether (3×30 ml). The dried extracts were evaporated in vacuo to a whim foam which was purified by h.p.l.c. to give the title compound as a white solid (55 mg)

m.p. 109°–111° C. Analysis Found C,51.5; H,4.2; N,12.3; $C_{29}H_{28}BrClN_6O_6$ requires C,51.8; H,4.2; N,12.5%

Examples 125 to 129 were prepared in a similar manner from Intermediate 196 to 200, respectively

EXAMPLE 125

(2,2-Dimethyl-1-oxopropoxy)methyl 1-[[3-bromo-2-[2-(1H-tetrazol-5-yl)pheny]-5-benzofuranyl]methyl]-4-chloro-2-ethyl-1H-imidazole-5-carboxylate m.p. 125°–128° C. T.l.c. ether Rf=0.10

EXAMPLE 126

-(Diethylamino)-2-oxoethyl 1-[[3-bromo-2-[2-(1H-tetrazol-5-yl)phenyl]-5-benzofuranyl]methyl]-4-chloro-2-ethyl-4-methyl-1H-imidazole-5-carboxylate m.p. 109°–111° C. T.l.c. ether Rf=0.12

EXAMPLE 127

(2-Methyl-1-oxopropoxy)methyl 1-[[3-bromo-2-[2-(1H-tetrazol-5-yl)phenyl]-5-benzofuranyl]methyl]-4-chloro-2-ethyl-1H-imidazole-5-carboxylate m.p. 112°–115° C. T.l.c. ether Rf=0.12 (the title compound was obtained following column chromatography eluting with 5% ethanol in ether).

EXAMPLE 128

1-[(Ethoxyeaxbonyl)oxy]ethyl 1-[[3-bromo-2-[2-(1H-tetrazol-5-yl)phenyl]-5-benzofuranyl]methyl-4-chloro-2-ethyl-1H-imidazole-5-carboxylate m.p. 147°–150° C. T.l.c. ether Rf=0.21

EXAMPLE 129

1-(Acetyloxy)ethyl 1-[[3-bromo-2-[2-(1H-tetrazol-5-yl]phenyl]-5-benzofuranyl]methyl]-4-chloro-2-ethyl-4-methyl-1H-imidazole-5-carboxylate m.p. 125°–128° C. T.l.c. ether Rf=0.09

EXAMPLE 130

(R,S)-Dihydro-2(3 H)-furanone-5-yl 1-[[3-bromo-2-[2-(1H-tetrazol-5-yl)phenyl]-5-benzofuranyl]methyl]-2-ethyl-4-methyl-1H-imidazole-5-carboxylate From Intermediate 203 according to the method of example 118.

m.p. 163° C. (decomp) hplc: Dynamax $C_{18}$ Pk5, 15cm×4.6 mm i.d. column mobile phase:acetonitrile/water (containing 20 mmol.l$^{-1}$ ammonium acetate),- 0°–30% over 15 mins Detection λ=230 nm. Retention time=27.2 minutes.

EXAMPLE 131

(R,S)-Dihydro-2(3H)-furanone-5-yl 1-[[3-bromo-2-[2-(1H-tetrazol-5-yl)phenyl]-5-benzofuranyl]methyl]-4-chloro-2-ethyl-1H-imidazole-5-carboxylate From Intermediate 204 according to the method of example 124.

m.p. 155°–160° C. (decomp) hplc: (conditions as in Example 130, except Detection λ=300 nm) Retention time=27.2 minutes.

Examples 132 to 135 were prepared according to the method of Intermediate 4.

EXAMPLE 132

Ethyl 2-[3-bromo-5-[(2-ethyl-5-formyl-4-methyl-1H-imidazol-1-yl)methyl]-2-benzofuranyl]benzoate From Intermediate 101 and Intermediate 146.

T.l.c. System A (1:10) Rf=0.2

EXAMPLE 133

1,1-Dimethylethyl 2-[3-bromo-5-[(2-ethyl-5-formyl-4-methyl-1H-imidazol-1-yl)methyl]-2-benzofuranyl]benzoate From Intermediate 206 and Intermediate 146.

T.l.c. dichloromethane:methanol (20:1) Rf=0.7

EXAMPLE 134

Methyl 2-[3-bromo-5-[(2-ethyl-5-formyl-4-methyl-1H-imidazol-1-yl)methyl]-2-benzofuranyl]benzoate From Intermediate 6 and Intermediate 146.

m.p. 58° C. (softens).

EXAMPLE 135

Methyl 2-[3-bromo-5-[(4-chloro-2-ethyl-5-formyl-1H-imidazol-1-yl)methyl]-2-benzofuranyl]benzoate From Intermediate 6 and Intermediate 151.

T.l.c. ethyl acetate:hexane (1:1) Rf=0.4 Analysis Found C,54.6; H,3.5; N,5.2 $C_{23}H_{18}BrClN_2O_4$ requires C,55.0; H,3.6; N,5.6%

EXAMPLE 136

1-[[3-Bromo-2-[2-(methoxycarbonyl)phenyl]-5-benzofuranyl]methyl]-2-butyl-4-chloro-1H-imidazole-5-carboxylic acid A solution of sodium chlorite (80% tech, 2.71 g) and sodium dihydrogen orthophosphate (2.99 g) in water (50 ml) was added to a mixture of methyl 2-[3-bromo-5-(2-butyl-4-chloro-5-formyl-1H-imidazol-1-yl) methyl]-2benzofuranyl]benzoate (2.6 g) and 2-methylbut-2-ene (2M in THF, 20 ml) in THF (60 ml) and t-butanol (60 ml). The mixture was vigorously stirred for 19 h before being concentrated partially in vacuo to afford a pasty white suspension. This suspension was dissolved in 8% sodium bicarbonate (150 ml) and methanol (10 ml) before 2N sodium hydroxide (approx. 5 ml) was added to give a solution pH of 12. This was washed with ether (2×50 ml) before being cautiously acidified with 2N hydrochloric acid. This was extracted with ethyl acetate (4×70 ml) and the combined organic extracts were dried and concentrated in vacuo to afford the title compound (2.45 g) as an off-white foam.

T.l.c. ether, Rf 0.1 N.m.r.(250 MHz CDCl$_3$) δ0.9(t,3H),1.35(m,2H),1.7(m,2H),2.7(t,2H),3.65(s,3H),5.7(brs,2H),7.0-7.8(m,6H),7.95(dd,1H).

Similarly prepared were

EXAMPLE 137

2-Butyl-4-chloro-1-[[3-bromo-2-[2-[(phenylmethoxy)carbonyl]phenyl]-5-benzofuranyl]methyl]-1H-imidazole-5-carboxylic acid as a brown foam (1.44 g) N.m.r (DMSOd$_6$) δ0.82(t,3H),1.3(m,2H),1.58(m,2H),2.69(t,2H),5.15(s,2H-), 5.8(s,2H),7.0 -7.3 (m,7H),7.58(d,1H),7.7-7.85(m,3H),8.0 (d, 1H)

From Phenylmethyl 2-[3-bromo-5-[(2-butyl-4-chloro-5-formyl-1H-imidazol-1-yl)methyl-2-benzofuranyl]benzoate.

EXAMPLE 138

1-[[3-Bromo-2-[2-(ethoxycarbonyl)phenyl]-5-benzofuranyl]methyl]-2-ethyl-4-methyl-1H-imidazole-5-carboxylic acid T.l.c. dichloromethane:methanol (10:1) Rf=0.45 Analysis Found: C,56.4; H,4.5; N,5.1C$_{25}$H$_{23}$BrN$_2$O$_5$.H$_2$O requires: C,56.7; H,4.6; N,5.3%

From the product of Example 132.

EXAMPLE 139

1-[[3-Bromo-2-[2-(methoxycarbonyl)phenyl]-5benzofuranyl]methyl]-2ethyl-4-methyl-1H-imidazole-5-carboxylic acid m.p. 185° C. MH+(calc) 497, (obs) 497.

From the product of Example 134.

EXAMPLE 140

1-[[3-Bromo-2-[2-(methoxycarbonyl)phenyl]-5-benzofuranyl]methyl ]-4-chloro-2-ethyl-1H-imidazole-5-carboxylic acid m.p. 156° C. Analysis Found: C,53.0; H,3.4; N,5.1C$_{23}$H$_{18}$BrClN$_2$O$_5$ requires: C,53.35; H,3.5; N,5.4%

EXAMPLE 141

1-[[3-Bromo-2-[2-[[(1,1-dimethylethoxy)carbonyl]phenyl]-5-benzofuranyl]methyl]2-ethyl-4-methyl-1H-imidazole-5-carboxylic acid From the product of Example 133.

EXAMPLE 142

Ethyl 2-butyl-4-chloro-1-[[3-bromo-2-[2-[(phenylmethoxy)carbonyl]phenyl]-5-benzofuranyl]methyl]-1H-imidazole-5-carboxylate A solution of diethyl azodicarboxylate (0.41 g) in THF (20 ml) was added dropwise to a stirred solution of the product of Example 137 (0.73 g) and triphenylphosphine (0.645 g) in ethanol (0.7 ml) and THF (20 ml). After stirring at room temperature for 16 h, the solution was concentrated in vacuo to afford a yellow gum (2.22 g). Purification by chromatography eluting with a gradient of System A (1:4) increasing to (1:1) afforded the title compound (0.75 g) as a colourless gum.

T.l.c. System A (1:1) Rf0.5 N.m.r. (250 MHz, CDCl$_3$) δ0.9(t,3H),1.35(m,5H),1.75(m,2H),2.7(t,2H), 4.3(q,2H),5.15(s,2H),5.65(s,2H),6.95(d,2H),7.1-7.3(m,7-H),7.5-7.75(m,3H),8.0(d,1H)

Similarly prepared were

EXAMPLE 143

Ethyl 2-butyl-4-chloro-1-[[3-bromo-2-[2-(methoxycarbonyl)phenyl]-5-benzofuranyl]methyl]-1H-imidazole-5-carboxylate hplc Retention time=10.8 minutes n.m.r. (250 MHz, CDCl$_3$) δ0.9(t,3H),1.3-1.45(m,5H),1.72(m,2H),2.68(t,2H), 3.75(s,3H),4.3(q,2H)5.68(br s,2H),7.0 (dd,1H),7.2(br s, 1H),7.43(d,1H), 7.5-7.7(m,2H),7.75(dd,1H),7.98(dd,1H). From the product of Example 136.

EXAMPLE 144

Ethyl 1-[[3-bromo-2[2[(1,1-dimethylethyloxy)carbonyl]phenyl]-5-benzofuranyl]methyl]-2-ethyl-4-methyl-1-H-imidazole-5-carboylate T.l.c. dichloromethane/methanol (20:1) Rf 0.47

From the product of

Example 141.

Examples 145 and 146 were prepared according to the method of Example 52

EXAMPLE 145

1-[[3-Bromo-2-(2-carboxyphenyl)-5-benzofuranyl]methyl]-2-ethyl-4-methyl-1H-imidazole-5-carboxylic acid From the product of Example 138.

m.p. 220°-221 ° C. t.l.c. ethyl acetate:methanol:acetic acid (20:1:1) Rf=0.25

EXAMPLE 146

1-[[3-Bromo-2-(2-carboxyphenyl)-5-benzofuranyl]-methyl-4-chloro-2ethyl-1H-imidazole-5-carboxylic acid From the product of 140.

m.p. 229° C. T.l.c. ethyl acetate:acetic acid (10:1) Rf=0.7

EXAMPLE 147

Methyl 1-[[3-bromo-2-(2-methoxycarbonyl)phenyl]-5-benzofuranyl]methyl]-2 -ethyl-4-methyl1H-imidazole-5-carboxylate From the product of Example 139 according to the method of Intermediate 30.

m.p. 53° C. (softens) Analysis Found: C,58.7; H,4.6; N,5.2C$_{25}$H$_{23}$BrNO$_5$ requires: C,58.7; H,4.5; N,5.5%

EXAMPLE 148

Ethyl 1-[[3-bromo-2-[2-(ethoxycarbonyl)phenyl-5-benzofuranyl]methyl]-4-chloro-2-ethyl-1H-imidazole-5-carboxylate A solution of the product of Example 140 (1 g) in absolute ethanol (20 ml) and -conc. sulphuric acid (2.5 ml) was heated at reflux for 3 days. Anhydrous sodium carbonate was added and the solvent was removed in vacuo. The residue was dissolved in water (25 ml) and the product was extracted with dichloromethane (50 ml). The organic solution was dried and evaporated in vacuo. The residue was purified by flash column chromatography eluting with System A (3:5)to give the title compound as a white solid (0.4 g) m.p. 116°–7° C.

Analysis Found: C,55.7; H,4.3,N,4.75;C$_{26}$H$_{24}$BrCN$_2$O$_5$ requires, C,55.8; H,4.3; N,5.0%

EXAMPLE 149

1-[[3-Bromo-2-(2-ethoxycarbonyl)phenyl]-5-benzofuranyl]methyl]-4-chloro-2-ethyl-1H-imidazole-5-carboxylic acid A solution of the product of example 148 (0.25 g) and lithium hydroxide (35 mg) in a mixture of THF (7 ml) and water (5 ml) was stirred at ambient temperature for 4 h. Hydrochloric acid (2M) was cautiously added until pH of solution was 4.5. The organic solvent was removed in vacuo and the aqueous residue was extracted with ethyl acetate (3×50 ml). The organic extract was dried and evaporated to give an oily residue. The residue was purified by flash column chromatography eluting with ether/hexane/acetic acid (200:200:1) to give a solid residue. The residue was crystallised from methyl acetic/hexane to give the title compound as a white solid (80 mg) m.p. 168°–170° C. Analysis Found: C,54.1; H,3.6; N,4.9C$_{24}$H$_{20}$BrClN$_2$O$_5$ requires C,54.2; H,3.8; N,5.3%

EXAMPLE 150

Ethyl 1-[[3-bromo-2-(2-carboxyphenyl)-5-benzofuranyl]methyl]-2-ethyl-4-methyl-1H-imidazole-5-carboxylate Trifluoroacetic acid (7 ml) was added dropwise to a stirred solution of the product of Example 144 (0.892 g) in dichloromethane (30 ml)cooled to 0° C. After 2½ h the solvent was removed in vacuo to yield an orange oil. The oil was diluted with dichloromethane, washed with hydrochloric acid, dried and the solvent removed in vacuo. The residue was purified by flash column chromatography eluting with dichloromethane/methanol (30:1) to give the title compound as a white solid (200 mg).

T.l.c. Dichloromethane/methanol (20:1), Rf 0.26 N.m.r. δ8.10(1H,dd),7.67(1H,dd),7.55 –7.65(2H,m),7.32(1H,d),7.22(1H,s),6.8(1H,d),5.65(2H,s),4.28(2H,q),2.5 (3H,s),2.44(2H,q),1.32(3H,t),

EXAMPLE 151

Methyl 2-[[3-Bromo-5-[[2-butyl-4-chloro-5-[(methylamino)carbonyl]-1H-imidazol-1-yl]methyl-2-benzofurany]benzoate 1,1-Carbonyldiimidazole (0.16 g) was added to a solution of the product of Example 136 (0.38 g) in THF (35 ml). After stirring for 1 h under nitrogen, methylamine gas was bubbled through the solution for 10 min. The mixture was then stirred over the weekend under nitrogen before being concentrated in vacuo to afford a yellow oil (0.55 g). Purification by chromatography eluting with System A (1:4) increasing to ether afforded the title compound (0.17 g) as an off-white foam.

T.l.c. System A (1:1) Rf 0.25 N.m.r. (CDCl$_3$) δ0.9(t,3H),1.35(m,2H),1.7(m,2H),2.65(t,2H)2.97(d,3.65-(t,3H),5.8(s,2H),6.65(m,1H)7.05(dd,1H),7.2(brs,1H),7.4-(d,1H),7.5–7.7(m,2H),7.75(dd,1H),7.95(dd,1H).

EXAMPLE 152

2-[[3-Bromo-5-[[2-butyl4-chloro-5-[(methylamino)carbonyl]-1H-imidazol-1-yl]methyl-2-benzofurany l]benzoate 2N Sodium hydrocide (1.5m) was added to a sitrred solution of the product of Example 151 (0.19 g) in THF (20 ml) and methanol (10 ml). After stirring for 36 h, the mixture was acidified to pH2.5 with 2N hydrochloric acid and then concentrated in vacuo to afford a residue which was partitioned between ethyl acetate (50 ml) and water (50 ml). The separated aqueous phase was further extracted with ethyl acetate (1×40 ml) and the combined organic extracts were dried and concentrated in vacuo to afford the title compound (0.142 g) as an off-white foam m.p. 87°–90°

N.m.r. (DMSOd$_6$) δ0.83(t,3H),1.3,(m,2H),1.55(m,2H),2.65(t,2H),2.77(d,3-H), 5.6(brs,2H),7.2(dd,1H)7.32(d,1H),7.6°14 7.75(m,3H),7.93(d,1H),8.15(m,1H)

EXAMPLE 153

Ethyl 1-[[3-bromo-2-[2-(ethoxycarbonyl)phenyl]-5-benzofuranyl]-methyl], -2,4-dimethyl-1H-imidazole-5-carboxylate From Intermediate 101 and ethyl 2,4-dimethyl-1H-imidazole-5-carboxylate according to the method of Intermediate 17.

T.l.c. dichloromethane:methanol (20:1) Rf=0.4

EXAMPLE 154

1-[[3-Bromo-2-(2-carboxyphenyl)-5-benzofuranyl]methyl]-2,4-dimethyl-1H-imidazole-5-carboxylic acid From the product of example153 according to the method of Example 52.

m.p. 235° C. (decomp) T.l.c. ethyl acetate:acetic acid (10:1) Rf=0.1

EXAMPLE 155

1-[[3-Bromo-2-[2-(ethoxycarbonyl)phenyl]-5-benofuranyl]-methyl]-2,4-dimethyl-1H-imidazole-5-carboxylic acid From the product of Example 153 according to the method of Example 149.

EXAMPLE 156

Ethyl 1-[[3-bromo-2-(2-carboxyphenyl)-5-benzofuranyl]methyl]-2,4-dimethyl-1H-imidazole-5-carboxylate From the product of Example 153 according to the method of Example 149.

EXAMPLE 157

Ethyl 1-[[3-bromo-2-[2-[[(trifluoromethyl)sulphonyl]amino]phenyl]-5-benzofuranyl]methyl]-2-ethyl-4-(2-methylpropyl)-1H-imidazole-5-carboxylate From Intermediate 209 according to the method of Example 93.

T.l.c. ether Rf=0.51

EXAMPLE 158

1-[[3-Bromo-2-[2-[(trifluoromethyl)sulphonyl]amino]-phenyl]-5-benzofuranyl]methyl]-2-ethyl-4-(2-methylpropyl)-1H-imidazole-5-carboxylic acid From the product of Example 157 according to the method of Example 99.

T.l.c. dichloromethane:methanol (9:1) Rf=0.24

EXAMPLE 159

1-[[3-Bromo-2-[2-[(trifluoromethyl)sulphonyl]amino]-phenyl]-5-benzofouranyl]methyl]-2-ethyl-4-(2-methylpropyl)-1H-imidazole-5-carboxamide From the product of Example 158 according to the method of Example 103.

m.p. 200°–202° C. T.l.c. dichloromethane:methanol (9:1) Rf 0.21

EXAMPLE 160

1-[[3-Bromo-2-[2-[(trifluoromethyl)sulphonyl]amino]-phenyl]-5-benzofuranyl]methyl]-2-ethyl-N-methyl-4-(2-methylpropyl)-1H-imidazole-5-carboxamide From the product of example 158 and methylamine according to the method of

EXAMPLE 103.

m.p 160°–164° C. T.l.c. ethyl acetate:methanol (10:1) Rf=0.36

EXAMPLE 161

1-[[3-Bromo-2-[2-[[(trifluoromethyl)sulphonyl]amino]-phenyl]-5-benzofuranyl]methyl]-N,2-diethyl-4-(2-methylpropyl)-1H-imidazole-5-carboxamide From the product of example 158 according to the method of Example 115

T.l.c. dichloromethane:methanol (9:10) Rf=0.51 n.m.r. (CDCl$_3$) δ0.9(6H,d),1.1(6H,m),2.0(1H,m),2.5(4H,m),3.3(2H,m),-5.5(2H,s),6.0(1H,s),7.0–7.1(2H,m),7.4(2H,m),7.5(1H,m),7.7(2H,m).

EXAMPLE 162

1-[[3-Bromo-2-[2-[[(trifluoromethyl)sulphonyl]amino]-phenyl]-5-benzofuranyl]methyl]-2,4-diethyl-1H-imidazole-5-carboxamide From the product of Example 107 according to the method of Example 103.

m.p. 146°–151° C. (decomp) T.l.c dichloromethane:-methanol (15:1) Rf=0.23

EXAMPLE 163

1-[[3-Bromo-2-[2-[[(trifluoromethyl)sulphonyl]amino]-phenyl]-5-benzofuranyl]methyl]-2,4-diethyl-N-methyl-1H-imidazole-5-carboxamide From the product of Example 107 and methylamine according to the method of EXAMPLE 103.

m.p. 157°–162° C. (decomp) T.l.c. dichloromethane:-methanol (10:1) Rf=0.48

EXAMPLE 164

1-[[3-Bromo-2-[2-[[(trifluoromethyl)sulphonyl]sulphonyl]amino]phenyl]-5-benzofuranyl]methyl-N,2,4-triethyl-1H-imidazole-5-carboxamide From the product of Example of 107 according to the method of Example 115.

T.l.c. dichloromethane:methanol (4:1) Rf=0.7 n.m.r. (DMSO d$_6$) δ1.08(3H,t),1.15(3H,t),1.22(3H,t),2.65(2H,q),2.95(3H,q),3.25(2H,m),5.52(2H,s),6.88(1H,t),7.15–7.55(6H,m),8.25-(1H,m).

The compounds of the invention are tested in vitro for angiotensin II receptor antagonism. Aortic strips are obtained from male New Zealand white rabbits and prepared for recording isometric contractions in response to cumulative addition of angiotensin II. The potencies of test antagonists are assessed by measuring their abilities to displace the angiotensin II cumulative concentration response curve. The method used is that of Ackerly et al., Proc. Natl. Acad. Sci., 74(12), pp5725–28 (1977) with the exception that the final composition of the physiological salt solution is as given below in the Table

TABLE

| Ingredient | Amount (mM) |
| --- | --- |
| Na$^+$ | 143.4 |
| K$^+$ | 5.9 |
| Mg$^{2+}$ | 0.6 |
| Ca$^{2+}$ | 1.3 |
| Cl$^-$ | 124.5 |
| HPO$_4^-$ | 1.2 |
| SO$_4^{2-}$ | 0.6 |
| HCO$_3^-$ | 25.0 |
| glucose | 11.1 |
| indomethacin | 0.005 |
| ascorbic acid | 0.1 |

The tissues are initially challenged with K+(80 mM) and then washed at 0, 5, 10 and 15 minutes after the response to K+ has reached a plateau. After a further 45 minutes an angiotensin II cumulative response curve is constructed (0.1 nM to 0.1 μM in 10-fold increments) and the tissues are washed as before. A second, third and fourth angiotensin II cumulative response curve (0.1 nM to 0.1 μM in 3-fold increments) is then constructed at hourly intervals (15 minutes washing after each curve followed by 45 minutes equilibration). The compounds of the invention (30 μM) are tested for angiotensin II receptor antagonism by application 45 minutes before construction of the fourth angiotensin II curve. The third and fourth angiotensin II curves are expressed graphically and a concentration ratio (CR) is calculated by dividing the angiotensin II EC$_{50}$ value obtained in the presence of the test antagonist (i.e. fourth curve) by the angiotensin II EC$_{50}$ value obtained in the absence of the test antagonist (i.e. third curve).

The potency of the test antagonist is expressed as a pKb which is calculated from the equation:

$$pKb = -\text{Log}\left[\frac{CR - 1}{[\text{antagonist}]}\right]$$

which is a rearrangement of equation 4 described by Furchgott, in Handbook of Exp. Pharmacol., 33, p290 (1972) (eds. Blaschkott and Muscholl).

Compounds of the invention will desirably exhibit a pKb in the range between 5 and 12. Thus we have found that the compounds of the invention inhibit the action of the hormone angiotensin II and are therefore useful in the treatment of conditions in which it is desirable to inhibit angiotensin II activity. In particular, the compounds of the Examples have been tested in the above test and have been found to be active. There is thus provided as a further aspect of the present invention a compound of general formula (I) or a physiologically acceptable salt, solvate or metabolically labile ester thereof for use in the treatment of conditions associated with excessive or unregulated angiotensin II activity.

In a further or alternative aspect of the present invention there is provided a compound of general formula (I) or a physiologically acceptable salt, solvate or metabolically labile ester thereof for the manufacture of a therapeutic agent for the treatment of conditions associated with excessive or unregulated angiotensin II activity.

There is also provided in a further or alternative aspect of the present invention a method for the treatment of conditions associated with excessive or unregulated angiotensin II activity in a mammal including man comprising administration of an effective amount to a mammal in need of such treatment of a compound of general formula (I) or a physiologically acceptable salt, solvate or a metabolically labile ester thereof.

The following examples illustrate pharmaceutical formulations according to the invention. The term "active ingredient" is used herein to represent a compound of formula (I).

Pharmaceutical Example 1

| Oral Tablet A | |
|---|---|
| Active Ingredient | 700 mg |
| Sodium starch glycollate | 10 mg |
| Microcrystalline cellulose | 50 mg |
| Magnesium stearate | 4 mg |

Sieve the active ingredient and microcrystalline cellulose through a 40 mesh screen and blend in a appropriate blender. Sieve the sodium starch glycollate and magnesium stearate through a 60 mesh screen, add to the powder blend and blend until homogeneous. Compress with appropriate punches in an automatic tablet press. The tablets may be coated with a thin polymer coat applied by the film coating techniques well known to those skilled in the art. Pigments may be incorporated in the film coat.

Pharmaceutical EXAMPLE 2

| Oral Tablet B | |
|---|---|
| Active Ingredient | 500 mg |
| Lactose | 100 mg |
| Maize Starch | 50 mg |
| Polyvinyl pyrrolidone | 3 mg |
| Sodium starch glycollate | 10 mg |
| Magnesium stearate | 4 mg |
| Tablet Weight | 667 mg |

Sieve the active ingredient, lactose and maize starch through a 40 mesh screen and blend the powders in a suitable blender. Make an aqueous solution of the polyvinyl pyrrolidone (5–10% w/v). Add this solution to the blended powders and mix until granulated; pass the granulate through a 12 mesh screen and dry the granules in a suitable oven or fluid bed dryer. Sieve the remaining components through a 60 mesh screen and blend them with the dried granules. Compress, using appropriate punches, on an automatic tablet press.

The tablets may be coated with a thin polymer coat applied by film coating techniques well known to those skilled in art. Pigments may be incorporated in the film coat.

Pharmaceutical EXAMPLE 3

| Inhalation Cartridge | |
|---|---|
| Active Ingredient | 1 mg |
| Lactose | 24 mg |

Blend active ingredient, particle size reduced to a very fine particle size (weight mean diameter ca. 5 μm) with the lactose in a suitable powder blender and fill the powder blender into No. 3 hard gelatin capsules.

The contents of the cartridges may be administered using a powder inhaler.

Pharmaceutical Example 4

| Injection Formulation | % w/v |
|---|---|
| Active ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using dilute acid or alkali or by the addition of suitable buffer salts. Antioxidants and metal chelating salts may also be included.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

We claim:

1. A compound of formula (I)

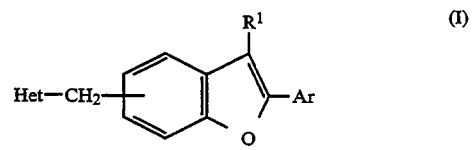

or a physiologically acceptable salt, hydrate or metabolically labile ester selected from the group consisting of lower alkyl ester, alkenyl ester, alkynl ester, alkoxyalkyl ester, alkylthioalkyl ester haloalkyl ester, alkanoyloxyalkyl ester, alkoxycarbonyloxyalkyl ester, substituted or unsubstituted aralkyl ester. substituted or unsubstituted aminoalkyl ester, and hydroxyalkyl ester, thereof wherein $R^1$ represents a halogen atom;

Ar represents the group

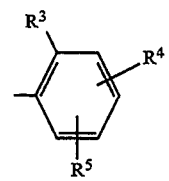

$R^3$ represents a C-linked tetrazolyl group;

$R^4$ and $R^5$, which may be the same or different, each independently represents a hydrogen atom or a halogen atom or a $C_{1-6}$ alkyl group;

Het represents an N-linked imidazolyl group optionally substituted at the 2-position by a $C_{1-6}$, $C_{2-6}$alkenyl or a $C_{1-6}$alkylthio group, the imidazolyl group optionally being substituted at the 4- and 5-positions by one or two further substituents selected from the group consisting of a halogen atom, a cyano group, a nitro group, $C_{1-6}$alkyl, $C_{2-6}$alkenyl, fluoroC$_{1-6}$alkyl, —(CH$_2$)$_m$R$^6$, —(CH$_2$)$_n$COR$^7$ and —(CH$_2$)$_p$NR$^8$COR$^9$;

R$^6$ represents a hydroxy or C$_{1-6}$alkoxy group;

R$^7$ is selected from the group consisting of a hydrogen atom, hydroxy, C$_{1-6}$alkyl, C$_{1-6}$alkoxy, phenyl, phenoxy, and —NR$^{10}$R$^{11}$;

R$^8$ represents a hydrogen atom or a C$_{1-6}$alkyl group;

R$^9$ is selected from the group consisting of a hydrogen atom, C$_{1-6}$alkyl, C$_{1-6}$alkoxy, phenyl, phenoxy, and —NR$^{10}$R$^{11}$;

R$^{10}$ and R$^{11}$, which may be the same or different, each independently represents a hydrogen atom or a C$_{1-4}$alkyl group;

m represents an integer from 1 to 4;

n represents an integer from 0 to 4; and p represents an integer from 1 to 4.

2. A compound of formula (I)

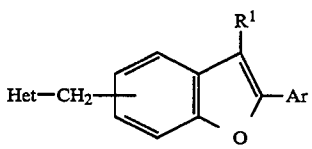
(I)

or a physiologically acceptable salt, hydrate, or metabolically labile ester selected from the group consisting of lower alkyl ester, alkenyl ester, alkynyl ester, alkoxyalkyl ester, alkylthioalkyl ester, haloalkyl ester, alkanoyloxyalkyl ester, alkoxycarbonyloxyalkyl ester, substituted or unsubstituted aralkyl ester, substituted or unsubstituted aminoalkyl ester, and hydroxyalkyl ester, thereof
wherein R$^1$ represents a halogen atom;

Ar represents the group

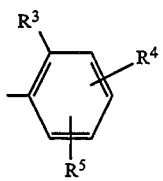

R$^3$ represents a C-linked tetrazolyl group;

R$^4$ and R$^5$, which may be the same or different, each independently represents a hydrogen atom or a halogen atom or a C$_{1-6}$alkyl group;

Het represents an N-linked imidazolyl group substituted at the 2-position by a C$_{1-6}$alkyl, C$_{2-6}$alkenyl or a C$_{1-6}$alkylthio group, the imidazolyl group optionally being substituted by one or two further substituents selected from the group consisting of a halogen atom, a cyano group, a nitro group, C$_{1-6}$alkyl, C$_{2-6}$alkenyl, perfluoroC$_{1-3}$alkyl, —(CH$_2$)$_m$R$^6$, —(CH$_2$)$_n$COR$^7$ and —(CH$_2$)$_p$NR$^8$COR$^9$;

R$^6$ represents a hydroxy or C$_{1-6}$alkoxy group;

R$^7$ is selected from the group consisting of a hydrogen atom, hydroxy, C$_{1-6}$alkyl, C$_{1-6}$alkoxy, phenyl, phenoxy, and —NR$^{10}$R$^{11}$;

R$^8$ represents a hydrogen atom or a C$_{1-6}$alkyl group;

R$^9$ is selected from the group consisting of a hydrogen atom, C$_{1-6}$alkyl, C$_{1-6}$alkoxy, phenyl, phenoxy, and —NR$^{10}$R$^{11}$;

R$^{10}$ and R$^{11}$, which may be the same or different, each independently represents a hydrogen atom or a C$_{1-4}$alkyl group;

m represents an integer from 1 to 4;

n represents an integer from 0 to 4; and p represents an integer from 1 to 4.

3. A compound according to claim 1 wherein m represents 1 or 2.

4. A compound according to claim 3 wherein m represents 1.

5. A compound according to claim 1 wherein n represents 0, 1 or 2.

6. A compound according to claim 5 wherein n represents 0 or 1.

7. A compound according to claim 1 wherein p represents 1 or 2.

8. A compound according to claim 1 wherein Het represents an N-linked imidazolyl group substituted at the 2-position by a hydrogen atom or a C$_{1-5}$alkyl group.

9. A compound according to claim 8 wherein Het represents an N-linked imidazolyl group substituted at the 2-position by a C$_{3-5}$alkyl group.

10. A compound according to claim 8 wherein said C$_{1-5}$alkyl group is an ethyl group.

11. A compound according to claim 9 wherein said C$_{3-5}$alkyl group is an n-propyl or an n-butyl group.

12. A compound according to claim 11 wherein said C$_{3-5}$alkyl group is an n-butyl group.

13. A compound according to claim 1 wherein Het represents an N-linked imidazolyl group substituted at the 2-position by a C$_{3-5}$alkenyl group.

14. A compound according to claim 13 wherein said C$_{3-5}$alkenyl group is a but-1-enyl group.

15. A compound according to claim 1 wherein the N-linked imidazolyl group is substituted by one or two further substituents selected from the group consisting of a halogen atom, C$_{1-6}$alkyl, —(CH$_2$)$_m$R$^6$ and —(CH$_2$)$_n$COR$^7$.

16. A compound according to claim 15 wherein said N-linked imidazolyl group is substituted by a halogen atom.

17. A compound according to claim 16 wherein said halogen atom is a chlorine atom.

18. A compound according to claim 15 wherein said N-linked imidazolyl group is substituted by a —(CH$_2$)$_m$R$^6$ or —(CH$_2$)$_n$COR$^7$ group.

19. A compound according to claim 18 wherein R$^6$ represents a hydroxy group or a C$_{1-6}$alkoxy group.

20. A compound according to claim 19 wherein R$^6$ represents a hydroxy group or a methoxy, ethoxy, propoxy or butoxy group.

21. A compound according to claim 20 wherein R$^6$ represents a hydroxy group or a methoxy group.

22. A compound according to claim 18 wherein R$^7$ is selected from the group consisting of hydrogen, hydroxy, C$_{1-6}$alkoxy and —NR$^{10}$R$^{11}$.

23. A compound according to claim 22 wherein R$^7$ is selected from the group consisting of hydrogen, hydroxy, methoxy, ethoxy, propoxy, and butoxy.

24. A compound according to claim 23 wherein R$^7$ is selected from the group consisting of hydrogen, hydroxy, and methoxy.

25. A compound according to claim 18 wherein m represents 1 or 2.

26. A compound according to claim 18 wherein n represents 0, 1 or 2.

27. A compound according to claim 18 wherein —(CH$_2$)$_m$R$^6$ is a —CH$_2$OH or —CH$_2$OCH$_3$ group.

28. A compound according to claim 18 wherein —(CH$_2$)$_n$COR$^7$ is a —CHO, —CO$_2$H, —CO$_2$CH$_2$CH$_3$ or —CONH$_2$ group.

29. A compound according to claim 18 wherein —(CH$_2$)$_n$COR$^7$ is a —CO$_2$CH$_3$ or —CONHCH$_3$ group.

30. A compound according to claim 1 wherein said group Het—CH$_2$— is attached at the 5- or 6-position on the benzofuran ring.

31. A compound according to claim 1 wherein said group Het—CH$_2$— is attached at the 5-position on the benzofuran ring.

32. A compound according to claim 1 wherein R$^1$ represents a bromine atom.

33. A compound according to claim 56 wherein R$^4$ and R$^5$ each independently represents a hydrogen atom or a halogen atom.

34. A compound according to claim 33 wherein R$^4$ and R$^5$ each independently represents a hydrogen atom.

35. A pharmaceutical composition comprising a compound of general formula (I) as defined in claim 1 or a physiologically acceptable salt, hydrate,or metabolically labile ester selected from the group consisting or lower alkyl ester, alkenyl ester, alkynyl ester, alkoxyalkyl ester, alkylthioalkyl ester, haloalkyl ester, alkanoyloxyalkyl ester, alkoxycarbonyloxyalkyl ester, substituted or unsubstituted aralkyl ester, substituted or unsubstituted aminoalkyl ester, and hydroxyalkyl ester, thereof,
together with at least one physiologically acceptable carrier or excipient.

36. A compound which is 1 -[[3-bromo-2-[2-(1H-tetrazol-5-yl)phenyl]-5benzofuranyl]methyl]-2-butyl-4-chloro-1 H-imidazole-5-carboxylic acid monohydrate.

37. A compound of formula (I)

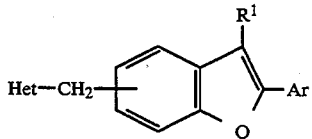

or a physiologically acceptable salt, hydrate, or metabolically labile ester selected from the group consisting of lower alkyl ester, alkenyl ester, alkynyl ester, alkoxyalkyl ester, alkylthioalkyl ester, haloalkyl ester, alkanoyloxyalkyl ester, alkoxycarbonyloxyalkyl ester, substituted or unsubstituted aralkyl ester, substituted or unsubstituted aminoalkyl ester, and hydroxyalkyl ester, thereof
wherein
R$^1$ represents a halogen atom;
Ar represents the group

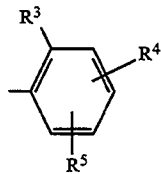

R$^3$ represents a C-linked tetrazolyl group;
R$^4$ and R$^5$ each independently represent a hydrogen atom or a halogen atom;
Het represents an N-linked imidazolyl group optionally substituted at the 2-position by a C$_{1-6}$alkyl or C$_{2-6}$alkenyl group, the imidazolyl group optionally being substituted at the 4- and 5-positions by one or two further substituents selected from the group consisting of halogen atom, C$_{1-6}$alkyl, —(CH$_2$)$_m$R$^6$, —(CH$_2$)$_n$COR$^7$ and —(CH$_2$)$_p$NR$^8$COR$^9$;
R$^6$ represents a hydroxy or a C$_{1-6}$alkoxy group;
R$^7$ is selected from the group consisting of hydrogen, hydroxy, C$_{1-6}$alkoxy and —NR$^{10}$R$^{11}$;
R$^8$ represents a hydrogen atom;
R$^9$ is selected from the group consisting of hydrogen, C$_{1-6}$alkyl, C$_{1-6}$alkoxy and —NR$^{10}$R$^{11}$;
R$^{10}$ and R$^{11}$ each independently represents a hydrogen atom or a C$_{1-4}$alkyl group;
m represents an integer from 1 to 4;
n represents an integer from 0 to 4; and
p represents an integer from 1 to 4.

38. A compound which is:
5-[2-[3-bromo-5-[[2-butyl-4-chloro-5-(hydroxymethyl)-1H-imidazol-1-yl]methyl]-2-benzofuranyl]-phenyl]tetrazole;
1-[[3-bromo-2-[2-(1H-tetrazol-5-yl)phenyl]-5-benzofuranyl]methyl]-2-butyl-4-chloro-1H-imidazole-5-carboxaldehyde;
5-[2-[3-bromo-5-[(2-butyl-1 H-imidazol-1 -yl)methyl]-2-benzofuranyl]phenyl]-1H-tetrazole; ethyl 1-[[3-bromo-2-[2-(1H-tetrazol-5-yl)phenyl]-5-benzofuranyl]methyl]-2-butyl-4-chloro-1 H-imidazole-5-carboxylate;
1-[[3-bromo-2-(1H-tetrazol-5-yl)phenyl]-5-benzofuranyl]methyl]-2-but-1(E)-enyl-4-chloro-1H-imidazole-5-carboxylic acid;
1-[[3-bromo-2-[2-(1H-tetrazol-5-yl)phenyl]-5-benzofuranyl]methyl]-4-chloro-2-propyl-1H-imidazole-5-carboxylic acid;
1-[[3-bromo-2-(1H-tetrazol-5-yl)phenyl]-5-benzofuranyl]methyl]-2-butyl-1H-imidazole-4,5-dicarboxylic acid;
5-[2-[3-bromo-5-[[2-butyl-4-chloro-5-(methoxymethyl)-1H-imidazol-1-yl]methyl]-2-benzofuranyl]-phenyl]-1H-tetrazole;
1-[[3-bromo-2-[2-(1H-tetrazol-5-yl)phenyl]benzofuran-5-yl]methyl]-2-butyl-4-chloro-1H-imidazole-5-carboxylic acid, (acetyloxy)methyl ester;
1-[[3-bromo-2-[2-(1 H-tetrazol-5-yl)phenyl]benzofuran-5-yl]methyl]-2-butyl-4-chloro-1H-imidazole-5-carboxylic acid, 1-(acetyloxy)ethyl ester;
1-(ethoxycarbonyloxy)ethyl1-[[3-bromo-2-[2-(1H-tetrazol-5-yl)phenyl]-5-benzofuranyl]methyl]-2-butyl-4-chloro-1H-imidazole-5-carboxylate;
2-methoxyethyl1-[[3-bromo-2-[2-(1 H-tetrazol-5-yl)phenyl]-5-benzofuranyl]methyl]-2-butyl-4-chloro-1H-imidazole-5-carboxylate;
1-[[3-bromo-2-[2-(1H-tetrazol-5-yl)phenyl]-5-benzofuranyl]methyl]-2-butyl-4-chloro-N-methyl-1H-imidazole-5-carboxamide;
1-[[3-bromo-2-[2-(1H-tetrazol-5-yl)phenyl]-5-benzofuranyl]methyl]-2-butyl-4-chloro-N-methyl-1H-imidazole-5-carboxamide;
1-[[3-bromo-2-[2-(1H-tetrazol-5-yl)phenyl]-5-benzofuranyl]methyl]-2-butyl-4-chloro-N,N-dimethyl-1H-imidazole-5-carboxamide;
1-[[3-bromo-2-[2-(1H-tetrazol-5-yl)phenyl]-5-benzofuranyl]methyl]-2-butyl-4-chloro-N-ethyl-1H-imidazole-5-carboxamide;
1-[[3-bromo-2-[2-(1H-tetrazol-5-yl)phenyl]-5-benzofuranyl]methyl]-4-chloro-2-ethyl-1H-imidazole-5-carboxylic acid;
1-[[3-bromo-2-[2-(1H-tetrazol-5-yl)phenyl]-5-benzofuranyl]methyl-2-butyl-1H-imidazole-5-carboxylic acid;

1-[[3-bromo-2-[2-(1H-tetrazol-5-yl)phenyl]-5-benzofuranyl]methyl]-2-propyl-4-chloro-N-methyl-1H-imidazole-5-carboxamide;

1-[[3-bromo-2-[2-(1H-tetrazol-5-yl)phenyl]-5-benzofuranyl]methyl]-2-butyl-4-chloro-N-isopropyl-1H-imidazole-5-carboxamide;

1-[[3-bromo-2-[2-(1H-tetrazol-5-yl)phenyl]-5-benzofuranyl]methyl]-2-butyl-4-iodo-1H-imidazole-5-carboxylic acid;

1-[[3-bromo-2-[2-(1H-tetrazol-5-yl)phenyl]-5-benzofuranyl]methyl]-2-butyl-4-trifluoromethyl-1H-imidazole-5-carboxylic acid;

1-[[3-bromo-2-[2-(1H-tetrazol-5-yl)phenyl]-5-benzofuranyl]methyl]-2-butyl-4methyl-1H-imidazole-5-carboxylic acid, hydrochloride (1:1);

1-[[3-bromo-2-[2-(1H-tetrazol-5-yl)phenyl]-5-benzofuranyl]methyl]-2-butyl-4-chloro-1H-imidazole-5-acetic acid;

ethyl [[3-bromo-2-[2-(1H-tetrazol-5-yl)phenyl]-5-benzofuranyl]methyl]-2-butyl-4-chloro-1H-imidazole-5-methylcarboxylate;

methyl [[1-[[3-bromo-2-[2-(1H-tetrazol-5-yl)phenyl]-5-benzofuranyl]methyl-2-butyl-4chloro-1H-imidazol-5-yl]methyl]carbamate;

1-[5-[3-chloro-2-[2-(1H-tetrazol-5-yl)phenyl]benzofuranyl]methyl]-2-butyl-4-chloro-1H-imidazole-5-carboxylic acid;

2-methoxy-1-methylethyl-[[3-bromo-2-[2-(1H-tetrazol-5-yl)phenyl]-5-benzofuranyl]methyl]-2-butyl-4-chloro-1H-imidazole-5-carboxylate;

or a physiologically acceptable salt, hydrate, or metabolically labile ester selected from the group consisting of lower alkyl ester, alkenyl ester, alkynyl ester, alkoxyalkyl ester, alkylthioalkyl ester, haloalkyl ester, alkanoyloxyalkyl ester, alkoxycarbonyloxyalkyl ester, substituted or unsubstituted aralkyl ester, substituted or unsubstituted aminoalkyl ester, and hydroxyalkyl ester, thereof.

39. A compound which is:

1-[[3-bromo-2-[2-(1H-tetrazol-5-yl)phenyl]-5-benzofuranyl]methyl]-2-butyl-4-chloro-1H-imidazole-5-carboxylic acid;

ethyl 1-[[3-bromo-2-[2-(1H-tetrazol-5-yl)phenyl]-5-benzofuranyl]methyl-2-butyl-4-chloro-1H-imidazole-5-carboxylate;

1-[[3-bromo-2-[2-(1H-tetrazol-5-yl)phenyl]-5-benzofuranyl]methyl]-4-chloro-2-propyl-1H-imidazole-5-carboxylic acid;

1-[[3-bromo-2-[2-(1H-tetrazol-5-yl)phenyl]-5-benzofuranyl]methyl]-2-butyl-4-chloro-N-methyl-1H-imidazole-5-carboxamide;

1-[[3-bromo-2-[2-(1H-tetrazol-5-yl)phenyl]-5-benzofuranyl]methyl-2-butyl-4-chloro-N-ethyl-1H-imidazole-5-carboxamide;

1-[[3-bromo-2-[2-(1H-tetrazol-5-yl)phenyl]-5-benzofuranyl]methyl]-4-chloro-2-ethyl-1H-imidazole-5-carboxylic acid;

1-[[3-bromo-2-[2-(1H-tetrazol-5-yl)phenyl]-5-benzofuranyl]methyl]-2-butyl-4-methyl-1H-imidazole-5-carboxylic acid, hydrochloride (1:1):

1-[5-[3-chloro-2-[2-(1H-tetrazol-5-yl)phenyl]benzofuranyl]methyl]-2-butyl-4-chloro-1H-imidazole-5-carboxylic acid;

ethyl1-[[3-bromo-2-[2-(1H-tetrazol-5-yl)phenyl]-5-benzofuranyl]methyl]-4-chloro-2-ethyl-1H-imidazole-5-carboxylate;

ethyl 1-[[3-bromo-2-[2-(1H-tetrazol-5-yl)phenyl]-5-benzofuranyl]methyl]-4-chloro-2-propyl-1H-imidazole-5-carboxylate;

ethyl 1-[[3-bromo-2-[2-(1H-tetrazol-5-yl)phenyl]-5-benzofuranyl]methyl]-4-methyl-2-proptyl-1H-imidazole-5-carboxylate;

ethyl 1-[[3-bromo-2-[2-(1H-tetrazol-5-yl)phenyl]-5-benzofuranyl]methyl]-2-butyl-4-methyl-1H-imidazole-5-carboxylate;

ethyl1-[[3-bromo-2-[2-(1H-tetrazol-5-yl)phenyl]-5-benzofuranyl]methyl]-2-ethyl-4-methyl-1H-imidazole-5-carboxylate hydrochloride;

1-[[3-bromo-2-[2-(1H-tetrazol-5-yl)phenyl]-5-benzofuranyl]methyl]-4-methyl-2-propyl-1H-imidazole-5-carboxylic acid;

ethyl1-[5-[3-bromo-2-[2-(1H-tetrazol-5-yl)phenyl]-benzofuranyl]methyl]-2-butyl4-methyl-1H-imidazole-5-carboxylate;

1-[[3-bromo-2-[2-(1H-tetrazol-5-yl)phenyl]-5-benzofuranyl]methyl]-2-ethyl-4-methyl-1H-imidazole-5-carboxylic acid hydrochloride;

or a physiologically acceptable salt, hydrate, or metabolically labile ester selected from the group consisting of lower alkyl ester, alkenyl ester, alkynyl ester, alkoxyalkyl ester, alkylthioalkyl ester, haloalkyl ester, alkanoyloxyalkyl ester, alkoxycarbonyloxyalkyl ester, substituted or unsubstituted aralkyl ester, substituted or unsubstituted aminoalkyl ester, and hydroxyalkyl ester, thereof.

40. A compound which is 1-[[3-bromo-2-[2-(1H-tetrazol-5-yl)phenyl]-5benzofuranyl]methyl]-2-butyl-4-chloro-1H-imidazole-5-carboxylic acid; or a physiologically acceptable salt, hydrate, or metabolically labile ester selected from the group consisting of lower alkyl ester, alkenyl ester, alkynyl ester, alkoxyalkyl ester, alkylthioalkyl ester, haloalkyl ester, alkanoyloxyalkyl ester, alkoxycarbonyloxyalkyl ester, substituted or unsubstituted aralkyl ester, substituted or unsubstituted aminoalkyl ester, and hydroxyalkyl ester, thereof.

* * * * *